US008617830B2

(12) United States Patent
Yu

(10) Patent No.: US 8,617,830 B2
(45) Date of Patent: *Dec. 31, 2013

(54) METHOD FOR IDENTIFYING LINEAGE-RELATED ANTIBODIES

(75) Inventor: Guo-Liang Yu, Hillsborough, CA (US)

(73) Assignee: Epitomics, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,517

(22) Filed: Jul. 18, 2012

(65) Prior Publication Data

US 2012/0283134 A1 Nov. 8, 2012

Related U.S. Application Data

(63) Continuation of application No. 12/878,925, filed on Sep. 9, 2010, now Pat. No. 8,293,483.

(60) Provisional application No. 61/241,714, filed on Sep. 11, 2009.

(51) Int. Cl.
*C07K 16/00* (2006.01)
*G01N 33/53* (2006.01)

(52) U.S. Cl.
USPC ........................................ 435/7.1; 530/387.1

(58) Field of Classification Search
None
See application file for complete search history.

(56) References Cited

U.S. PATENT DOCUMENTS

| | | | |
|---|---|---|---|
| 4,727,037 A | 2/1988 | Ring | |
| 4,816,567 A | 3/1989 | Cabilly et al. | |
| 4,859,595 A | 8/1989 | Strosberg et al. | |
| 4,977,081 A | 12/1990 | Raybould et al. | |
| 5,472,868 A | 12/1995 | McCormack et al. | |
| 5,610,034 A | 3/1997 | Nyyssonen et al. | |
| 5,876,961 A | 3/1999 | Crowe et al. | |
| 5,962,255 A | 10/1999 | Griffiths et al. | |
| 6,372,214 B1 | 4/2002 | Prusiner et al. | |
| 7,871,611 B2 | 1/2011 | Calzone et al. | |
| 8,293,483 B2 * | 10/2012 | Yu .................................. | 435/7.1 |
| 2001/0036647 A1 | 11/2001 | Choudary et al. | |
| 2002/0177170 A1 | 11/2002 | Luo et al. | |
| 2004/0010376 A1 | 1/2004 | Luo et al. | |
| 2006/0099204 A1 | 5/2006 | Couto et al. | |
| 2007/0037217 A1 | 2/2007 | Luo et al. | |
| 2008/0207459 A1 | 8/2008 | Karrer et al. | |
| 2008/0227660 A1 | 9/2008 | Kastrup et al. | |
| 2009/0054254 A1 | 2/2009 | Throsby et al. | |
| 2009/0081190 A1 | 3/2009 | Stassar et al. | |
| 2010/0292083 A1 | 11/2010 | Kolkman | |

FOREIGN PATENT DOCUMENTS

| | | |
|---|---|---|
| WO | WO0029584 | 5/2000 |
| WO | WO0148485 | 7/2001 |
| WO | WO2006055778 | 5/2006 |
| WO | WO2007056441 | 5/2007 |

OTHER PUBLICATIONS

Acosta, et al., Specific monoclonal antibody against human trypsin, Hybrid Hybridomics, 2002, 21:307-10.
Babcook, et al., A novel strategy for generating monoclonal antibodies from single, isolated lymphocytes producing antibodies of defined specificities, Proc Natl Acad Sci USA, 1996, 93:7843-8.
Becker, et al., Somatic diversification of immunoglobulin heavy chain VDJ genes: evidence for somatic gene conversion in rabbits, Cell, 1990, 63:987-97.
Bos, et al., Humoral immune response to 2,4-dinitrophenyl—keyhole limpet hemocyanin in antigen-free, germ-free and conventional BALB/c mice, Eur J Immunol, 1994, 24:59-65.
Calame, Plasma cells: finding new light at the end of B cell development, Nat Immunol, 2001, 2:1103-8.
Coronella, et al., Amplification of IgG VH and VL (Fab) from single human plasma cells and B cells, Nucleic Acids Res., 2000, 28:1-7.
De Wildt, et al., A new method for the analysis and production of monoclonal antibody fragments originating from single human B cells, J Immunol Methods, 1997, 207:61-7.
Durocher, et al., High-level and high-throughput recombinant protein production by transient transfection of suspension-growing human 293-EBNA1 cells, Nucleic Acids Res, 2002, 30:E9.
Embleton, et al., In-cell PCR from mRNA: amplifying and linking the rearranged immunoglobulin heavy and light chain V-genes within single cells, Nucleic Acids Res., 1992, 20:3831-7.
Friedmann, et al., Neonatal VH, D, and JH gene usage in rabbit B lineage cells, 1994, J. Immunology, 152:632-641.
Huse, et al., Generation of a large combinatorial library of the immunoglobulin repertoire in phage lambda, 1992, Biotechnology, 24:517-23.
Knight, et al., Molecular basis of the allelic inheritance of rabbit immunoglobulin VH allotypes: Implications for the generation of antibody diversity, Cell, 1990, 60:963-970.
Kurome, et al., Expression of recombinant mouse/human chimeric antibody specific to human GMP-140/P-selectin, J Biochem. 1994, 115:608-14.

(Continued)

*Primary Examiner* — Michail Belyavskyi
(74) *Attorney, Agent, or Firm* — James S. Keddie; Bozicevic, Field & Francis, LLP

(57) ABSTRACT

In certain embodiments, the method may comprise: a) obtaining the antibody sequences from a population of B cells; b) grouping the antibody sequences to provide a plurality of groups of lineage-related antibodies; c) testing a single antibody from each of the groups in a bioassay and, after the first antibody has been identified, d) testing further antibodies that are in the same group as the first antibody in a second bioassay. In another embodiment, the method may comprise: a) testing a plurality of antibodies obtained from a first portion of an antibody producing organ of an animal; b) obtaining the sequence of a first identified antibody; c) obtaining from a second portion of said antibody producing organ the sequences of further antibodies that are related by lineage to said first antibody; and, c) testing the further antibodies in a second bioassay.

14 Claims, 13 Drawing Sheets

(56) References Cited

OTHER PUBLICATIONS

Lagerkvist, et al., Single, antigen-specific B cells used to generate Fab fragments using CD40-mediated amplification or direct PCR cloning, Bio Techniques, 1995, 18:862-869.

Magori-Cohen, et al., Mutation parameters from DNA sequence data using graph theoretic measures on lineage trees, Bioinformatics, 2006, 22:e332-e340.

Marks, et al., By-passing immunization: human antibodies from V gene libraries displayed on phage, J Mol Biol, 1991, 222: 581-597.

Merz, et al., Generating a phage display antibody library against an identified neuron, J Neurosci Methods, 1995, 62:213-9.

Ochsenbein, et al., Protective long-term antibody memory by antigen-driven and T help-dependent differentiation of long-lived memory B cells to short-lived plasma cells independent of secondary lymphoid organs, Proc. Natl. Acad. Sci., 2000, 97:13263-13268.

Orlandi, et al., Cloning immunoglobulin variable domains for expression by the polymerase chain reaction, Proc. Natl. Acad. Sci. USA, 1989, 86:3833-3837.

Owens, et al., The genetic engineering of monoclonal antibodies, J Immunol Methods. 1994, 168:149-65.

Rudikoff, et al., Single amino acid substitution altering antigen-binding specificity, Proc Natl Acad Sci US, 1982, 79:1979-1983.

Sastry, et at., Cloning of the immunological repertoire in *Escherichia coli* for generation of monoclonal catalytic antibodies: construction of a heavy chain variable region-specific cDNA library, Proc. Natl. Acad. Sci., 1989, 86:5728-5732.

Scheid, et al., Broad diversity of neutralizing antibodies isolated from memory B cells in HIV-infected individuals, Nature, 2009, 458:636-640.

Scheid, et al., Broad diversity of neutralizing antibodies isolated from memory B cells in HIV-infected individuals, Nature, 2009, 458:636-640 (supplemental material), http://www.nature.com/nature/journal/v458/n7238/suppinfo/nature07930.html.

Sehgal, et al., Analyses of single B cells by polymerase chain reaction reveal rearranged VH with germline sequences in spleens of immunized adult rabbits: implications for B cell repertoire maintenance and renewal, J Immunol., 1998, 161:5347-5356.

Slifka, et al., Long-lived plasma cells: a mechanism for maintaining persistent antibody production, Curr Opin Immunol. 1998, 10:252-8.

Spieker-Polet, et al., Rabbit monoclonal antibodies: generating a fusion partner to produce rabbit-rabbit hybridomas, Proc Natl Acad Sci USA, 1995, 92:9348-52.

Takahashi, et al., The direct cloning of the immunoglobulin VH genes from primary cultured B cells specific for a short peptide, J Biotechnol, 1996, 49:201-10.

Wrammert, et al., Rapid cloning of high-affinity human monoclonal antibodies against influenza virus, Nature, 2008, 453:1-6.

Wrammert, et al., Rapid cloning of high-affinity human monoclonal antibodies against influenza virus, Nature, 2008, 453:1-19 (supplemental material).

\* cited by examiner

```
CARDINSYGYAY      AIDIW
CARSGZASS         VYNLW
CARSDMSYGG        AYDIW
CARSVDSIG         TDIW
CSGYYINI              W
CARCGAISGYT       YPNIW
CARGCPGYG         DWDIW
CARGVWSLD          IW
CVRDSTGISA        LEWIW
CARRGATASHR       WFIIW
CCSGAMIENEF       FNAIW
CARSDAS

>Clone 31-VK SEQ ID NOS: 115 and 116
atggacacgaggggcccccactcagctgctggggctcctGCTGCTCTGGCTCCCAGGTGcc
 M  D  T  R  A  P  T  Q  L  L  G  L  L  W  L  P  G  A
acatttgctcaactgctgacccagactgcatcgccctgtctacacagctgtgggaggcaca
 T  F  A  Q  L  T  Q  T  A  S  P  V  S  T  A  V  G  G  T
gtcaccatcaagtgccagtccagtcagagtgtttttaagaggaagtcctatctggtat
 V  T  I  K  C  Q  S  S  Q  S  V  F  K  R  K  S  L  W  Y
cagcagaaaccagggcaggctcccaaactcctgatctacgatgcatccactctggcatct
 Q  Q  K  P  G  Q  A  P  K  L  L  I  Y  D  A  S  T  L  A  S
ggggtcccatcacggttcagtggcagtggatctgggacacagttcactctcaccatcagc
 G  V  P  S  R  F  S  G  S  G  S  G  T  Q  F  T  L  T  I  S
ggcgtgcagtgtgacgatgctgccacttactgtCTAGGCAGTTTTGATTGTACTAGT
 G  V  Q  C  D  D  A  A  T  Y  C  L  G  S  F  D  C  T  S
GCTGATTGTCATGTTttcggcggagggaccgaggtggtggtcaaa
 A  D  C  H  V  F  G  G  G  T  E  V  V  V  K PCR primers:   Reverse for Clone 31-VK
               Forward for Clone 31-VK AACATGACAATCAGCACTAGTACAATCAAAACTGCCTAG (SEQ ID NO: 117)
GCTGCTCTGGCTCCCAGGTG (SEQ ID NO: 118)

```
                       1         2          ---CDR1---      3         4              ---CDR2--     6         7         8           ---CDR3-----    10
         12345678901234567890abcdef1234567890 1234567890abcde67890123456789012345678901234567890123456789012345abcde6789012345 67
31L-59   QLLTCTASPVSTAVGGTVTIKCQSSCSVFKRK      SLSWYQQKPGQAPKLLIYDASTLASGVPSRFSGSGSGTQFTLTISGVQCDDAATYCLGSFDCTSADC_HVFGGGTEVVVK  (SEQ ID NO: 119)
11--34   ------------------------------        --------------------------------------------------------------------------------  (SEQ ID NO: 119)
12--38   -V--------A-------------N----         ---Y-------------------------------------------------------------------------   (SEQ ID NO: 120)
2L-7     -V--------A-------------------        ---Y-------------------------------------------------------R-----------------   (SEQ ID NO: 121)
25--26   -V--------A-----------Y---            ---Y--------P--------------K---------------------------R----------------       (SEQ ID NO: 122)
22   26  -V----------------------Y             ---------------------P-------K-----------------------------------------       (SEQ ID NO: 123)
17--2    -V--------A-------------------        ---Y--------P--------------K--------------E------------Y-ST--------G---       (SEQ ID NO: 124)
3L-12    -V--------A-----------Y-S             HC----------P----------T----K------------------------A--Y-L--------------      (SEQ ID NO: 125)
1L-1     -V-P-S----A-----------Y-S             H---F-------P----------T----K-----------------------A--Y-L-------------       (SEQ ID NO: 126)
19   11  -V-P-S----A-----------Y-S             H---F-------P----------T----K-----------------------A--Y-L-------------       (SEQ ID NO: 127)
24--21   -V--------A----------N-A--Y-S         H-----------P---------------K-------------H-------------Y-SR------------       (SEQ ID NO: 128)
23--16   -V-P------A----------N-A--Y-S         H-----------P---------------K-------------H-------------Y-SR------------       (SEQ ID NO: 129)
18--6    -V-P------A----------N-RA-T-Y-S       H-----------P---------------K---------------------------Y-S-T-----------      (SEQ ID NO: 130)
13--11   -V-P------A----------N-A-R-Y-N        -------------R--------------------E-----------------------Y-IT-----------     (SEQ ID NO: 131)
10--28   -V-P------A----------N-A--Y---        -------------------------------------L---------------------Y-SRT----A--L-     (SEQ ID NO: 132)
21--21   -V-P------A----------N-A--Y---        Y----------K-------------------------------------------Y-SRT----A--L-         (SEQ ID NO: 133)
```

Figure 4A

```
>Clone 29-VK SEQ ID NOS: 131 and 132
atggacacgagggcccccactcagctgctgggctcctGCTGCTCTGGCTCCCAGGTGcc
 M  D  T  R  A  P  T  Q  L  -  G  L  L  L  W  L  P  G  A
atatgtgaccctgtgactgacccagactcccatccgtctgcagctgtgggaggcaca
 I  C  D  P  V  L  T  Q  T  P  S  S  V  S  A  A  V  G  G  T
gtcaccatcaattgccagtccagtcagagggtttggaagaacagctacttatcctgttt
 V  T  I  N  C  Q  S  S  Q  R  V  W  K  N  S  Y  L  S  W  F
cagcagaaaccagggcagcctcccaagcgcctccatcatatatacatccactctgccatct
 Q  Q  K  P  G  Q  P  P  K  R  L  I  Y  T  S  T  L  P  S
ggggtcccatcgcggttcaaaggcagtggatctgggacacagtcactctcaccatcagc
 G  V  P  S  R  F  K  G  S  G  S  G  T  Q  F  T  L  T  I  S
gacctggagtgtgacgatgctgccacttactactgtCTAGGGAGTTATAGTGATGATATA
 D  L  E  C  D  D  A  A  T  Y  Y  C  L  G  S  Y  S  D  D  I
TATTCTttcggcggagggaccgaggtggtcaaa
 Y  S  F  G  G  G  T  E  V  V  K
```

PCR primers:      Reverse for Clone 29-VK    AGAATATATATCATCACTATAACTCCCTAG (SEQ ID NO: 133)
                  Forward for Clone29-VK     GCTGCTCTGGCTCCCAGGTG (SEQ ID NO: 134)

```
              1         2         3         4         5         6         7         8
     12345678901234567890abcdef1234567890abcdef123456789012345678901234567890123456789012345abcde67890123456 7
     ===CDR1======      ==CDR2==           ====CDR3====       10
29L-48  DPVLTQTPSSVSAAVGGTVTINCQSSQRVWKNS YLSWFQQKPGQPPKRLIYTSTLPSGVPSRFKGSGSGTQFTLTISDLECDDAATYYCLGSYSDDI  YSFGGGTEVVVK  (SEQ ID NO: 135)
8L-16   ------------------------------- ------------------------------------------------------------------- ------------  (SEQ ID NO: 135)
9L-24   ------------------------------- ------------------------------------------------------------------- ------------  (SEQ ID NO: 135)
16--63  ------------V--A--------------- ------------------------------------------------------GVQ---------- ------------  (SEQ ID NO: 135)
32--20  ------------------------------- ----------------------------------------------------------------S-Y -K----------  (SEQ ID NO: 136)
```

Figure 4B

>Clone 27-VK SEQ ID NOS: 137 and 138
atggacacgagggcccccactcagctgctgggctcctGCTGCTCTGGCTCCCAGGTGcc
 M  D  T  R  A  P  T  Q  L  L  G  L  L  L  L  W  L  P  G  A
acatttgcgcaagtgctgacccagactgcatcgcccgtgtctgcacctgtggaggcaca
 T  F  A  Q  V  L  T  Q  T  A  S  P  V  S  A  P  V  G  G  T
gtcaccatcaattgccagtccagtcagagtgtttataataacaacgaattatcttggtat
 V  T  I  N  C  Q  S  S  Q  S  V  Y  N  N  N  E  L  S  W  Y
cagcagaaaccaggacagcctcccaagctcctgatctatgctgcatccatttggcatct
 Q  Q  K  P  G  Q  P  P  K  L  L  I  Y  A  A  S  I  L  A  S
gggtcccattgcggttcaaaggcagtggatctgggacacagttcactctcaccatcagc
 G  V  P  L  R  F  K  G  S  G  S  G  T  Q  F  T  L  T  I  S
gacctggagtgtgacgatgctgccacttactgtCAAGGCAGTTATTATAGTGGTGGT
 D  L  E  C  D  D  A  A  T  Y  C  Q  G  S  Y  Y  S  G  G
TGGTACAATGCTttcggcgggaggaccgaggtggtggtcaaa
 W  Y  N  A  F  G  G  G  T  E  V  V  V  K PCR primers:    Reverse for Clone 27-VK    AGCATTGTACCAACCACCACCACTATAATAACTGCCTTG (SEQ ID NO: 139)
                Forward for Clone 27-VK    GCTGCTCTGGCTCCCAGGTG (SEQ ID NO: 118)

```
          1         2         3         4         5         6         7         8         9         10
 12345678901234567890Cabcdef1234567890Cabcdef123456789012345678901234567890123456789012345abcde6789012345 67
27L-38 _QVLTQTASPVSAPVGGTVTINCQSSQSVYNNN____ELSWYQQKPGQPPKLLIYAASILASGVPLRFKGSGSGTQFTLTISDLECDDAATYYCQGSYYSGGWY__NAFGGGTEVVVK (SEQ ID NO: 140)
          1    ===CDR1========       2       ==CDR2=   3    4     5    6    7     =====CDR3===== 10
```

Figure 4C

>Clone 20-VK SEQ ID NOS: 141 and 142
atggacacgagggcccccactcagctgctggggtcctGCTGCTCTGGCTCCCAGGTGcc
 M  D  T  R  A  P  T  Q  L  L  G  L  L  L  L  W  L  P  G  A
acatttgctcaagtgctgacccagactccaccctccgtgtctgcagctgtgggaggcaca
 T  F  A  Q  V  L  T  Q  T  P  P  S  V  S  A  A  V  G  G  T
gtcaccatcagttgccagtccagtcagagcgtttataataactggttaggctggtat
 V  T  I  S  C  Q  S  S  Q  S  V  Y  N  N  N  W  L  G  W  Y
cagcagaaatcagggcagcctcccaagctcctgatctattatgcatccactctggcatct
 Q  Q  K  S  G  Q  P  P  K  L  L  I  Y  Y  A  S  T  L  A  S
ggggtctcatcgcggttcaaaggcagtggatctgggacacagttcactctcaccatcagc
 G  V  S  S  R  F  K  G  S  G  S  G  T  Q  F  T  L  T  I  S
gacctggagtgtgacgatgctgccacttattgtGCAGGCGGTTATAGTGATATGATG
 D  L  E  C  D  D  A  A  T  Y  Y  C  A  G  G  Y  S  D  M  M
AATGCTttcggcggagggactgaggtggtggttaaa
 N  A  F  G  G  G  T  E  V  V  V  K PCR primers: Reverse for Clone 20-VK    GCAGGCGGTTATAGTGATATGATGAATGCT (SEQ ID NO: 143)
             Forward for Clone 20-VK    GCTGCTCTGGCTCCCAGGTG (SEQ ID NO: 118)

```
             1         2 ===CDR1======    4                     ===CDR2=    6               8      ====CDR3==== 10
    1234567890123456789 0abcde=123456789012345 6789012345 67890123456789C1234567890123 45 67890123 45abcde67890123 4567
20L-17 _QVLTQTPPSVSAAVGGTVTISCQSSQSVYNNN___WLGWYQQKSGQPPKLLIYYASTLASGVSSRFKGSGSGTQFTLTISDLECDDAATYYC**AGGYSDMM___NAF**GGGTEVVVK   (SEQ ID NO: 144)
```

```
>Clone 29-VH SEQ ID NOS: 163 and 164
atggagactggg CTGCGCTGGCTTCTCCTGGTC gctgtgctcaaaggtgtccagtgtcag
 M  E  T  G   L  R  W  L  L  V  A  V  L  K  G  V  Q  C  Q
tcgctggagagtccgggggtccgcctggtaacgcctggagatccctgacactcacctgc
 S  L  E  E  S  G  G  R  L  V  T  P  G  G  S  L  T  L  T  C
acagtctctggaatcgacctcagtacctatccagtaccctatccaatgggctgggtccgccaggctccaggg
 T  V  S  G  I  D  L  S  T  Y  P  M  G  W  V  R  Q  A  P  G
aagggctggagtacatcggaatcgttttttcctagtcttggctcatattacgcgagctgg
 K  G  L  E  Y  I  G  I  V  F  P  S  L  G  S  Y  Y  A  S  W
gcaaaaggccgattcaccatctccaaaacctcgtcaaccacgtggatctgcgcatgacc
 A  K  G  R  F  T  I  S  K  T  S  S  T  T  V  D  L  R  M  T
agtctgacaaccgaggacacgccacctatttctgtgccagagg GGTAACTAATAGTTGG
 S  L  T  E  D  T  A  T  Y  F  C  A  R  G  V  T  N  S  W
GATCCCTGGG gcccaggcaccctggtcaccgtctcctca
 D  P  W  G  P  G  T  L  V  T  V  S  S PCR primers:   Reverse for Clone 29 VH    CCCAGGGATCCCAACTATTAGTTACC (SEQ ID NO: 165)
               Forward for Clone 29-VH    CTGCGCTGGCTTCTCCTGGTC (SEQ ID NO: 148)

1         2         =CDR1==   4         =CDR2=====     7         =CDR3========      11
      123456789012345678901abc345678901234567890123456789012abc34567890abcdefghijyz123456789012 3

8H-3    QSLEESGGGRLVSPGGSLTLTCTVSGIDLST__YPMGWVRQAPGKGLEYIGIVF___PSLGSYYASWAKGRFTISKTSS_TTVDLRMTSLTAEDTATYFCARGVTN_____SWDP WGPGTVTVSS
(SEQ ID NO: 166)
9--7    ----------------------------------------------------------------------------------------------------------|||-----
16H-82  -------T-----------------------------------------------------------T---------------------------------------|||-----
29H-35  -------T-----------------------------------------------------------T---------------------------------------|||-----L-
(SEQ ID NO: 167)
32H-21  ----------------------------------------------S-----------------NI----------------------------------------|||-----L-
(SEQ ID NO: 168)
```

Figure 4F

```
>Clone 27-VH SEQ ID NOS: 169 and 170
atggagactgggCTGCGCTGGCTTCTCCTGGTCgctgtgctcaagtgtccagtgtcag
 M  E  T  G  L  R  W  L  L  L  V  A  V  L  K  G  V  Q  C  Q
tcgctggagagtccggggtccgctggtaacgcctggaggatccctgacactcacctgc
 S  L  E  E  S  G  G  R  L  V  T  P  G  G  S  L  T  L  T  C
acagtctctggaatcgactctagtcagtgaatggctgtatgagagctccgcaggctccaggg
 T  V  S  G  I  D  L  S  S  Y  G  M  G  W  V  R  Q  A  P  G
aagggtctggaatacatcgcaatcattagttatggtggtagagcatactacgcgagtgg
 K  G  L  E  Y  I  A  I  I  S  Y  G  G  R  A  Y  Y  A  S  W
gcgaaaggccgattcaccatctccagaacttcgaccgtggatctgaaaatgaccagt
 A  K  G  R  F  T  I  S  R  T  S  T  T  V  D  L  K  M  T  S
ctgacaacgcgaggacacggccacctatttctgtgccagagaGATTTAGCGCCTTTAACTTG
 L  T  T  E  D  T  A  T  Y  F  C  A  R  G  F  S  A  F  N  L
TGGGGCccaggcaccctggtcaccgtctcctca
 W  G  P  G  T  L  V  T  V  S  S PCR primers:  Reverse for Clone 27-VH    GCCCCACAAGTTAAAGGCGCTAAATC (SEQ ID NO: 171)
              Forward for Clone 27-VH    CTGCGCTGGCTTCTCCTGGTC (SEQ ID NO: 148)

1         2         =CDR1==   4                    ======CDR2======   7
     1234567890123456789012345678901ab234567890123456789012abc34567890123456789012345678901234567890123
27H-13 _QSLEESGGRLVTPGGSLTLTCTVSGIDLSS__YGMGWVRQAPGKGLEYIAIIS__YGGRAYYASWAKGRFTISRTS__TTVDLKMTSLTTEDTATYFCARGFS
(SEQ ID NO: 172)

8              9          ======CDR3=======     11
     456789012345678901abc34567890123456789012abcdefghiyz123456789012 3
                                                       AFNLWGPGTLVTVSS
```

Figure 4G

>Clone 20-VH SEQ ID NOS: 173 and 174
atggagactggctgcctgcgctggcttctcctgctcgtcgctgtgctcaaaggtgtccagtgtcag
 M  E  T  G  I  R  W  L  L  L  V  A  V  L  K  G  V  Q  C  Q
tcggtggtggagagtccggggagtcgcctggtcgcctgacactcacc
 S  V  V  E  E  S  G  G  R  L  V  T  P  G  T  P  L  T  L  T
tgcacagcctctggattctccctcagtaggtttgcaatgaggtgggtccgccaggctcca
 C  T  A  S  G  F  S  L  S  R  F  A  M  R  W  V  R  Q  A  P
gggaaggggctggaatacatcggagctcatcggagactgatgtgtaggacatactacgcgagg
 G  K  G  L  E  Y  I  G  A  I  E  -  D  G  R  T  Y  Y  A  R
tgggcgaaaggccgattcaccatttccaagaccctcgaccgcggtgcatctgaagttcacc
 W  A  K  G  R  F  T  I  S  K  T  S  T  A  V  H  L  K  F  T
agtccgacaaccgaggacacgggcacgtatttctgtaccagagagGCTGGTTACAATTCT
 S  P  T  E  D  T  G  T  Y  F  C  T  R  G       L  V  T  I  S
ACTTTGTGGGGCccaggcaccctggtcaccgtctcctca
  T  I  W  G  P  G  T  L  V  T  V  S  S PCR primers:  Reverse for Clone 20-VH    GCCCCACAAAGTAGAAATTGTAACCAGC (SEQ ID NO: 175)
              Forward for Clone 20-VH    CTGCGCTGGCTTCTCCTGGTC (SEQ ID NO: 148)

1          2          =CDR1==    4          =====CDR2======    7          8             9      ======CDR3=======    11
              1234567890123456789012345678901ab23456789012345678901234567890123456789012abc34567890123456789012abc34567890abcdefghiyz123456789123
20H-3  QSVVEESGGRLVTPGTPLTLTCTASGFSLSR  FAMRWVRQAPGKGLEYIGAIE    TDGRTYYARWAKGRFTISKTS  TAVHLKFTSPTTEDTGTYFCTRGLVT                ISTLWGPGTLVTVSS
(SEQ ID NO: 176)

Figure 4H

… # METHOD FOR IDENTIFYING LINEAGE-RELATED ANTIBODIES

CROSS-REFERENCING

This patent application is a continuation of U.S. patent application Ser. No. 12/878,925, filed on Sep. 9, 2010, now U.S. Pat. No. 8,293,483, which application claims the benefit of U.S. provisional application Ser. No. 61/241,714, filed on Sep. 11, 2009, which application is incorporated by reference herein in its entirety.

INTRODUCTION

Antibodies are proteins that bind a specific antigen. Generally, antibodies are specific for their targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and other diseases. There are currently over two dozen therapeutic antibody products on the market and hundreds in development.

There is a constant need for new antibodies and methods for making the same.

SUMMARY

In certain embodiments, the method may comprise: a) obtaining the antibody heavy chain sequences and the antibody light chain sequences from a population of B cells of an animal, wherein the population of B cells is enriched for B cells that produce antibodies that specifically bind to a target antigen; b) grouping the heavy and light chain sequences on the basis of sequence similarity to provide a plurality of groups of antibodies that are related by lineage; c) testing a single antibody from each of the groups in a first bioassay to identify a first antibody that has a biological activity; and, after the first antibody has been identified, d) testing further antibodies that are in the same group as the first antibody in a second bioassay, thereby identifying a second antibody that has the biological activity.

In other embodiment, the method may comprise: a) testing a plurality of antibodies obtained from a first portion of an antibody producing organ of an animal in a first bioassay to identify a first antibody that has a biological activity; b) obtaining the sequence of the first antibody; c) obtaining from a second portion of said antibody producing organ the heavy and light chain amino acid sequences of further antibodies that are related by lineage to said first antibody by PCR, using probes are designed using the sequence of the first antibody; and, c) testing a plurality of the further antibodies in a second bioassay to identify a second antibody that has said biological activity.

In certain embodiments, the method provides a means by which significant portion of the entire antibody repertoire of an animal can be screened to identify an antibody with desirable properties. In certain embodiments the method involves first identifying a single antibody with desirable properties, and then screening other antibodies in same lineage group (i.e., a clonally related group of antibodies) as the identified antibody, to identify other antibodies that may have even more desirable properties relative to the identified antibody. As such, the method provides an efficient way to screen for and identify new, biologically active antibodies. After identification, the second antibody may be tested in further assays, and, if it is suitable for use as a therapy, may be humanized, for example.

BRIEF DESCRIPTION OF THE DRAWINGS

FIG. 2 shows the amino acid sequences of selected KDR-binding antibodies. Page 1 of FIG. 2 shows amino acid sequences of the heavy chains. Page 2 of FIG. 2 shows amino acid sequences of the corresponding light chains. The amino acid sequences shown in FIG. 2 are of antibodies that specifically bind to KDR and block VEGF activity. From top to bottom, FIG. 2 (page 1 of 2) SEQ ID NOS: 1-47 and FIG. 2 (page 2 of 2) SEQ ID NOS: 48-94.

FIG. 3 shows the amino acid sequence of 20 exemplary VH3 regions of unrelated rabbit antibodies. From top to bottom SEQ ID NOS: 95-114.

FIGS. 4A-4H show exemplary methods by which related antibodies can be amplified.

DEFINITIONS

Figure 1A:
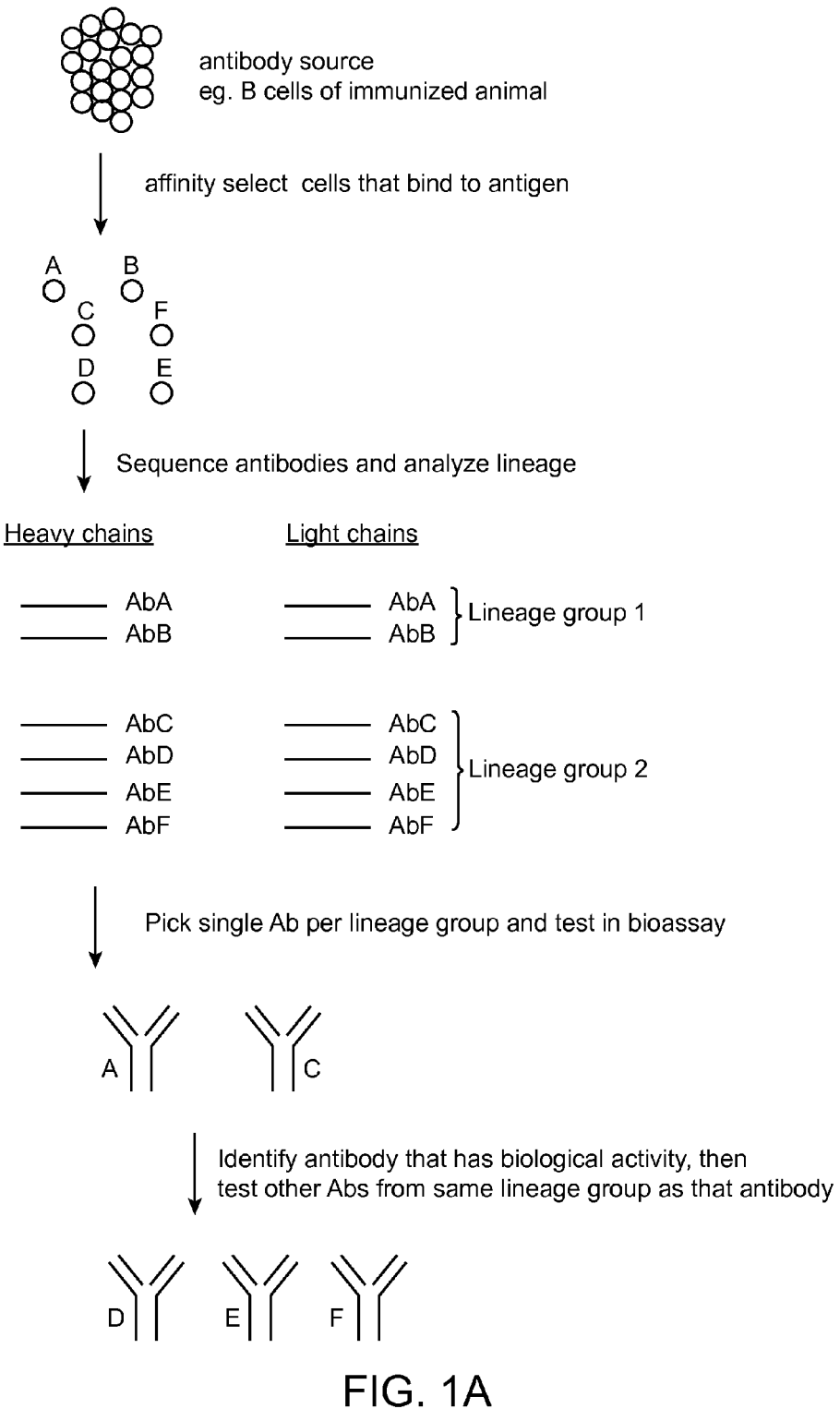
FIGS. 1A and 1B schematically illustrate two embodiments.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "nucleic acid" encompasses DNA, RNA, single stranded or double stranded and chemical modifications thereof. The terms "nucleic acid" and "polynucleotide" are used interchangeably herein.

The term "expression", as used herein, refers to the process by which a polypeptide is produced based on the nucleic acid sequence of a gene. The process includes both transcription and translation.

The term "expression cassette" refers to a nucleic acid construct capable of directing the expression of a gene/coding sequence of interest, which is operably linked to a promoter of the expression cassette. Such cassettes can be a linear nucleic acid or can be present in a "vector", "vector construct", "expression vector", or "gene transfer vector", in order to transfer the expression cassette into target cells. Thus, the term includes cloning and expression vehicles, as well as viral vectors.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "plurality" refers to more than 1, for example more than 2, more than about 5, more than about 10, more than about 20, more than about 50, more than about 100, more than about 200, more than about 500, more than about 1000, more than about 2000, more than about 5000, more than about 10,000, more than about 20,000, more than about 50,000, more than about 100,000, usually no more than about 200,000. A "population" contains a plurality of items.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed., 1984, and Hunkapiller and Hood, Nature, 323, 15-16, 1986).

An immunoglobulin light or heavy chain variable region consists of a framework region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody, although other mammalian species may be used.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The term "natural" antibody refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "non-naturally paired", with respect to VH and VL chains of an engineered antibody, refers to a VH and VL pair that is not found in a natural antibody. Thus, a non-naturally paired antibody is a combination of VH and VL chain of two different natural antibodies. The VH and VL chains of a non-naturally paired antibody are not mutated relative to the VH and VL chains of the two different antibodies which provided the VH and VL chains. For example, the "non-naturally paired" IgH and IgL chains of the engineered antibody may contain the IgH variable chain from a first antibody producing cell obtained from an animal and the IgL variable chain of second antibody producing cell obtained from the same animal, where the amino acid sequence of the antibody produced by the first cell is different from the amino acid sequence of the antibody produced by the second cell. In this example, the IgH and IgL chains may be from the same lineage group. An antibody containing "non-naturally paired" IgH and IgL chains may or not be made by phage display. As such, antibodies may or may not contain viral (e.g., bacteriophage M13)-derived sequences.

The term "lineage-related antibodies" and "antibodies that related by lineage" as well as grammatically-equivalent variants there of, are antibodies that are produced by cells that share a common B cell ancestor. Related antibodies produced by related antibody producing cells bind to the same epitope of an antigen and are typically very similar in sequence, particularly in their L3 and H3 CDRs. Both the H3 and L3 CDRs of lineage-related antibodies have an identical length and a near identical sequence (i.e., differ by up to 5, i.e., 0, 1, 2, 3, 4 or 5 residues). In certain cases, the B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies are related via a common antibody ancestor, e.g., the antibody produced in the naïve B cell ancestor. The term "related antibodies" is not intended to describe a group of antibodies that are not produced by cells that arise from the same ancestor B-cell. A "lineage group" contains a group of antibodies that are related to one another by lineage.

The terms "treating" or "treatment" of a condition or disease refer to providing a clinical benefit to a subject, and include: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

DETAILED DESCRIPTION OF EXEMPLARY EMBODIMENTS

One embodiment of the subject method is illustrated in FIG. 1A. With reference to FIG. 1A, this embodiment of the method may involve immunizing an antibody-producing animal with a selected antigen, and enriching from a larger population of antibody-producing cells that bind to the antigen. In FIG. 1, six different antibody producing cells A-F that produce antibodies that bind to a target antigen are enriched from a larger population of antibody producing cells. However, in many embodiments, there may be several hundred or several thousand enriched cells. Each of these cells produces a natural antibody that contains a naturally paired IgH and IgL chain. The amino acid sequences of the heavy and light chains of the antibodies produced by the enriched cells are obtained by sequencing the nucleic acids encoding the IgH and IgL chains of the antibodies, and the sequences are analyzed and put into lineage groups which, as discussed above, are groups of antibodies that are produced by cells that share a common B cell ancestor. Such antibodies generally have very similar sequences, and have H3 CDRs of identical length and near identical sequence as well as L3 CDRs of identical length and a near identical sequence. In the embodiment shown in FIG. 1A, the six antibody producing cells produce antibodies (AbA to AbF) that are in two lineage groups (i.e., lineage groups 1 and 2, where AbA and AbB are in lineage group 1 and AbC, AbD, AbE and AbF are in lineage group 2). After the antibodies have been placed into lineage groups, a single antibody (or, in certain cases, multiple antibodies (for example 2-10) from each lineage group) from at least one of the lineage group, e.g., AbA from lineage group 1 and AbC from lineage group 2, is selected for testing in a bioassay, where a bioassay identifies an antibody with a biological activity (e.g., a blocking or neutralizing activity). Once an antibody having a biological activity has been identified, e.g., AbC, other antibodies from the same lineage group as the identified antibody are tested to identify a second antibody that has the same biological activity as the first antibody. In the example shown in FIG. 1, antibodies D, E and F, which belong to the same lineage group as antibody C, were tested.

Many warm-blooded animals, in particular mammals such as humans, rabbits, mice, rats, sheep, cows, pigs and ayes such as chickens and turkeys, may be used as a source of antibody-produced cells. However, in certain embodiments a rabbit or mice is used because of their ease in handling, well-defined genetic traits, and the fact that they may be readily sacrificed. Procedures for immunizing animals are well known in the art, and are described in Harlow et al., (*Antibodies: A Laboratory Manual*, First Edition (1988) Cold Spring Harbor, N.Y.).

Suitable antigens include extracellularly-exposed fragments of Her2, GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL-related ligand), CAl25 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFalpha, TRAIL-R1, VAP-1 (vascular adhesion protein 1) or TNFα, or the like. In many embodiments, a peptide having the amino acid sequence corresponding to a portion of an extracellular domain of one of the above-listed proteins is employed as an antigen.

Antibody-producing cells may also be obtained from a subject which has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Antibody-producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes or tumors by dissociation with enzymes such as collagenase and trypsin in the presence of EDTA.

In exemplary embodiments, an affinity purification method is utilized to isolate antibody producing cells that produce antibodies that bind to an antigen. The antigen with which the animal was immunized may be immobilized on a solid phase and used to selectively retain antibody producing cells that express an antibody on their surface that binds to the antigen, while other cells are washed away. The retained cells may then be eluted by a variety of methods, such as by using an excess of the antigen, chaotropic agents, changing the pH, salt concentration, etc. Any of the well known methods for immobilizing or coupling antigen to a solid phase may be used. For example, when the antigen is a cancer cell, appropriately treated microtiter plate that will bind to cells may be used, such as microtiter plates for cell culture. In the instances where the antigen is a protein, the protein may be covalently attached to a solid phase, for example, sepharose beads, by well known techniques, etc. Alternatively, a labeled antigen may be used to specifically label cells that express an antibody that binds to the antigen and the labeled cells may then be isolated by cell sorting (e.g., by FACS). In certain cases, methods for antibody purification may be adapted to isolate antibody producing cells. Such methods are well known and are described in, for example, J Immunol Methods. 2003 November; 282(1-2):45-52; J Chromatogr A. 2007 Aug. 10; 1160(1-2):44-55; J Biochem Biophys Methods. 2002 May 31; 51 (3):217-31. Cells may also be isolated using magnetic beads or by any other affinity solid phase capture method, protocols for which are known. In some embodiments, antigen-specific antibody producing cells may be obtained from blood by flow cytometry using the methods described in Wrammert (Nature 2008 453: 667-672), Scheid (Nature 2009 458: 636-640), Tiller (J. Immunol. Methods 2008 329 112-124) or Scheid (Proc. Natl. Acad. Sci. 2008 105: 9727-9732), for example, which are incorporated by reference for disclosure of those methods. Exemplary antibody-producing cell enrichment methods include performing flow cytometry (FACS) of cell populations obtained from a spleen, bone marrow, lymph node or other lymph organs, e.g., through incubating the cells with labeled anti-rabbit IgG and sorting the labeled cells using a FACSVantage SE cell sorter (Becton-Dickinson, San Jose, Calif.). In some embodiments, single or nearly single antibody-producing cells are deposited in microtiter plates. If the FACS system is employed, sorted cells may be deposited after enrichment directly into a microtiter plate.

Enrichment may decrease the size of the cell population by at least 50%, e.g., at least 60%, at least 70%, at least 80%, at least 90%, at least 95% or at least 99% and in certain cases, the plurality of enriched antibody producing cells may be substantially pure, i.e., substantially free of other cells that do not produce an antibody that binds to the antigen, where the term "substantially pure" refers to an isolated population of antibody producing cells, in which cells that express antibodies that specifically bind to the antigen make up at least 5%, 10%, 20%, 30%, at least 40%, at least 50%, at least 60%, at least 70% or more of the total population of cells. The enriched population of antibody producing cells may be employed as a mixture of cells, or alternatively, they may be used as single cells, e.g., by dilution and deposition into individual wells of a microtiter plate.

The enriched population of antibody producing cells may comprise at least 5, at least 10, at least 30, at least 60, at least 100, at least 300, at least 500, at least 1000, at least 5,000, at least 10,000 or at least 100,000, or more antibody producing cells.

The isolated antibody-producing cells may be optionally cultured (i.e. grown in media that supports at least one, at least 5 or at least 10 or more cell divisions of the cell) by methods known to one of skill in the art after they have been deposited (see e.g. WO 01/55216).

In certain embodiments, the antibodies produced by the enriched cells are not well characterized. As such, although the antibody-producing cells are isolated based on the production of antibodies that specifically bind to the antigen, the epitope(s) to which these antibodies bind is unknown, and it is not known if the antibodies have any biological activity (e.g., a neutralizing or blocking activity). Additionally, the nucleic acid sequence or the amino acid sequence of the variable regions of IgH and IgL chains of these antibodies are not known.

Sequences encoding heavy and light chains may be amplified from the cDNA using techniques well known in the art, such as Polymerase Chain Reaction (PCR). See Mullis, U.S. Pat. No. 4,683,195; Mullis et al., U.S. Pat. No. 4,683,195; Polymerase Chain Reaction: Current Communication in Molecular Biology, Cold Springs Harbor Press, Cold Spring Harbor, N.Y., 1989. Briefly, cDNA segments encoding the variable domain of the antibody are exponentially amplified by performing sequential reactions with a DNA polymerase. The reaction is primed by a 5' primer and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the immunoglobulin chain. This combination of oligonucleotide primers has been used in the PCR amplification of murine immunoglobulin cDNAs of unknown sequence (see Sastry et at., Proc Natl. Acad. Sci. 86:5728-5732, 1989 and Orlandi et al., Proc. Natl. Acad. Sci. 86:3833-3837, 1989). Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites. In many embodiments, however, the entire polynucleotide encoding a heavy or light chain is amplified using primers spanning the start codons and stop codons of both of the immunoglobulin cDNAs, however, depending on the amplification products desired, suitable primers may be used. Exemplary primers for use with rabbit antibody-producing cells are as follows: heavy chain, 5' end (CACCATGGAGACTGGGCTGCGCTGGCT-TCTCCTGGTCGCTGTG; SEQ ID NO:177); heavy chain, 3' end (CTCCCGCTCTCCGGGTAAATGAGCGCT-GTGCCGGCGA; SEQ ID NO:178); light chain kappa, 5'end (CAGGCAGGACCCAGCATGGACAC-GAGGGCCCCCACT; SEQ ID NO:179); and L kappa, 3'end (TCAATAGGGTGACTGTTAGAGCGAGACGCCTGC; SEQ ID NO:180). Suitable restriction sites and other tails may be engineered into the amplification oligonucleotides to facilitate cloning and further processing of the amplification products. Amplification procedures using nested primers may also be used, where such nested primers are well known to one of skill in the art. Exemplary methods for amplifying antibody-encoding nucleic acid is also described in Wrammert (Nature 2008 453: 667-672) and Scheid (Nature 2009 458: 636-640), for example. In this embodiment, the enriched cells may be combined before sequencing (in which case the initial amplification product will contain a mixture of a plurality of different products that can be discriminated by cloning the products or using single molecule sequencing technologies), or the cells may be kept separate from one another (in which case the initial amplification product amplified from a single cell may contain a single species that can be sequenced).

In certain embodiments, at least 1,000 heavy chain sequences and at least 1,000 light chain sequences are obtained.

Once the amino acid sequence of heavy and light chains of the antibodies has been obtained, antibodies can be grouped on the basis of sequence similarity to provide a plurality of groups of antibodies that are related by lineage. Methods for performing clonal analysis of antibody sequences are well known and are described in a number of publications including Magori-Cohen (Bioinformatics 2006 22: e332-40), Manske (Clin. Immunol. 2006 120:106-20), Kleinstein (J. Immunol. 2003 171: 4639-49), Clement (Mol. Ecol. 2000 9: 1657-1659), Mehr (J. Immunol. 2004 172 4790-6), Wrammert (Nature 2008 453: 667-672), Scheid (Nature 2009 458: 636-640), which are incorporated by reference herein for disclosure of those methods. The antibodies placed into lineage groups should all be from a single animal, i.e., an individual mouse or rabbit.

In some embodiments, the amino acid positions of an antibody are numbered using a suitable numbering system, such as that provided by Chothia (J Mol Biol 1998; 278: 457-79) or Kabat (1991, Sequences of Proteins of Immunological Interest, DHHS, Washington, D.C.). CDR and/or framework residues may be identified using these methods. The numbered sequences may be aligned by eye, or by employing an alignment program such as one of the CLUSTAL suite of programs (Thompson et al Nucleic Acids Research, 22:4673-4680). The variable regions of antibodies within a related group of antibodies have amino acid sequences that are very similar. For example, the VH or VL domains of antibodies within a related group of antibodies may have amino acid sequences that are at least about 80% identical (e.g., at least 85% identical, at least 90% identical, at least 95% or at least 98% or at least 99% identical), ignoring any gaps or insertions made to facilitate alignment of the sequences. Antibodies within a related group of antibodies have a VL domains that are similar to each other, as well as VH domains that are similar to each other. In other words, in certain embodiments the VH or VL domains of two different related antibodies usually contain up to about ten (i.e., one, two, three, four or five or more) amino acid differences. An amino acid difference may be present at any position of the variable domain, including in any CDR or in any framework region. Certain related antibodies have H3 CDRs that are almost identical, as well as L3 CDRs that are almost identical. In these embodiments, any two antibodies that are related will have L3 and H3 CDRs that are each identical in length and have near identical sequences (i.e., that contain 0, 1, 2, 3, 4 or 5 amino acid changes). In other words the L3 CDRs of the two antibodies are identical in length and near identical in sequence and the H3 CDRs of the two antibodies are identical in length and near identical in sequence. Two exemplary sets of related antibodies are shown in FIG. 2, and the sequences of 20 exemplary VH3 regions of unrelated rabbit antibodies are shown for comparison in FIG. 3.

In certain embodiments, the heavy chain sequences may or may not be grouped independently of the light chain sequences. If the heavy and light chain sequences are grouped independently of one another, the heavy and light chain groups may be matched up by analysis of lineage trees.

Depending how many sequences are obtained, in certain embodiments the enriched antibodies may be grouped into at least 5 groups, at least 10 groups, at least 20 groups, at least 50 groups, or at least 100 groups or more, e.g., up to 200 or 500 groups or more. Depending how many sequences are obtained, each group may contain from 2 to several hundred or more antibodies.

Once the antibodies have been grouped, a single antibody from each of at least some of the groups (e.g., at least 20%, at least 50 or at least 80% of the groups) is tested in a first bioassay to identify a first antibody that has a biological activity. The bioassay may determine whether the antibody has a biological effect, e.g., an ability to inhibit an interaction between a receptor and an a ligand by either binding to the receptor and blocking binding of the ligand, or by binding to the ligand and neutralizing it, or by promoting or inhibiting a cellular phenotype, e.g., cell growth, cell proliferation, cell migration, cell viability (e.g., apoptosis), cell differentiation, cell adherence, cell shape changes (e.g., tubular cell formation), complement dependant cytotoxicity CDC, antibody-dependent cell-mediated cytotoxicity ADCC, receptor activation, gene expression changes, changes in post-translational modification (e.g., phosphorylatoin), changes in protein targeting (e.g., NFκB localization etc.), etc., or inhibition of receptor multimerization (e.g., dimer or trimerization) or receptor-ligand interactions, etc. Such bioassays are well known in the art. The term "bioassay" is intended to exclude assays in which only the ability of an antibody to bind to a target is read. Bioassays useful in this method are numerous, and include but are not limited to cellular assays in which a cellular phenotype is measured, e.g., gene expression assays; and in vivo assays that involve a particular animal (which, in certain embodiments may be an animal model for a condition related to the target). In certain cases, the assay may be a vascularization assay.

In this embodiment, the antibodies tested in the bioassay may contain naturally paired heavy and light chain variable domains, or non-naturally paired heavy and light chains (i.e., heavy and light chain variable domains from different antibodies of the same lineage group). Since the antibodies are from the same lineage group, it is expected that such antibodies will be functional.

After a first antibody that has a biological activity has been identified, further antibodies that are in the same lineage group as the first antibody are tested in a second bioassay, thereby identifying a second antibody that has the same biological activity as the first antibody. In certain cases at least 10%, at least 20%, at least 50%, or at least 80% of the antibodies in the same lineage group are tested. The first bioassay may be the same as or different to the second bioassay. In certain embodiments, a plurality of antibodies is tested, and the antibody with the best properties is chosen for future use.

In particular embodiments, the further antibodies may contain naturally paired heavy and light chain variable domains, or non-naturally paired heavy and light chain variable domains (i.e., heavy and light chain variable domains from different antibodies of the same lineage group). Since the antibodies are from the same lineage group, it is expected that such antibodies will be functional. In particular embodiments, the pairing of the heavy and light chains may be systematic (e.g., every heavy chain is tested in combination with every light chain) or random (e.g., every heavy chain is tested with randomly selected light chains), for example.

Exemplary VEGF bioassays include assays using isolated protein in a cell free systems, in vitro using cultured cells or in vivo assays. Exemplary VEGF assays include, but are not limited to a receptor tyrosine kinase inhibition assay (see, e.g., Cancer Research Jun. 15, 2006; 66:6025-6032), an in vitro HUVEC proliferation assay (FASEB Journal 2006; 20: 2027-2035), an in vivo solid tumor disease assay (U.S. Pat. No. 6,811,779) and an in vivo angiogenesis assay (FASEB Journal 2006; 20: 2027-2035). These assays are well known in the art. The descriptions of these assays are hereby incorporated by reference.

Exemplary TNF-α bioassays include in vitro assays using cell free systems or using cultured cells or in vivo assays. As such, TNF-α assays include in vitro human whole blood assay and cell mediated cytotoxicity assay (U.S. Pat. No. 6,090,382), in vitro tumor human killing assay (see, e.g., published U.S. patent application 20040185047), in vivo tumor regression assay (USP Application 20040002589). Additional TNF-α assays are described in a variety of publications, including 20040151722, 20050037008, 20040185047, 20040138427, 20030187231, 20030199679, and Balazovich (Blood 1996 88: 690-696).

A subject antibody inhibits at least one activity of its target in the range of about 20% to 100%, e.g., by at least about 20%, at least about 30%, at least about 40%, at least about 50%, at least about 60%, usually up to about 70%, up to about 80%, up to about 90% or more. In certain assays, a subject antibody may inhibits its target with an $IC_{50}$ of $1\times10^{-7}$ M or less (e.g., $1\times10^{-7}$ M or less, $1\times10^{-8}$ M or less, $1\times10^{-9}$ M or less, usually to $1\times10^{-12}$ M or $1\times10^{-13}$ M). In assays in which a mouse is employed, a subject antibody may have an $ED_{50}$ of less then 1 μg/mouse (e.g., 10 ng/mouse to about 1 μg/mouse). In certain embodiments, a subject antibody may be contacted with a cell in the presence of a ligand, and a ligand response phenotype of the cell is monitored.

In certain embodiments, particularly if the antigen elicits a strong response in the animal, the method may be practiced in the absence of any antigen-based enrichment of antibody producing cells prior to the first bioassay. In these embodiments, the method may involve: a) obtaining the antibody heavy chain sequences and the antibody light chain sequences from a population of B cells of an animal, wherein said population of B cells is not enriched for B cells that produce antibodies that specifically bind to a target antigen, b) grouping the heavy and light chain sequences on the basis of sequence similarity to provide a plurality of groups of antibodies that are related by lineage; c) testing a single antibody from each of the groups in a first bioassay to identify a first antibody that has a biological activity; and, after the first antibody has been identified; and d) testing further antibodies that are in the same group as the first antibody in a second bioassay, thereby identifying a second antibody that has the biological activity.

Figure 1B:
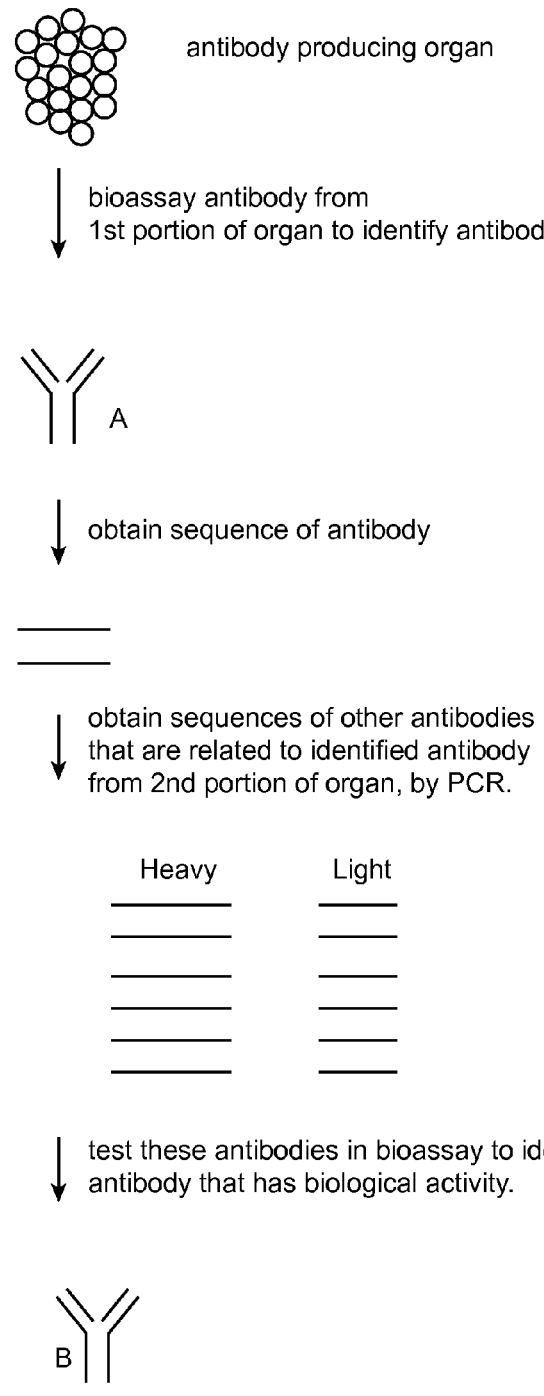

Another embodiment of is illustrated in FIG. 1B. With reference to FIG. 1B, this embodiment of the subject method may involve immunizing an antibody-producing animal with a selected antigen, and testing a plurality of antibodies produced by a first portion of an antibody producing organ of the animal (e.g., a first portion of the spleen, a first portion of the lymph nodes, a first portion of bone marrow, or a first portion of the peripheral blood mononuclear cell (PBMC) population in the bloodstream of the animal, etc.) in a bioassay to identify a first antibody that has a biological activity. In this embodiment, the first and second portions of an antibody-producing organ need not be spatially separated in the organ. Rather, since a first portion or an organ can be made by, for example, making a single cell suspension of the organ and then removing part of the suspension, the first and second portions of an organ may be interspersed with one another in the organ. In the example shown in FIG. 1B, antibody A is identified as having a biological activity. The nucleotide sequence encoding the IgH and IgL chain of the antibody is obtained. Based on these sequences, PCR primers that are specific for the heavy and light chains of antibodies that are in the same lineage group as the identified antibody are designed, and used to obtain from the second portion of the antibody producing organ the sequences of further antibodies that are in the same lineage group as the identified antibody. The further antibodies are tested, and a second antibody from the same lineage group and also having the same biological activity as the first antibody is identified.

Many exemplary aspects of this alternative method, e.g., which antigens and bioassays can be employed in the method, etc., are discussed above. In certain embodiments, a lead antibody obtained from a first portion of an antibody-producing organ is identified using a bioassay. In this embodiment, the antibodies obtained from the first portion of the organ are screened using a hybridoma-based method or by a method that does not require production of hybridomas, e.g., by phage display or by the method described in US20040067496 and other references, for example, to identify a biologically active antibody. In one embodiment, a portion of the splenocytes of a spleen of a single animal is fused with a fusion partner to produce hybridomas that are then screened to identify a biologically active antibody. In another embodiment, heavy and light chain sequences are directly amplified from PBMCs, and recombinant antibodies are expressed in a different cell (e.g., as described in US20040067496) prior to screening. In another embodiment, a phage display library is constructed from the RNA made from a portion of the spleen of an animal, and the phage display library is screened. The first, biologically active antibody is identified, and the nucleic acid encoding that antibody is sequenced.

In certain embodiments, polynucleotides encoding the variable heavy and variable light domains of lineage-related antibodies may be amplified from the same animal as the first antibody by "CDR-anchored PCR", i.e., using pairs of primers that each contains a primer that is complementary to a CDR-encoding region of the parent antibody cDNA. In these embodiments, the method may include: a) obtaining the nucleotide sequences of: i. a heavy chain-encoding nucleic acid that encodes the variable heavy chain of a first antibody of an immunized animal; and ii. a variable light chain-encoding nucleic acid that encodes the light chain of the first antibody; b) obtaining the amino acid sequence of the variable domains of the heavy and light chains of further antibodies from the immunized animal, using: i. a first primer pair that includes a first primer that is complementary to a CDR-encoding region of the heavy chain-encoding nucleic acid; and ii. a second primer pair that includes a second primer that is complementary to a CDR-encoding region of the light chain-encoding nucleic acid. After the amino acid sequences of the variable domains of the further antibodies have been determined by translation of the obtained nucleotide sequences, the amino acid may be analyzed using the above methods to confirm that they are related by lineage to the first antibody (e.g., analyzed to determine whether the amino acid sequences of the heavy and light chains are at least 80% identical to those of the parent antibody and whether the heavy and light chain CDR3 regions are of identical length of near identical sequence etc. as discussed above).

As would be readily apparent, a variety of techniques are available for amplifying sequences that encode further antibodies from an animal after the nucleotide sequence encoding a first antibody has been obtained from that animal. For example, sequences encoding the heavy and light chains of the second antibody may be amplified using inverse PCR (e.g., using two primers that face away from each other) or by anchored PCR using a specific (where a specific primer may be complementary to a different sequence of the first antibody, e.g., a different CDR sequence) or "universal" primer (where a universal primer is complementary to a sequence that is present in a plurality of different antibody-encoding polynucleotides), where one of the primers is complementary to first CDR-encoding region using cDNA as a template. In certain cases, a universal primer may be complementary to a sequence that is in at least 10% (e.g., at least 20% at least 40% at least 50% or at least 80%) of all heavy or light chain encoding cDNAs obtainable from the animal (e.g., complementary to nucleic acid encoding a conserved sequence that is present in the constant region or secretion signal of the antibodies). In other embodiments, the universal primer may be complementary to flanking sequences in the vector into which cDNA from the animal is cloned or to linkers ligated onto the cDNA, for example.

In one embodiment, two amplification reactions are performed using cDNA as a template, where the first reaction amplifies the heavy chain variable domain-encoding nucleic acid for the second antibody and the second reaction amplifies the light chain variable domain-encoding nucleic acid for the second antibody. In this embodiment: a) the first reaction uses: i. a CDR-specific primer that is complementary to a CDR-encoding region (i.e., the CDR1, CDR2 or CDR3 region) of the heavy chain-encoding nucleic acid of the first antibody and ii. a universal second primer that is complementary to a non-variable domain-encoding region of the antibody heavy chain cDNA, e.g., to a sequence that encodes the constant domain or secretion signal of the heavy chain of the first antibody, as illustrated in the examples section of this disclosure; and b) the second reaction uses i. a CDR-specific primer that is complementary to a CDR-encoding region (i.e., the CDR1, CDR2 or CDR3 region) of the light chain-encoding nucleic acid of the first antibody and ii. a universal second primer that is complementary to a non-variable domain-encoding region of the antibody light chain cDNA, e.g., to a sequence that encodes the constant domain or secretion signal of the light chain of the first antibody, as illustrated in the examples section of this disclosure.

Several strategies for cloning antibody sequences by PCR are known and may be readily adapted for use in the instant method (e.g., by using a CDR-specific primer in addition to a disclosed primer). Such strategies include those described by: LeBoeuf (*Cloning and sequencing of immunoglobulin variable-region genes using degenerate oligodeoxyribonucleotides and polymerase chain reaction.* Gene. 1989 82:371-7), Dattamajumdar (*Rapid cloning of any rearranged mouse immunoglobulin variable genes* Immunogenetics. 1996 43:141-51), Kettleborough (*Optimization of primers for cloning libraries of mouse immunoglobulin genes using the polymerase chain reaction* Eur. J. Immunol. 1993 23:206-11), Babcook (A novel strategy for generating monoclonal antibodies from single, isolated lymphocytes producing antibodies of defined specificities Proc. Natl. Acad. Sci. 1996 93: 7843-7848) and Williams (*Structural diversity in domains of the immunoglobulin superfamily*. Cold Spring Harb. Symp. Quant. Biol. 1989 54:637-47) as well as many others. In certain cases, the second primer may be a mixture of different primers or degenerate primers, for example.

The heavy chain CDR-specific primer may be complementary to the sequence that encodes the CDR1, CDR2 or CDR3 region of the heavy chain of the first antibody and, likewise, the light chain CDR-specific primer may be complementary to the sequence that encodes the CDR1, CDR2 or CDR3 region of the light chain of the first antibody. In certain embodiments, a particular CDR-specific primer may be chosen because the CDR sequence to which it binds may be known to be less variable than other CDR sequences.

Such CDR-anchored amplification method described in U.S. patent application Ser. No. 61/151,052, filed Feb. 9, 2009, which is incorporated by reference in its entirety for disclosure of those methods.

The above-described CDR-anchored method is effective because most sequence diversity between the variable domains in different families of antibodies that are related by lineage is in the CDR regions (i.e., the CDRs are quite variable between different families of antibodies), whereas the sequence of the CDR regions is relatively constant within the antibodies of a single family of antibodies that are related by lineage. Because the method uses primers that are complementary to sequence that are highly variable between different families of related antibodies, only related antibodies should be successfully amplified by the method.

In this embodiment, an amplification reaction may be performed using cDNA made from a second portion of the antibody-producing organ. For example, the amplification reaction may be done using nucleic acid obtained from single cells (or cultures of the same) or nucleic acid obtained from pooled cells (e.g., pools of different antibody-producing cells that each contain cDNA). Pools may contain cDNA from at least 10, at least 100 or at least 1,000 different antibody cells, for example. In embodiments in which hybridomas are used, the identity of the hybridomas that contributed to each pool may be tracked in order to identify a hybridoma producing a second antibody if the sequence encoding the second antibody is successfully amplified. Amplification products of the expected size may be sequenced directly or cloned and sequenced using known methods.

Depending on the antigen and number of antibody-producing cells in the second portion of the antibody-producing organ, the heavy and light chain variable sequences for at least 5, at least 10, at least 20, at least 50 or at least 100 or more, e.g., up to 200, up to 500, 1,000, 5,000 or 10,000 or more sequences may be obtained.

The further antibodies are tested in a second bioassay to identify a second antibody that has the same biological activity as the first antibody. As noted above, the first and second bioassays may be the same or different. In certain cases at least 30% (e.g., at least 70%, at least 80%, or at least 90%) of the lineage-related antibodies are tested in the bioassay. In this embodiment, the further antibodies may contain naturally paired heavy and light chain variable domains, or non-naturally paired heavy and light chains (i.e., heavy and light chain variable domains from different antibodies of the same lineage group). Since the antibodies are from the same lineage group, it is expected that such antibodies will be functional. In particular embodiments, the pairing of the heavy and light chains may be systematic (e.g., every heavy chain is tested in combination with every light chain) or random (e.g., every heavy chain is tested with randomly selected light chains), for example.

An antibody produced by the instant methods finds use in diagnostics, in antibody imaging, and in treating diseases treatable by monoclonal antibody-based therapy. In particular, an antibody humanized by the instant methods may be used for passive immunization or the removal of unwanted cells or antigens, such as by complement mediated lysis or antibody mediated cytotoxicity (ADCC), all without substantial immune reactions (e.g., anaphylactic shock) associated with many prior antibodies. For example, the antibodies of the present invention may be used as a treatment for a disease where the surface of an unwanted cell specifically expresses a protein recognized the antibody (e.g. HER2, or any other cancer-specific marker) or the antibodies may be used to neutralize an undesirable toxin, irritant or pathogen. Humanized antibodies are particularly useful for the treatment of many types of cancer, for example colon cancer, lung cancer, breast cancer prostate cancer, etc., where the cancers are associated with expression of a particular cellular marker. Since most, if not all, disease-related cells and pathogens have molecular markers that are potential targets for antibodies, many diseases are potential indications for humanized antibodies. These include autoimmune diseases where a particular type of immune cells attack self-antigens, such as insulin-dependent diabetes mellitus, systemic lupus erythematosus, pernicious anemia, allergy and rheumatoid arthritis; transplantation related immune activation, such as graft rejection and graft-vs-host disease; other immune system diseases such as septic shock; infectious diseases, such as viral infection or bacteria infection; cardiovascular diseases such as thrombosis and neurological diseases such as Alzeimer's disease.

An antibody of particular interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are termed "therapeutic" antibodies.

EXAMPLES

The following examples are provided in order to demonstrate and further illustrate certain embodiments and aspects of the present invention and are not to be construed as limiting the scope thereof.

Example 1

Method of Producing a Library of Engineered-Antibody Producing Cells

Isolation of Antibody Producing Cells

Rabbits are immunized with an antigen using a standard immunization protocol. At about 10 days after the second booster immunization, antibody titers are determined using ELISA. Two booster immunizations are usually sufficient for obtaining high antibody titers. As soon as a high titer (detectable signal at 1:100000 dilution) is observed, the rabbit is sacrificed and bone marrow cells are collected from the femur and/or other large bones. Spleen cells and peripheral blood mononuclear cells (PBMCs) are also collected and frozen in 10% DMSO/90% FBS for analysis at a later time. Very large numbers of bone marrow cells (>2 billion) are obtained from a single rabbit. After washing, clearing of debris, and red-cell lysis, the antibody producing cells, which bind to the antigen with which the rabbit was immunized, are purified using FACS. Briefly, the antigen is conjugated to a fluorescent dye and the labeled antigen is incubated with the cells obtained above. The cells are briefly rinsed to wash off any antigen non-specifically attached to the cell. After rinsing, fluorescent cells are separated from unlabeled cells using FACS. These fluorescent cells express antibodies on their surface that specifically binds to the antigen with which the animal was immunized.

RT-PCR to Obtain IgH and IgL Chain cDNA

Primer design: In rabbit, the 5' coding sequences of rabbit immunoglobulin heavy chain are primarily derived from only one gene. Antibody diversity is created by gene conversion and somatic mutation, but this does not affect the 5' end of the antibody cDNA. Thus, most rabbit IgG H chains have very similar or identical signal peptide sequences, and the same is true for L chains. On the 3' side, primers hybridizing to the constant domains, which also have identical sequences in most rabbit antibodies (rabbit constant domains are not divided into subclasses). As a result, only one pair of primers each is required for amplifying the vast majority of rabbit IgG H and L sequences. Typical priming sites are shown below, although any primer sites are used so long as the a variable domain-encoding polynucleotide is amplified. Typical primers for use with rabbit antibody-producing cells are as follows: heavy chain, 5' end (CACCATGGAGACTGGGCTGCGCTGGCTTCTCCTGGTCGCTGTG (SEQ ID NO: 181)); heavy chain, 3' end (CTCCCGCTCTCCGGGTAAATGAGCGCTGTGCCGGCGA (SEQ ID NO: 182)); light chain kappa, 5'end (CAGGCAGGACCCAGCATGGACACGAGGGCCCCCACT (SEQ ID NO: 183)); and L kappa, 3'end (TCAATAGGGGTGACTGTTAGAGCGAGACGCCTGC (SEQ ID NO: 184)).

Note that the 3' H chain primer spans the 3' end of the coding region, the stop codon, and the beginning of the 3' UTR. Thus, this primer is specific for the secreted form of IgG, and does not recognize the transmembrane form, which does not contain this sequence due to alternative splicing. Therefore, the method is unlikely to recover IgG from memory B cells, which express predominantly the transmembrane form.

RT-PCR Conditions:

Cell lysis is done heating in a buffer containing RNAse inhibitors, followed by DNA degradation and reverse transcription performed at high temperature (60° C.) using a thermostable reverse transcriptase. Reverse transcription is primed by primers specific for the 3' region of the IgG mRNAs. A single-step RT-PCR protocol is used, utilizing a thermostable enzyme that has both reverse transcriptase and DNA polymerase activities (MasterAmp™ RT-PCR Kit for High Sensitivity, Epicentre Technologies, Madison, Wis.). PCR products are analyzed by agarose gel electrophoresis. If required, a second round of PCR is performed with nested primers. In some PCR applications, this step is required to produce sufficient amounts of specific product.

Co-Amplification of H and L Chain cDNAs:

Different combinations of primers are tried, to accomplish efficient PCR amplification of H and L chain cDNAs in the same reaction. A 'head start' approach is often used, where PCR cycling is started with H chain primers alone; after a number of cycles (5 to 10) the L chain primers are added to the mix. Using these methods, similar yields of H and L chain are produced. Alternatively, a nested PCR approach is used for the H chain, by performing an initial round of PCR with primers amplifying the full-length cDNA, and a second round with primers amplifying only the vH-cH1-hinge portion of the H chain. This method should yield a product similar in size to the L chain cDNA. Expression of this product yields the F(ab')2 fragment of IgG, which is divalent and fully active for antigen-binding.

IgG heavy and light chain PCR products are joined with CMV promoter and BGH3'pA (bovine growth hormone polyadenylation/transcription termination) sequences.

Method a) Overlap Extension PCR.

CMV Promoter Segment:

To prepare the CMV promoter fragment, the expression vector pcDNA-3 (which contains the CMV promoter and BGH3'pA segments) is used as a template, and the following PCR setup:

Primer 1 (5' AATTCACATTGATTATTGAG 3'; SEQ ID NO: 185) corresponding to the 5' end of the CMV promoter;

Primer 2 (5' CAGCGCAGCCCAGTCTCCATCCC GTAAGCAGTGGGTTCTC 3'; SEQ ID NO: 186) corresponding to the 3' end of the CMV promoter, and containing a 5' extension (underlined) complementary to the 5' end of the rabbit Ig H signal peptide sequence is performed.

PCR amplification with these primers produces a linear DNA fragment consisting of the CMV promoter (610 nt) and a 20 nt extension on the 3' end, which is complementary to the 5' end of the IgG vH coding region. As mentioned above, most rabbit IgGs contain 5' vH (signal peptide) regions with nearly identical sequences. Therefore, only one primer pair is needed to amplify the majority of rabbit IgG cDNAs.

BGH3'pA Segment.

A similar approach is used to prepare the BGH3'pA segment. Again, the pcDNA3 expression vector is used as a template, and the following primers are used:

Primer 3 (5' CCGGGTAAATGAGCGCTGTGGTT-TAAACCCGCTGATCAGC 3'; SEQ ID NO: 187), corresponding to 5' end of the BGH3'pA domain extended by a 20 nt sequence complementary to the 3' end of the IgG heavy chain coding region, and including 11 nt of the 3' untranslated domain.

Primer 4 (5' AAGCCATAGAGCCGACCGCA 3'; SEQ ID NO: 188) corresponding to the 3' end of the BGH polyadenylation domain.

PCR amplification results in a 250 nt fragment containing the BGH3'pA sequence and a 20 nt extension that overlaps with the 3' end of the IgG heavy chain sequence.

Overlay Extension PCR:

The IgG heavy chain PCR product are mixed with the CMV promoter and BGH3'pA segments. The mixture is subjected to 10 cycles of PCR. The overlapping segments anneal, followed by extension of the overlapping 3' ends. At the end of the 10 cycles, the outside primers (primers 1 and 4) are added to the mixture, and another 30 cycles of PCR are performed. The product is a 2100 nt fragment consisting of the CMV promoter, the IgG H coding sequence, and the BGH terminator.

IgG Light Chain:

The process are carried out in an analogous manner to produce 1500 nt fragments consisting of CMV promoter, kappa light chain coding sequence, and BGH terminator. A separate set of primers for lambda light chains can also be used to amplify and clone lambda light chains.

A low concentration of primers in the initial PCR reaction may be used. In some embodiments, primers are be designed such that amplification of the heavy chain results in a nucleotide encoding a form of the IgG H chain that is truncated at the 3' end of the hinge domain. This fragment would be similar in size to the v kappa light chain. Co-expression of these fragments results in the secretion of F (ab')$_2$ fragments of IgG.

Method b) Topoisomerase I Coupling.

This method is used as an alternative to overlap extension PCR. The overall experimental strategy is as described above. Commercially available topoisomerase-modified CMV promoter and BGH3'pA segments will be used (Invitrogen, San Diego, Calif.). The CMV promoter element (610 nt) is provided in a modified form with the topoisomerase recognition site (CCCTT) at its 3' end, and a six base pair single-stranded overhang at the 3' end (GCCTTG) which is used for directional coupling with the PCR product. The topoisomerase I enzyme is bound to the recognition site CCCTT. In order to be joined to the Topo-modified CMV promoter, the PCR product needs to contain the sequence CGGAACAAGGG (SEQ ID NO: 189) at its 5'end. This sequence is cleaved by topoisomerase, resulting in a 6-base single-strand overhang that is complementary to the single-strand overhang of the CMV promoter element. These overhangs anneal and the fragments are covalently joined by the enzyme.

In order to link the IgG cDNA fragment to the CMV promoter, the 5' primer used in the last round of IgG amplification are extended at its 5' end with the sequence CGGAACAAGGG (SEQ ID NO: 190).

The linkage of the 3' end of the IgG fragment with the BGH3'pA element is performed in an analogous manner, except that a different single-stranded overhang (GACTCA) is being used. This provides for directionality and selective joining of the 5' end with the CMV promoter and the 3' with the BGH terminator.

The joining reaction is carried out by mixing the 5' CMV element, IgG PCR product, and 3'BGH element at a 1:2:1 ratio, and adding the 10× reaction buffer. The reaction proceeds rapidly and is usually complete within 10 min at room temperature. Following the reaction, a secondary PCR reaction is carried out, using primers corresponding to the 5' end of the CMV promoter and the 3' end of the BGH terminator (primers 1 and 4, see above). This results in the formation of the 2.1 kb IgG H expression cassette, or the 1.5 kb IgG L expression cassette. Conditions for co-production of H and L IgG expression cassettes in the same reaction are also envisioned.

The IgG H expression cassettes are cloned into a vector carrying a hygromycin resistance marker to generate an IgG H expression cassette library. The IgG L expression cassettes are cloned into a vector carrying a G418 resistance marker to generate an IgG L expression cassette library.

Equimolar amounts of the IgG H and IgG L expression cassette libraries are mixed and transfected into CHO cells. The transfected CHO cells are plated into 96-well or 384-well microtiter plates such that each well contains approximately one cell. Cells are maintained in media containing both hygromycin and G418. Cells that survive the double selection contain at least one expression cassette pair.

These cells are cultured and the antibodies produced by these cells are tested for binding to the antigen with which the rabbit was immunized.

Example 2

Related Antibodies

Antibodies were obtained from rabbit hybridoma cells producing anti-KDR antibodies that block the interaction of VEGF with its receptor (KDR). The hybridoma cells were generated by fusing immunized rabbit splenocytes with the rabbit hybridoma fusion partner 240E-W2.

New Zealand white rabbits were immunized with a fusion protein containing the rabbit Fc region and the extracellular domain of KDR. Each rabbit received a primary immunization by subcutaneous injection of 0.4 mg of the purified protein with complete Freund's or TiterMax adjuvant. The animals were then boosted by subcutaneous injection of 0.2 mg of the protein with incomplete Freund's or TiterMax once every three weeks. The final boost (0.4 mg protein in saline) was given intravenously 4 days before splenectomy.

Cell fusions were performed following the conventional protocol of Spieker-Polet using PEG. The ratio of splenocytes to the fusion partner was 2:1. The fused cells were plated in 96-well plates and HAT was added after 48 hrs to select for hybridomas. Direct ELISA was performed to identify antibodies that block binding of VEGF to a KDR fusion protein coated onto a microtiter plate. In this assay, the Fc-KDR ECD fusion protein was coated onto a 96-well ELISA plate and goat anti-rabbit IgG FEB conjugated to alkaline phosphatase was used to detect antibody binding to KDR. Antibodies identified in this assay were then were screened for blocking VEGF interaction with KDR in a ligand-receptor assay. The blocking antibodies were identified by their inhibition of binding of VEGF in solution to KDR coated on plates.

cDNAs coding the heavy and light chains of the antibodies were cloned and sequenced. The polypeptides encoded by the cDNAs were aligned and this alignment is shown in FIG. 2. FIG. 2 shows that two groups of related anti-KDR rabbit monoclonal Abs were obtained. Antibodies 69, 6, 71, 43, 81, 4, 30, 54, 57, 50, 68, 56, 83, 36, 77, 95, 14, 42, 27 belong to one group. Antibodies 2, 17, 3, 6, 9 belong to a different group.

FIG. 3 is a multiple sequence alignment of the H3 region of ten rabbit antibody sequences extracted from the Kabat database to illustrate the expected variation in unrelated antibodies.

Example 3

CDR-Anchored Amplification of Polynucleotides Encoding Related Antibodies

Several examples illustrating a method by which the amino acid sequences of related rabbit antibodies may be obtained by PCR are set forth in FIGS. 4A-4H. In the examples shown in FIGS. 4A-4D, reverse primers that are complementary to the CDR3 regions of the light chain of antibodies 31 (FIG. 4A), 29 (FIG. 4b), 27 (FIG. 4c) and 20 (FIG. 4d) were designed and can be used along with a universal forward primer (SEQ ID NO: 118) that binds to a site that is present in all rabbit antibody heavy chain sequences to amplify coding sequences for related antibodies. In the example shown in FIG. 4A, the primers designed against sequences that encode antibody 31 are expected to amplify light chain variable domain sequences for antibodies 11, 12, 2, 25, 22, 27, 3, 1, 19, 24, 23, 18, 13, 10 and 21, which are all from the same animal as antibody 31 and are related to antibody 31 by lineage. In the example shown in FIG. 4B, the primers designed against sequences that encode antibody 29 are expected to amplify light chain variable domain sequences for antibodies 8, 9, 16 and 32, which are all from the same animal as antibody 29 and are related to antibody 29 by lineage. In the example shown in FIG. 4C, the primers designed against sequences that encode antibody 27 are expected to amplify light chain variable domain sequences for other antibodies which are all from the same animal as antibody 27 and are related to antibody 27 by lineage. In the example shown in FIG. 4D, the primers designed against sequences that encode antibody 20 are expected to amplify light chain variable domain sequences for other antibodies which are all from the same animal as antibody 20 and are related to antibody 20 by lineage.

In the examples shown in FIGS. 4E-4H, reverse primers that are complementary to the CDR3 regions of the heavy chain of antibodies 31 (FIG. 4E), 29 (FIG. 4F), 29 (FIG. 4G) and 21 (FIG. 4H) were designed and can be used along with a universal forward primer (SEQ ID NO: 148) that binds to a site that is present in all rabbit antibody heavy chain sequences to amplify coding sequences for related antibodies. In the example shown in FIG. 4E, the primers designed against sequences that encode antibody 31 are expected to amplify heavy chain variable domain sequences for antibodies 2, 17, 22, 25, 12, 1, 24, 19, 25, 11, 31, 3, 10, 13, 21, 18 and 23, which are all from the same animal as antibody 31 and are related to antibody 31 by lineage. In the example shown in FIG. 4F, the primers designed against sequences that encode antibody 29 are expected to amplify heavy chain variable domain sequences for antibodies 8, 9, 16 and 32, which are all from the same animal as antibody 29 and are related to antibody 29 by lineage. In the example shown in FIG. 4G, the primers designed against sequences that encode antibody 27 are expected to amplify heavy chain variable domain sequences for other antibodies which are all from the same animal as antibody 27 and are related to antibody 27 by lineage. In the example shown in FIG. 4H, the primers designed against sequences that encode antibody 20 are expected to amplify heavy chain variable domain sequences for other antibodies which are all from the same animal as antibody 20 and are related to antibody 20 by lineage.

SEQUENCE LISTING

```
<160> NUMBER OF SEQ ID NOS: 190

<210> SEQ ID NO 1
<211> LENGTH: 119
<212> TYPE: PRT
<213> ORGANISM: Oryctolagus cuniculus

<400> SEQUENCE: 1

Gln Ser Val Glu Glu Ser Gly Gly Arg Leu Val Thr Pro Gly Thr Pro
 1               5                  10                  15

Leu Thr Leu Thr Cys Thr Val Ser Gly Ile Asp Leu Ser Ser Tyr Ala
            20                  25                  30
```

Met Ser Trp Val Arg Gln Ala Pro Gly Lys Gly Leu Glu Trp Val Gly
        35                  40                  45

Ile Ile Arg Gly Ser Gly Ser Ile Tyr Tyr Ala Asn Trp Ala Lys Gly
50                  55                  60

Arg Phe Thr Ile Ser Lys Thr Ser Thr Thr Val Asp Leu Arg Phe Ala
65                  70                  75                  80

Ser Pro Thr Thr Glu Asp Thr Ala Thr Tyr Phe Cys Ala Arg Val Leu
                85                  90                  95

Trp Pro Gly Ser Val Ala Tyr Ala Tyr His Asn Ile Trp Gly Pro Gly
                100                 105                 110

Thr Leu Val Thr Val Ser Ser
        115

<210> SEQ ID NO 2
<211> LENGTH: 119
<212> TYPE: PRT
<213> ORGANISM: Oryctolagus cuniculus

<400> SEQUENCE: 2

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Tyr Ala
                20                  25                  30

Met Ser Trp Phe Arg Gln Ala Pro Gly Lys Gly Leu Glu Trp Ile Gly
        35                  40                  45

Leu Ile Arg Arg Ser Gly Ala Thr Tyr Tyr Ala Ser Trp Ala Lys Gly
50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
                100                 105                 110

Thr Leu Val Thr Val Ser Ser
        115

<210> SEQ ID NO 3
<211> LENGTH: 119
<212> TYPE: PRT
<213> ORGANISM: Oryctolagus cuniculus

<400> SEQUENCE: 3

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Asn Tyr Ala
                20                  25                  30

Met Ser Trp Phe Arg Gln Ala Pro Gly Lys Gly Leu Glu Trp Ile Gly
        35                  40                  45

Leu Ile Arg Ser Ser Gly Ala Thr Tyr Tyr Ala Ser Trp Ala Lys Gly
50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
                100                 105                 110

Thr Leu Val Thr Val Ser Ala
        115

<210> SEQ ID NO 4
<211> LENGTH: 119
<212> TYPE: PRT
<213> ORGANISM: Oryctolagus cuniculus

<400> SEQUENCE: 4

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Phe Arg Gln Ala Pro Gly Lys Gly Leu Glu Trp Ile Gly
        35                  40                  45

Leu Ile Arg Ser Ser Gly Ala Thr Tyr Tyr Ala Ser Trp Ala Lys Gly
    50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 5
<211> LENGTH: 119
<212> TYPE: PRT
<213> ORGANISM: Oryctolagus cuniculus

<400> SEQUENCE: 5

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Ser Trp Phe Arg Gln Ala Pro Gly Lys Gly Leu Glu Trp Ile Gly
        35                  40                  45

Leu Ile Arg Ser Ser Gly Ala Thr Tyr Tyr Ala Ser Trp Ala Lys Gly
    50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 6
<211> LENGTH: 119
<212> TYPE: PRT
<213> ORGANISM: Oryctolagus cuniculus

<400> SEQUENCE: 6

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Ser Trp Phe Arg Gln Ala Pro Gly Lys Gly Leu Glu Trp Ile Gly
            35                  40                  45

Leu Ile Arg Ser Ser Gly Ala Thr Tyr Tyr Ala Ser Trp Ala Lys Gly
        50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Ser Leu Val Thr Val Ser Ser
            115

<210> SEQ ID NO 7
<211> LENGTH: 119
<212> TYPE: PRT
<213> ORGANISM: Oryctolagus cuniculus

<400> SEQUENCE: 7

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Phe Arg Gln Ala Pro Gly Lys Gly Leu Glu Trp Ile Gly
            35                  40                  45

Leu Ile Arg Ser Ser Gly Ala Thr Tyr Tyr Ala Ser Trp Ala Lys Gly
        50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
            115

<210> SEQ ID NO 8
<211> LENGTH: 119
<212> TYPE: PRT
<213> ORGANISM: Oryctolagus cuniculus

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Phe Arg Gln Ala Pro Gly Lys Gly Leu Glu Trp Ile Gly
            35                  40                  45

Leu Ile Arg Ser Ser Gly Ala Thr Tyr Tyr Ala Ser Trp Ala Lys Gly
        50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 9
<211> LENGTH: 119
<212> TYPE: PRT
<213> ORGANISM: Oryctolagus cuniculus

<400> SEQUENCE: 9

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Phe Arg Gln Ala Pro Gly Lys Gly Leu Glu Trp Ile Gly
        35                  40                  45

Leu Ile Arg Ser Ser Gly Ala Thr Tyr Tyr Ala Ser Trp Ala Lys Gly
    50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 10
<211> LENGTH: 119
<212> TYPE: PRT
<213> ORGANISM: Oryctolagus cuniculus

<400> SEQUENCE: 10

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Phe Arg Gln Ala Pro Gly Lys Gly Leu Glu Trp Ile Gly
        35                  40                  45

Leu Ile Arg Ser Ser Gly Ala Thr Tyr Asp Ala Pro Trp Ala Lys Gly
    50                  55                  60

Arg Phe Thr Ile Ser Lys Ala Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 11
<211> LENGTH: 119
<212> TYPE: PRT
<213> ORGANISM: Oryctolagus cuniculus

<400> SEQUENCE: 11

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Phe Arg Gln Ala Pro Gly Lys Gly Leu Glu Trp Ile Gly
            35                  40                  45

Leu Ile Arg Ser Gly Gly Ala Thr Tyr Tyr Ala Ser Trp Ala Lys Gly
        50                  55                  60

Arg Phe Thr Ile Ser Lys Val Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 12
<211> LENGTH: 119
<212> TYPE: PRT
<213> ORGANISM: Oryctolagus cuniculus

<400> SEQUENCE: 12

Gln Ser Leu Glu Glu Ser Gly Gly Arg Leu Val Thr Pro Gly Thr Pro
1               5                   10                  15

Leu Thr Leu Thr Cys Ala Val Ser Gly Ile Asp Leu Ser Ser Tyr Ala
            20                  25                  30

Met Ser Trp Phe Arg Gln Ala Pro Gly Lys Gly Leu Glu Trp Ile Gly
            35                  40                  45

Leu Ile Arg Ser Ser Gly Ala Thr Tyr Tyr Ala Ser Trp Ala Lys Gly
        50                  55                  60

Arg Phe Thr Ile Ser Lys Ala Ser Thr Thr Val Asp Leu Lys Met Thr
65                  70                  75                  80

Ser Leu Thr Thr Glu Asp Thr Ala Thr Tyr Phe Cys Ala Arg Val Leu
                85                  90                  95

Trp Pro Gly Asp Ile Ala Tyr Ala Tyr His Asn Ile Trp Gly Pro Gly
            100                 105                 110

Thr Leu Val Thr Val Ser Ser
        115

<210> SEQ ID NO 13
<211> LENGTH: 119
<212> TYPE: PRT
<213> ORGANISM: Oryctolagus cuniculus

<400> SEQUENCE: 13

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ala Tyr Ala
            20                  25                  30

Met Ser Trp Val Arg Gln Ala Pro Gly Lys Gly Leu Glu Trp Ile Gly
            35                  40                  45

Leu Ile Arg Ser Ser Gly Ala Thr Tyr Tyr Ala Ser Trp Ala Lys Gly
        50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Val Leu
                85                  90                  95

Trp Pro Gly Glu Ile Ala Tyr Ala Tyr His Asn Ile Trp Gly Pro Gly
            100                 105                 110

Thr Leu Val Thr Val Ser Ser
        115

<210> SEQ ID NO 14
<211> LENGTH: 119
<212> TYPE: PRT
<213> ORGANISM: Oryctolagus cuniculus

<400> SEQUENCE: 14

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Asn Tyr Ala
            20                  25                  30

Met Ser Trp Val Arg Gln Ala Pro Gly Lys Gly Leu Glu Trp Ile Gly
        35                  40                  45

Ile Ile Gly Ser Ser Gly Ser Ile Phe Tyr Ala Ser Trp Ala Lys Gly
    50                  55                  60

Arg Ile Thr Ile Ser Lys Thr Ser Thr Thr Val Asp Leu Lys Phe Thr
65                  70                  75                  80

Ser Leu Thr Thr Glu Asp Thr Ala Thr Tyr Phe Cys Ala Arg Val Leu
                85                  90                  95

Trp Ala Gly Ser Val Ala Tyr Ala Tyr His Asn Ile Trp Gly Pro Gly
            100                 105                 110

Thr Leu Val Thr Val Ser Ser
        115

<210> SEQ ID NO 15
<211> LENGTH: 119
<212> TYPE: PRT
<213> ORGANISM: Oryctolagus cuniculus

<400> SEQUENCE: 15

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Ser Ser Gly Asn Thr Tyr Phe Ala Ser Trp Ala Lys Gly
    50                  55                  60

Arg Phe Thr Ile Ser Lys Thr Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Ala Gly Ser Val Ala Tyr Ala Tyr His Asn Ile Trp Gly Pro Gly
            100                 105                 110

Thr Leu Val Thr Val Ser Ser
        115

<210> SEQ ID NO 16
<211> LENGTH: 119
<212> TYPE: PRT
<213> ORGANISM: Oryctolagus cuniculus

<400> SEQUENCE: 16

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
            35                  40                  45

Ile Ile Arg Pro Gly Gly Asn Thr Tyr Ser Ala Ser Trp Ala Lys Gly
 50                  55                  60

Arg Phe Thr Ile Ser Lys Thr Ser Thr Thr Val Asp Leu Lys Phe Thr
65                  70                  75                  80

Ser Pro Thr Pro Glu Asp Thr Ala Thr Tyr Phe Cys Ala Arg Val Leu
                85                  90                  95

Trp Ala Gly Asp Val Ala Tyr Ala Tyr His Asn Ile Trp Gly Pro Gly
            100                 105                 110

Thr Leu Val Thr Val Ser Ser
            115

<210> SEQ ID NO 17
<211> LENGTH: 119
<212> TYPE: PRT
<213> ORGANISM: Oryctolagus cuniculus

<400> SEQUENCE: 17

Gln Ser Val Glu Glu Ser Gly Gly Arg Leu Val Thr Pro Gly Thr Pro
 1               5                   10                  15

Leu Thr Leu Thr Cys Thr Val Ser Gly Phe Ser Leu Ser Asp Tyr Ala
            20                  25                  30

Met Ser Trp Val Arg Gln Ala Pro Gly Lys Gly Leu Glu Trp Ile Gly
            35                  40                  45

Met Val Arg Asp Thr Gly Val Thr Phe Tyr Ala Gly Trp Ala Lys Gly
 50                  55                  60

Arg Phe Thr Ile Ser Lys Thr Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Ala Gly Tyr Val Ala Tyr Ala Tyr His Asn Ile Trp Gly Pro Gly
            100                 105                 110

Thr Leu Val Thr Val Ser Ser
            115

<210> SEQ ID NO 18
<211> LENGTH: 119
<212> TYPE: PRT
<213> ORGANISM: Oryctolagus cuniculus

<400> SEQUENCE: 18

Gln Ser Val Glu Glu Ser Gly Gly Arg Leu Val Thr Pro Gly Thr Pro
 1               5                   10                  15

Leu Thr Leu Thr Cys Thr Ala Ser Gly Phe Ser Leu Ser Asp Tyr Ala
            20                  25                  30

Met Ser Trp Val Arg Gln Ala Pro Gly Lys Gly Leu Glu Trp Ile Gly
            35                  40                  45

Ile Ile Ser Asn Ser Gly Ile Thr Phe Tyr Ala Gly Trp Ala Lys Gly
 50                  55                  60

Arg Phe Thr Ile Ser Lys Thr Ser Thr Thr Val Asp Leu Lys Phe Thr
65                  70                  75                  80

Ser Pro Thr Thr Glu Asp Thr Ala Thr Tyr Phe Cys Ala Arg Ala Leu
                85                  90                  95

Trp Ala Gly Tyr Ile Ala Tyr Val Tyr His Asn Ile Trp Gly Pro Gly
            100                 105                 110

```
Thr Leu Val Thr Val Ser Ser
        115

<210> SEQ ID NO 19
<211> LENGTH: 119
<212> TYPE: PRT
<213> ORGANISM: Oryctolagus cuniculus

<400> SEQUENCE: 19

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ala Leu Asn Asp Phe Ala
            20                  25                  30

Met Ser Trp Val Arg Gln Ala Pro Gly Lys Gly Leu Glu Trp Ile Gly
        35                  40                  45

Met Ile Ala Ser Ser Gly Asn Thr Phe Tyr Ala Ser Trp Ala Lys Gly
    50                  55                  60

Arg Phe Thr Ile Ser Lys Thr Ser Thr Thr Val Asp Leu Lys Phe Thr
65                  70                  75                  80

Ser Pro Thr Thr Glu Asp Thr Ala Thr Tyr Phe Cys Ala Arg Val Leu
                85                  90                  95

Trp Pro Gly Tyr Ile Ala Tyr Ala Tyr His Asn Ile Trp Gly Pro Gly
            100                 105                 110

Thr Leu Val Thr Val Ser Ser
        115

<210> SEQ ID NO 20
<211> LENGTH: 116
<212> TYPE: PRT
<213> ORGANISM: Oryctolagus cuniculus

<400> SEQUENCE: 20

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu His Ile Gly
        35                  40                  45

Ile Ile Thr Ala Ser Gly Gly Ile Tyr Tyr Ala Ser Trp Ala Lys Gly
    50                  55                  60

Arg Phe Thr Ile Ser Lys Thr Ser Thr Thr Val Asp Leu Arg Ile Pro
65                  70                  75                  80

Ser Pro Thr Thr Glu Asp Thr Gly Thr Tyr Phe Cys Ala Arg Thr Glu
                85                  90                  95

Asn Ser Tyr Phe Leu Tyr Phe Thr Ile Trp Gly Pro Gly Thr Leu Val
            100                 105                 110

Thr Val Ser Ser
        115

<210> SEQ ID NO 21
<211> LENGTH: 119
<212> TYPE: PRT
<213> ORGANISM: Oryctolagus cuniculus

<400> SEQUENCE: 21

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30
```

```
Met Gly Trp Val Arg Gln Ala Pro Gly Lys Gly Leu Glu Trp Ile Gly
        35                  40                  45

Phe Ile Ser Ser Ser Gly Ser Thr Tyr Tyr Ala Ser Trp Ala Lys Gly
50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Asn Asn Tyr
                85                  90                  95

Asp Asp Tyr Gly Asp Phe Leu His Tyr Phe Asn Ile Trp Gly Pro Gly
                100                 105                 110

Thr Leu Val Thr Val Ser Ser
        115
```

<210> SEQ ID NO 22
<211> LENGTH: 110
<212> TYPE: PRT
<213> ORGANISM: Oryctolagus cuniculus

<400> SEQUENCE: 22

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
                20                  25                  30

Met Ala Trp Val Arg Gln Ala Pro Gly Lys Gly Leu Glu Trp Ile Gly
        35                  40                  45

Ile Ile Asp Gly Asp Val Ser Pro Tyr Tyr Ala Ser Trp Ala Lys Gly
50                  55                  60

Arg Phe Thr Ile Ser Lys Thr Ser Ser Thr Val Asp Leu Lys Met
65                  70                  75                  80

Thr Ser Leu Thr Thr Glu Asp Thr Ala Thr Tyr Phe Cys Ala Arg Pro
                85                  90                  95

Phe Asn Ile Trp Gly Pro Gly Thr Leu Val Thr Val Ser Ser
                100                 105                 110
```

<210> SEQ ID NO 23
<211> LENGTH: 116
<212> TYPE: PRT
<213> ORGANISM: Oryctolagus cuniculus

<400> SEQUENCE: 23

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Lys Asn Ala
                20                  25                  30

Ile Ser Trp Val Arg Gln Val Pro Gly Glu Gly Leu Glu Trp Ile Gly
        35                  40                  45

Ile Ile Tyr Gly Asp Gly Asn Arg Asp Tyr Ala Asn Trp Ala Lys Gly
50                  55                  60

Arg Phe Thr Ile Ser Lys Thr Ser Thr Thr Val Asp Leu Lys Val Thr
65                  70                  75                  80

Ser Pro Thr Thr Glu Asp Thr Ala Thr Tyr Phe Cys Ala Arg Gly Thr
                85                  90                  95

Thr Ile Trp Ser Asp Tyr Leu Asp Ile Trp Gly Pro Gly Thr Leu Val
                100                 105                 110

Thr Ile Ser Ser
        115
```

<210> SEQ ID NO 24
<211> LENGTH: 119
<212> TYPE: PRT
<213> ORGANISM: Oryctolagus cuniculus

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Ser Ser Gly Ser Thr Tyr Tyr Ala Thr Trp Val Lys Gly
    50                  55                  60

Arg Phe Thr Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Gly Asp
                85                  90                  95

Asp Asp Val Ser Asp Tyr Phe Tyr Tyr Phe Pro Ile Trp Gly Pro Gly
            100                 105                 110

Thr Leu Val Thr Val Ser Ser
        115

<210> SEQ ID NO 25
<211> LENGTH: 119
<212> TYPE: PRT
<213> ORGANISM: Oryctolagus cuniculus

<400> SEQUENCE: 25

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Ser Ser Gly Ser Thr Tyr Tyr Ala Thr Trp Val Lys Gly
    50                  55                  60

Arg Phe Thr Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Gly Asp
                85                  90                  95

Asp Asp Val Ser Asp Tyr Phe Tyr Tyr Phe Pro Ile Trp Gly Pro Gly
            100                 105                 110

Thr Leu Val Thr Val Ser Ser
        115

<210> SEQ ID NO 26
<211> LENGTH: 119
<212> TYPE: PRT
<213> ORGANISM: Oryctolagus cuniculus

<400> SEQUENCE: 26

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

```
Thr Ile Ser Ser Ser Gly Ser Thr Tyr Tyr Ala Thr Trp Val Lys Gly
        50                  55                  60

Arg Phe Thr Ile Ser Lys Thr Ser Thr Thr Val Asp Leu Lys Met Thr
65                      70                  75                  80

Ser Leu Thr Ala Ala Asp Thr Ala Thr Tyr Phe Cys Ala Arg Gly Asp
                85                  90                  95

Asp Asp Val Ser Asp Tyr Phe Tyr Tyr Phe Pro Ile Trp Gly Pro Gly
                100                 105                 110

Thr Leu Val Thr Val Ser Ser
        115

<210> SEQ ID NO 27
<211> LENGTH: 119
<212> TYPE: PRT
<213> ORGANISM: Oryctolagus cuniculus

<400> SEQUENCE: 27

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Ser Ser Gly Ser Thr Tyr Tyr Ala Thr Trp Val Lys Gly
        50                  55                  60

Arg Phe Thr Ile Ser Lys Thr Ser Thr Thr Val Asp Leu Lys Met Thr
65                      70                  75                  80

Ser Leu Thr Ala Ala Asp Thr Ala Thr Tyr Phe Cys Ala Arg Gly Asp
                85                  90                  95

Asp Asp Val Ser Asp Tyr Phe Tyr Tyr Phe Pro Ile Trp Gly Pro Gly
                100                 105                 110

Thr Leu Val Thr Val Ser Ser
        115

<210> SEQ ID NO 28
<211> LENGTH: 119
<212> TYPE: PRT
<213> ORGANISM: Oryctolagus cuniculus

<400> SEQUENCE: 28

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Ser Ser Gly Ser Thr Tyr Tyr Ala Thr Trp Val Lys Gly
        50                  55                  60

Arg Phe Thr Ile Ser Lys Thr Ser Thr Thr Val Asp Leu Lys Met Thr
65                      70                  75                  80

Ser Leu Thr Ala Ala Asp Thr Ala Thr Tyr Phe Cys Ala Arg Gly Asp
                85                  90                  95

Asp Asp Val Ser Asp Tyr Phe Tyr Tyr Phe Pro Ile Trp Gly Pro Gly
                100                 105                 110

Thr Leu Val Thr Val Ser Ser
        115
```

-continued

<210> SEQ ID NO 29
<211> LENGTH: 117
<212> TYPE: PRT
<213> ORGANISM: Oryctolagus cuniculus

<400> SEQUENCE: 29

Gln Ser Leu Glu Glu Ser Gly Gly Arg Leu Val Thr Pro Gly Gly Ser
1               5                   10                  15

Leu Thr Leu Thr Cys Thr Ala Ser Gly Phe Ser Leu Ser Tyr Trp
            20                  25                  30

Met Ser Trp Val Arg Gln Ala Pro Gly Lys Gly Leu Glu Trp Ile Gly
        35                  40                  45

Ala Val Ser Asn Ser Gly Thr Thr Tyr Tyr Ala Ser Trp Ala Lys Gly
    50                  55                  60

Arg Phe Thr Ile Ser Arg Thr Ser Thr Thr Val Asp Leu Arg Met Thr
65                  70                  75                  80

Arg Leu Thr Thr Glu Asp Thr Ala Thr Tyr Phe Cys Ala Arg Asp Ala
                85                  90                  95

Gly Asp Asn Tyr Phe Thr Trp Leu Asp Leu Trp Gly Gln Gly Thr Leu
            100                 105                 110

Val Thr Val Ser Ser
        115

<210> SEQ ID NO 30
<211> LENGTH: 121
<212> TYPE: PRT
<213> ORGANISM: Oryctolagus cuniculus

<400> SEQUENCE: 30

Glu Glu Gln Leu Lys Glu Ser Gly Gly Asp Leu Val Lys Pro Glu Gly
1               5                   10                  15

Ser Leu Thr Leu Thr Cys Lys Ala Ser Gly Phe Asp Leu Ser Ser Glu
            20                  25                  30

Phe Tyr Ile Cys Trp Val Arg Gln Ala Pro Gly Lys Gly Leu Glu Trp
        35                  40                  45

Ile Gly Cys Ile Ala Thr Val Ser Ser Arg Arg Leu Tyr Ala Ser Trp
    50                  55                  60

Val Asn Gly Arg Phe Thr Ile Ser Lys Thr Ser Ser Thr Thr Val Thr
65                  70                  75                  80

Leu Gln Met Pro Ser Leu Thr Ala Ala Asp Thr Ala Thr Tyr Phe Cys
                85                  90                  95

Ala Arg Asp Asp Ser Ala Arg Asn Trp Phe Tyr Phe Tyr Leu Trp Gly
            100                 105                 110

Pro Gly Thr Leu Val Thr Val Ser Ser
        115                 120

<210> SEQ ID NO 31
<211> LENGTH: 118
<212> TYPE: PRT
<213> ORGANISM: Oryctolagus cuniculus

<400> SEQUENCE: 31

Gln Ser Leu Glu Glu Ser Gly Gly Asp Leu Val Lys Pro Gly Thr Ser
1               5                   10                  15

Leu Thr Leu Thr Cys Thr Ala Ser Gly Phe Ser Phe Ser Ala Arg His
            20                  25                  30

Phe Met Tyr Trp Val Arg Gln Ala Pro Gly Lys Gly Leu Glu Trp Ile
        35                  40                  45

```
Gly Cys Ile Asp Ile Gly Ser Gly Ser Thr Tyr Tyr Thr Ser Trp Ala
         50                  55                  60

Lys Asp Arg Phe Thr Ile Ser Lys Pro Ser Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Ser Ser Gly Tyr Pro Tyr Tyr Phe Thr Leu Trp Gly Pro Gly Thr
             100                 105                 110

Leu Val Thr Val Ser Ser
            115
```

<210> SEQ ID NO 32
<211> LENGTH: 122
<212> TYPE: PRT
<213> ORGANISM: Oryctolagus cuniculus

<400> SEQUENCE: 32

```
Gln Gln Gln Leu Val Glu Ser Gly Gly Gly Leu Val Lys Pro Gly Ala
 1               5                  10                  15

Ser Leu Thr Leu Thr Cys Lys Ala Ser Gly Phe Pro Val Thr His Trp
             20                  25                  30

Trp Met Cys Trp Val Arg Gln Ala Pro Arg Lys Gly Leu Glu Leu Ile
         35                  40                  45

Ala Cys Ala Tyr Thr Gly Asp Leu Thr Thr Tyr His Ala Ser Trp Ala
     50                  55                  60

Ile Gly Arg Phe Thr Ile Ser Thr Ser Ser Thr Met Val Thr Leu
 65                  70                  75                  80

Gln Met Thr Ser Leu Thr Val Ala Asp Thr Ala Thr Tyr Phe Cys Ala
                 85                  90                  95

Thr Trp Gly Ala His Asn Gln Gly Tyr Trp Asp Gly Phe Asp Pro Trp
             100                 105                 110

Gly Pro Gly Thr Leu Val Thr Val Ser Ser
            115                 120
```

<210> SEQ ID NO 33
<211> LENGTH: 122
<212> TYPE: PRT
<213> ORGANISM: Oryctolagus cuniculus

<400> SEQUENCE: 33

```
Gln Glu Gln Leu Val Glu Ser Gly Gly Asp Leu Val Gln Pro Glu Gly
 1               5                  10                  15

Ser Leu Thr Leu Thr Cys Lys Ala Ser Gly Leu Asp Phe Ser Ser Ser
             20                  25                  30

Tyr Trp Ile Cys Trp Val Arg Gln Ala Pro Gly Lys Gly Leu Glu Leu
         35                  40                  45

Ile Ala Cys Ile Tyr Thr Asp Ser Gly Gly Ile Trp Tyr Thr Ser Trp
     50                  55                  60

Ala Lys Gly Arg Phe Thr Ile Ser Arg Ser Thr Ser Leu Asn Thr Val
 65                  70                  75                  80

Asp Leu Lys Val Ser Ser Leu Thr Ala Ala Asp Thr Ala Thr Tyr Phe
                 85                  90                  95

Cys Ala Arg Asn Tyr Ala Gly Tyr Ser Ser Gly Ile Phe Asn Leu Trp
             100                 105                 110

Gly Pro Gly Thr Leu Val Thr Val Ser Ser
            115                 120
```

-continued

<210> SEQ ID NO 34
<211> LENGTH: 125
<212> TYPE: PRT
<213> ORGANISM: Oryctolagus cuniculus

<400> SEQUENCE: 34

Gln Glu Gln Leu Glu Glu Ser Gly Gly Gly Leu Val Lys Pro Glu Gly
1               5                   10                  15

Ser Leu Thr Leu Thr Cys Thr Ala Ser Gly Phe Ser Phe Ile Ser Asn
            20                  25                  30

Tyr Trp Met Cys Trp Val Arg Gln Ala Pro Gly Lys Gly Leu Glu Trp
        35                  40                  45

Ile Ala Cys Ile Tyr Ala Gly Gly Ile Ser Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asn Thr Ala Thr Tyr Phe
                85                  90                  95

Cys Ala Arg Ala Tyr Val Tyr Ser Gly Ala Tyr Leu Tyr Tyr Gly Met
            100                 105                 110

Asp Leu Trp Gly Pro Gly Thr Leu Val Thr Val Ser Ser
        115                 120                 125

<210> SEQ ID NO 35
<211> LENGTH: 122
<212> TYPE: PRT
<213> ORGANISM: Oryctolagus cuniculus

<400> SEQUENCE: 35

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Ala Ser Ser Ser Tyr
            20                  25                  30

Trp Met Cys Trp Val Arg Gln Ala Pro Gly Lys Gly Leu Glu Leu Ile
        35                  40                  45

Ala Cys Thr Tyr Ser Ser Ser Gly Asn Thr Asn Tyr Ala Ser Trp Ala
    50                  55                  60

Lys Gly Arg Phe Thr Ser Ser Ile Thr Ser Thr Val Thr Leu
65                  70                  75                  80

Gln Met Ala Ser Leu Thr Ala Ala Asp Thr Ala Thr Tyr Phe Cys Ala
                85                  90                  95

Arg Asp Asn Tyr Asp Asp His Gly Ala Trp Leu Tyr Phe Asn Leu Trp
            100                 105                 110

Gly Pro Gly Thr Leu Val Thr Val Ser Ser
        115                 120

<210> SEQ ID NO 36
<211> LENGTH: 123
<212> TYPE: PRT
<213> ORGANISM: Oryctolagus cuniculus

<400> SEQUENCE: 36

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Pro Glu Trp Ile
        35                  40                  45

Ala Cys Ile Tyr Gly Gly Ser Ile Gly Asp Pro Ser Tyr Ala Ser Trp
            50                  55                  60

Ala Lys Gly Arg Phe Thr Ile Ser Lys Ala Ser Ser Thr Thr Val Thr
 65                  70                  75                  80

Leu Gln Met Thr Ser Leu Thr Ala Ala Asp Thr Ala Thr Tyr Phe Cys
                85                  90                  95

Ala Arg Glu Glu Val Gly Val Ser Ala Pro Ser Arg Gly Trp Gly Leu
            100                 105                 110

Trp Gly Pro Gly Thr Leu Val Thr Val Ser Ser
            115                 120

<210> SEQ ID NO 37
<211> LENGTH: 121
<212> TYPE: PRT
<213> ORGANISM: Oryctolagus cuniculus

<400> SEQUENCE: 37

Gln Ser Leu Glu Glu Ser Gly Gly Asp Leu Val Lys Pro Gly Ala Ser
  1               5                  10                  15

Leu Thr Leu Thr Cys Thr Ala Ser Gly Phe Ser Phe Ser Ser Gly Tyr
                20                  25                  30

Tyr Met Cys Trp Val Arg Gln Ala Pro Gly Lys Gly Leu Glu Trp Ile
            35                  40                  45

Ala Cys Ile Gly Val Ser Thr Gln Gly Ala Tyr Tyr Ala Ser Trp Thr
 50                  55                  60

Glu Gly Arg Phe Thr Ile Ser Lys Thr Ser Ser Thr Thr Val Thr Leu
 65                  70                  75                  80

Gln Met Thr Ser Leu Thr Ala Ala Asp Thr Ala Thr Tyr Phe Cys Ala
                85                  90                  95

Arg Thr Ala Gly Ala Pro Ala Asp Ser Leu Tyr Phe Thr Leu Trp Gly
            100                 105                 110

Pro Gly Thr Leu Leu Thr Val Ser Ser
            115                 120

<210> SEQ ID NO 38
<211> LENGTH: 119
<212> TYPE: PRT
<213> ORGANISM: Oryctolagus cuniculus

<400> SEQUENCE: 38

Gln Ser Ser Glu Glu Ser Gly Gly Asp Leu Val Lys Pro Gly Ala Ser
  1               5                  10                  15

Leu Thr Leu Thr Cys Thr Ala Ser Gly Phe Ser Leu Ser Ser Gly Tyr
                20                  25                  30

Asp Met Cys Trp Val Arg Gln Ala Pro Gly Lys Gly Leu Glu Trp Ile
            35                  40                  45

Gly Cys Ile Lys Thr Gly Ala Thr Asn Glu Tyr Tyr Ala Ser Trp Ala
 50                  55                  60

Lys Gly Arg Phe Thr Ile Ser Arg Thr Ser Ser Thr Thr Val Thr Leu
 65                  70                  75                  80

Arg Met Thr Ser Leu Thr Ala Ala Asp Thr Ala Thr Tyr Phe Cys Ala
                85                  90                  95

Arg Glu Asp Thr Asn Asn Trp Gly Ser Leu Asn Leu Trp Gly Pro Gly
            100                 105                 110

Thr Leu Val Thr Val Ser Ser
            115

```
<210> SEQ ID NO 39
<211> LENGTH: 116
<212> TYPE: PRT
<213> ORGANISM: Oryctolagus cuniculus

<400> SEQUENCE: 39

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Gly Ser Phe Ala
                20                  25                  30

Val Gly Trp Val Arg Gln Pro Pro Gly Glu Gly Leu Glu Trp Ile Gly
            35                  40                  45

Leu Ile Asn Ala Asp Glu Ala Arg Tyr Tyr Ala Ser Trp Ala Lys Gly
        50                  55                  60

Arg Phe Thr Ile Ser Arg Thr Ser Thr Thr Val Asp Leu Arg Ile Thr
65                  70                  75                  80

Ser Pro Thr Ile Glu Asp Thr Ala Thr Tyr Phe Cys Ala Arg Ala Pro
                85                  90                  95

Asp Asn Phe Phe Tyr Tyr Phe Ser Met Trp Gly Pro Gly Thr Leu Val
                100                 105                 110

Thr Val Ser Ser
            115

<210> SEQ ID NO 40
<211> LENGTH: 116
<212> TYPE: PRT
<213> ORGANISM: Oryctolagus cuniculus

<400> SEQUENCE: 40

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Gly Ser Phe Ala
                20                  25                  30

Val Gly Trp Val Arg Gln Pro Pro Gly Glu Gly Leu Glu Trp Ile Gly
            35                  40                  45

Leu Ile Asn Ala Asp Glu Ala Arg Tyr Tyr Ala Ser Trp Ala Lys Gly
        50                  55                  60

Arg Phe Thr Ile Ser Arg Thr Ser Thr Thr Val Asp Leu Arg Ile Thr
65                  70                  75                  80

Ser Pro Thr Ile Glu Asp Thr Ala Thr Tyr Phe Cys Ala Arg Ala Pro
                85                  90                  95

Asp Asn Phe Phe Tyr Tyr Phe Ser Met Trp Gly Pro Gly Thr Leu Val
                100                 105                 110

Thr Val Ser Ser
            115

<210> SEQ ID NO 41
<211> LENGTH: 119
<212> TYPE: PRT
<213> ORGANISM: Oryctolagus cuniculus

<400> SEQUENCE: 41

Gln Ser Val Glu Glu Ser Gly Gly Arg Leu Val Thr Pro Gly Thr Pro
1               5                   10                  15

Leu Thr Leu Thr Cys Ser Val Ser Gly Phe Ser Leu Asn Thr Tyr Ala
                20                  25                  30

Val Ile Trp Val Arg Gln Ala Pro Gly Lys Gly Leu Glu Tyr Ile Gly
            35                  40                  45
```

Val Val Ala Gly Gly Tyr Ile Tyr Phe Thr Thr Trp Ala Lys Gly
        50                  55                  60

Arg Phe Thr Ile Ser Lys Thr Ser Thr Val Asp Leu Lys Met Thr
65                  70                  75                  80

Ser Pro Thr Thr Glu Asp Thr Ala Thr Tyr Phe Cys Ala Arg Gly Asp
                    85                  90                  95

Val Asp Asp Asn Ala Asp Tyr Ser Arg Leu Asp Ile Trp Gly Pro Gly
                100                 105                 110

Thr Leu Val Thr Val Ser Leu
        115

<210> SEQ ID NO 42
<211> LENGTH: 116
<212> TYPE: PRT
<213> ORGANISM: Oryctolagus cuniculus

<400> SEQUENCE: 42

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Gly Trp Phe Arg Gln Ala Pro Gly Lys Gly Leu Glu Trp Ile Gly
        35                  40                  45

Leu Ile Tyr Val Ser Gly Ile Thr Ser Tyr Ala Ser Trp Val Asn Gly
    50                  55                  60

Arg Phe Thr Ile Ser Lys Thr Ser Thr Val Asp Leu Lys Met Thr
65                  70                  75                  80

Ser Leu Thr Val Ser Asp Thr Ala Thr Tyr Phe Cys Ala Arg Asp Leu
                    85                  90                  95

Tyr Gly Asp His Tyr Tyr Ile Ile Trp Gly Pro Gly Thr Leu Val
                100                 105                 110

Thr Val Ser Ser
        115

<210> SEQ ID NO 43
<211> LENGTH: 116
<212> TYPE: PRT
<213> ORGANISM: Oryctolagus cuniculus

<400> SEQUENCE: 43

Gln Ser Met Glu Glu Ser Gly Gly Arg Leu Val Thr Pro Gly Thr Pro
1               5                   10                  15

Leu Thr Leu Thr Cys Thr Val Ser Gly Val Asp Leu Ser Ile Tyr Ala
            20                  25                  30

Met Ser Trp Val Arg Leu Ala Pro Gly Lys Gly Leu Glu Trp Ile Gly
        35                  40                  45

Val Ile Leu Ser Ser Gly Arg Ser Val Tyr Thr Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Ile Glu Asp Thr Ala Thr Tyr Phe Cys Ala Arg Gly Tyr
                    85                  90                  95

Asp Asp Tyr Val Ala Leu Phe Asn Met Trp Gly Pro Gly Thr Leu Val
                100                 105                 110

Thr Val Ser Ser
        115

```
<210> SEQ ID NO 44
<211> LENGTH: 116
<212> TYPE: PRT
<213> ORGANISM: Oryctolagus cuniculus

<400> SEQUENCE: 44

Gln Ser Met Glu Glu Ser Gly Gly Arg Leu Val Thr Pro Gly Thr Pro
1               5                   10                  15

Leu Thr Leu Thr Cys Thr Val Ser Gly Phe Asp Leu Ser Ile Tyr Ala
                20                  25                  30

Met Ser Trp Val Arg Gln Ala Pro Gly Lys Gly Leu Glu Trp Ile Gly
            35                  40                  45

Val Ile Leu Ser Ser Gly Arg Ser Val Tyr Ala Gly Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Ile Glu Asp Thr Ala Ala Tyr Phe Cys Ala Arg Gly Tyr
                85                  90                  95

Asp Asp Tyr Val Ala Leu Phe Asn Met Trp Gly Pro Gly Thr Leu Val
                100                 105                 110

Thr Val Ser Ser
            115

<210> SEQ ID NO 45
<211> LENGTH: 116
<212> TYPE: PRT
<213> ORGANISM: Oryctolagus cuniculus

<400> SEQUENCE: 45

Gln Ser Val Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
                20                  25                  30

Met Ser Trp Val Arg Gln Ala Pro Gly Lys Gly Leu Glu Trp Ile Gly
            35                  40                  45

Ile Ile Thr Ser Arg Ala Ile Thr Tyr Tyr Ala Thr Trp Ala Lys Gly
        50                  55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Gly Tyr
                85                  90                  95

Asp Asp Tyr Val Ala Leu Phe Asn Met Trp Gly Pro Gly Thr Leu Val
                100                 105                 110

Thr Val Ser Ser
            115

<210> SEQ ID NO 46
<211> LENGTH: 116
<212> TYPE: PRT
<213> ORGANISM: Oryctolagus cuniculus

<400> SEQUENCE: 46

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
                20                  25                  30

Met Ser Trp Val Arg Gln Ala Pro Gly Lys Gly Leu Glu Trp Ile Gly
            35                  40                  45
```

Ile Ile Ser Ser Thr Gly Asn Thr Cys Tyr Ala Asn Trp Ala Lys Gly
 50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                 85                  90                  95

Asp Asp Tyr Val Ala Leu Phe Asn Met Trp Gly Pro Gly Thr Leu Val
             100                 105                 110

Thr Val Ser Ser
        115

<210> SEQ ID NO 47
<211> LENGTH: 116
<212> TYPE: PRT
<213> ORGANISM: Oryctolagus cuniculus

<400> SEQUENCE: 47

Gln Ser Val Glu Glu Ser Gly Gly Arg Leu Val Thr Pro Gly Thr Pro
 1               5                  10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Ile Ile Phe Ser Ser Gly Asn Ile Val Tyr Ala Arg Arg Ala Lys Gly
 50                  55                  60

Arg Phe Thr Ile Ser Lys Thr Ser Thr Thr Val Asp Leu Gln Ile Thr
65                  70                  75                  80

Ser Pro Thr Ile Glu Asp Thr Ala Thr Tyr Phe Cys Ala Arg Gly Tyr
                 85                  90                  95

Asp Asp Tyr Val Ala Leu Phe Asn Met Trp Gly Pro Gly Thr Leu Val
             100                 105                 110

Thr Val Ser Ser
        115

<210> SEQ ID NO 48
<211> LENGTH: 110
<212> TYPE: PRT
<213> ORGANISM: Oryctolagus cuniculus

<400> SEQUENCE: 48

Asp Pro Val Leu Thr Gln Thr Pro Ala Ser Val Ser Glu Pro Val Gly
 1               5                  10                  15

Gly Thr Val Thr Ile Lys Cys Gln Ala Ser Glu Asp Leu Gly Ser Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Thr Ser Gly Val Pro Ser Arg Phe Lys Gly
 50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Asp Thr Tyr Tyr Gly Asn Thr
                 85                  90                  95

Tyr Leu Gly Ala Phe Gly Gly Gly Thr Glu Val Val Val Arg
             100                 105                 110

<210> SEQ ID NO 49
<211> LENGTH: 110

```
<212> TYPE: PRT
<213> ORGANISM: Oryctolagus cuniculus

<400> SEQUENCE: 49

Asp Leu Val Met Thr Gln Thr Pro Ser Pro Val Ser Ala Ala Val Gly
1               5                   10                  15

Gly Thr Val Thr Ile Asn Cys Gln Ala Ser Glu Glu Ile Gly Gly Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Thr Ser Gly Val Pro Ser Arg Phe Lys Gly
    50                  55                  60

Ser Gly Phe Gly Thr Glu Tyr Thr Leu Thr Ile Ser Asp Leu Glu Cys
65                  70                  75                  80

Asp Asp Ala Ala Thr Tyr Tyr Cys Gln Tyr Thr Tyr Tyr Gly Phe Thr
                85                  90                  95

Tyr Val Gly Pro Phe Gly Gly Gly Thr Glu Val Val Val Lys
            100                 105                 110

<210> SEQ ID NO 50
<211> LENGTH: 110
<212> TYPE: PRT
<213> ORGANISM: Oryctolagus cuniculus

<400> SEQUENCE: 50

Asp Leu Val Met Thr Gln Thr Pro Ser Pro Val Ser Ala Ala Val Gly
1               5                   10                  15

Gly Thr Val Thr Ile Asn Cys Gln Ala Ser Glu Glu Ile Gly Gly Asn
            20                  25                  30

Leu Ala Trp Tyr Gln Gln Lys Pro Gly Gln Pro Pro Gln Leu Leu Ile
        35                  40                  45

Tyr Ser Ala Ser Thr Leu Thr Ser Gly Val Pro Ser Arg Phe Lys Gly
    50                  55                  60

Ser Gly Phe Gly Thr Glu Tyr Thr Leu Thr Ile Ser Asp Leu Glu Cys
65                  70                  75                  80

Ala Asp Ala Ala Thr Tyr Tyr Cys Gln Tyr Thr Tyr Tyr Gly Phe Thr
                85                  90                  95

Tyr Val Gly Pro Phe Gly Gly Gly Thr Glu Val Val Val Lys
            100                 105                 110

<210> SEQ ID NO 51
<211> LENGTH: 110
<212> TYPE: PRT
<213> ORGANISM: Oryctolagus cuniculus

<400> SEQUENCE: 51

Asp Leu Val Met Thr Gln Thr Pro Ser Pro Val Ser Ala Ala Val Gly
1               5                   10                  15

Gly Thr Val Thr Ile Asn Cys Gln Ala Ser Glu Glu Ile Gly Gly Asn
            20                  25                  30

Leu Ala Trp Tyr Leu Gln Lys Pro Gly Gln Pro Pro Gln Leu Leu Ile
        35                  40                  45

Tyr Ser Ala Ser Thr Leu Thr Ser Gly Val Pro Ser Arg Phe Lys Gly
    50                  55                  60

Ser Gly Phe Gly Thr Glu Tyr Thr Leu Thr Ile Ser Asp Leu Glu Cys
65                  70                  75                  80

Ala Asp Ala Ala Thr Tyr Tyr Cys Gln Tyr Thr Tyr Tyr Gly Phe Ser
                85                  90                  95
```

```
Tyr Val Gly Pro Phe Gly Gly Gly Thr Glu Val Val Val Lys
            100                 105                 110

<210> SEQ ID NO 52
<211> LENGTH: 110
<212> TYPE: PRT
<213> ORGANISM: Oryctolagus cuniculus

<400> SEQUENCE: 52

Asp Leu Val Met Thr Gln Thr Pro Ser Pro Val Ser Ala Ala Val Gly
  1               5                  10                  15

Gly Thr Val Thr Ile Asn Cys Gln Ala Ser Glu Glu Ile Gly Gly Asn
             20                  25                  30

Leu Ala Trp Tyr Gln Gln Lys Pro Gly Gln Pro Pro Gln Leu Leu Ile
         35                  40                  45

Tyr Ser Ala Ser Thr Leu Ala Ser Gly Val Pro Ser Arg Phe Lys Gly
     50                  55                  60

Ser Gly Phe Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Phe Ser
                 85                  90                  95

Tyr Val Gly Pro Phe Gly Gly Gly Thr Glu Val Val Val Lys
            100                 105                 110

<210> SEQ ID NO 53
<211> LENGTH: 110
<212> TYPE: PRT
<213> ORGANISM: Oryctolagus cuniculus

<400> SEQUENCE: 53

Asp Leu Val Met Thr Gln Thr Pro Ser Pro Val Ser Ala Ala Val Gly
  1               5                  10                  15

Gly Thr Val Thr Ile Asn Cys Gln Ala Ser Glu Glu Ile Gly Gly Asn
             20                  25                  30

Leu Ala Trp Tyr Gln Gln Lys Pro Gly Gln Pro Pro Lys Leu Leu Ile
         35                  40                  45

Tyr Ser Ala Ser Thr Leu Thr Ser Gly Val Pro Ser Arg Phe Lys Gly
     50                  55                  60

Ser Gly Phe Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Phe Ser
                 85                  90                  95

Tyr Val Gly Pro Phe Gly Gly Gly Thr Glu Val Val Val Lys
            100                 105                 110

<210> SEQ ID NO 54
<211> LENGTH: 110
<212> TYPE: PRT
<213> ORGANISM: Oryctolagus cuniculus

<400> SEQUENCE: 54

Asp Leu Val Met Thr Gln Thr Pro Ser Pro Val Ser Ala Ala Val Gly
  1               5                  10                  15

Gly Thr Val Thr Ile Asn Cys Gln Ala Ser Glu Glu Ile Gly Gly Asn
             20                  25                  30

Leu Ala Trp Tyr Gln Gln Lys Pro Gly Gln Pro Pro Lys Leu Leu Ile
         35                  40                  45

Tyr Ser Ala Ser Thr Leu Thr Ser Gly Val Pro Ser Arg Phe Lys Gly
```

```
                50                  55                  60
Ser Gly Phe Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Phe Ser
                 85                  90                  95

Tyr Val Gly Pro Phe Gly Gly Gly Thr Glu Val Val Val Lys
                100                 105                 110

<210> SEQ ID NO 55
<211> LENGTH: 110
<212> TYPE: PRT
<213> ORGANISM: Oryctolagus cuniculus

<400> SEQUENCE: 55

Asp Leu Val Met Thr Gln Thr Pro Ser Pro Val Ser Ala Ala Val Gly
  1               5                  10                  15

Gly Thr Val Thr Ile Asn Cys Gln Ala Ser Glu Glu Ile Gly Asp Asn
                 20                  25                  30

Leu Ala Trp Tyr Gln Gln Lys Pro Gly Gln Pro Pro Lys Leu Leu Ile
                 35                  40                  45

Tyr Ser Ala Ser Thr Leu Thr Ser Gly Val Pro Ser Arg Phe Lys Gly
 50                  55                  60

Ser Gly Phe Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Phe Ser
                 85                  90                  95

Tyr Val Gly Pro Phe Gly Gly Gly Thr Glu Val Val Val Lys
                100                 105                 110

<210> SEQ ID NO 56
<211> LENGTH: 110
<212> TYPE: PRT
<213> ORGANISM: Oryctolagus cuniculus

<400> SEQUENCE: 56

Asp Leu Val Met Thr Gln Thr Pro Ser Pro Val Ser Ala Pro Val Gly
  1               5                  10                  15

Gly Thr Val Thr Ile Asn Cys Gln Ala Ser Glu Glu Ile Gly Gly Asn
                 20                  25                  30

Leu Ala Trp Tyr Gln Gln Lys Pro Gly Gln Pro Pro Lys Leu Leu Ile
                 35                  40                  45

Tyr Ser Ala Ser Thr Leu Thr Ser Gly Val Pro Ser Arg Phe Lys Gly
 50                  55                  60

Ser Gly Phe Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Phe Ser
                 85                  90                  95

Tyr Val Gly Pro Phe Gly Gly Gly Thr Glu Val Val Val Lys
                100                 105                 110

<210> SEQ ID NO 57
<211> LENGTH: 110
<212> TYPE: PRT
<213> ORGANISM: Oryctolagus cuniculus

<400> SEQUENCE: 57

Asp Leu Val Met Thr Gln Thr Pro Ser Pro Val Ser Ala Ala Val Gly
  1               5                  10                  15
```

Gly Thr Val Thr Ile Asn Cys Gln Ala Ser Glu Glu Ile Gly Gly Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Thr Ser Gly Val Pro Ser Arg Phe Lys Gly
50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Tyr Thr Tyr Tyr Gly Phe Ser
                85                  90                  95

Tyr Val Gly Pro Phe Gly Gly Gly Thr Glu Val Val Val Lys
            100                 105                 110

<210> SEQ ID NO 58
<211> LENGTH: 110
<212> TYPE: PRT
<213> ORGANISM: Oryctolagus cuniculus

<400> SEQUENCE: 58

Asp Leu Val Met Thr Gln Thr Pro Ser Pro Val Ser Ala Ala Val Gly
1               5                   10                  15

Gly Thr Val Thr Ile Asn Cys Gln Ala Ser Glu Glu Ile Gly Gly Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Thr Ser Gly Val Pro Ser Arg Phe Lys Gly
50                  55                  60

Ser Gly Ser Gly Thr Glu Tyr Thr Leu Thr Ile Asn Asp Leu Glu Cys
65                  70                  75                  80

Ala Asp Ala Ala Thr Tyr Tyr Cys Gln Tyr Pro Tyr Tyr Gly Phe Ser
                85                  90                  95

Tyr Val Gly Pro Phe Gly Gly Gly Thr Glu Val Val Val Lys
            100                 105                 110

<210> SEQ ID NO 59
<211> LENGTH: 110
<212> TYPE: PRT
<213> ORGANISM: Oryctolagus cuniculus

<400> SEQUENCE: 59

Asp Leu Val Met Thr Gln Thr Pro Ser Pro Val Ser Ala Ala Val Gly
1               5                   10                  15

Gly Thr Val Thr Ile Asn Cys Gln Ala Ser Glu Glu Ile Gly Gly Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Glu Tyr Ser Leu Ser Ile Ser Asp Leu Glu Cys
65                  70                  75                  80

Ala Asp Ala Ala Thr Tyr Tyr Cys Gln Tyr Thr Tyr Tyr Gly Phe Ser
                85                  90                  95

Tyr Val Gly Pro Phe Gly Gly Gly Thr Glu Val Val Val Lys
            100                 105                 110

<210> SEQ ID NO 60
<211> LENGTH: 110
<212> TYPE: PRT

-continued

<213> ORGANISM: Oryctolagus cuniculus

<400> SEQUENCE: 60

```
Asp Val Val Met Thr Gln Thr Pro Ala Ser Val Ser Glu Pro Val Gly
1               5                   10                  15
Gly Thr Val Thr Ile Asn Cys Gln Ala Ser Glu Glu Ile Gly Ser Asn
            20                  25                  30
Leu Ala Trp Tyr Gln Gln Lys Pro Gly Gln Pro Pro Lys Leu Leu Ile
        35                  40                  45
Tyr Ser Ala Ser Thr Leu Thr Ser Gly Val Pro Ser Arg Phe Lys Gly
50                  55                  60
Ser Gly Ser Gly Thr Glu Tyr Thr Leu Thr Ile Ser Asp Leu Glu Cys
65                  70                  75                  80
Ala Asp Ala Ala Thr Tyr Tyr Cys Gln Tyr Thr Tyr Tyr Gly Phe Asn
                85                  90                  95
Tyr Val Gly Pro Phe Gly Gly Gly Thr Glu Val Val Val Lys
            100                 105                 110
```

<210> SEQ ID NO 61
<211> LENGTH: 110
<212> TYPE: PRT
<213> ORGANISM: Oryctolagus cuniculus

<400> SEQUENCE: 61

```
Asp Val Val Met Thr Gln Thr Pro Ala Ser Val Ser Glu Pro Val Gly
1               5                   10                  15
Gly Thr Val Thr Ile Asn Cys Gln Ala Ser Glu Glu Ile Ala Ser Asn
            20                  25                  30
Leu Ala Trp Tyr Gln Gln Lys Pro Gly Gln Pro Pro Lys Leu Leu Ile
        35                  40                  45
Tyr Ser Ala Ser Thr Leu Thr Ser Gly Val Pro Ser Arg Phe Lys Gly
50                  55                  60
Ser Gly Ser Gly Thr Glu Tyr Thr Leu Thr Ile Ser Asp Leu Glu Cys
65                  70                  75                  80
Ala Asp Ala Ala Thr Tyr Tyr Cys Gln Tyr Thr Tyr Tyr Gly Phe Asn
                85                  90                  95
Tyr Val Gly Pro Phe Gly Gly Gly Thr Glu Val Val Val Lys
            100                 105                 110
```

<210> SEQ ID NO 62
<211> LENGTH: 110
<212> TYPE: PRT
<213> ORGANISM: Oryctolagus cuniculus

<400> SEQUENCE: 62

```
Asp Val Val Met Thr Gln Thr Pro Ala Ser Val Ser Glu Pro Val Gly
1               5                   10                  15
Gly Thr Val Thr Ile Asn Cys Gln Ala Ser Glu Glu Ile Gly Gly Asn
            20                  25                  30
Leu Ala Trp Tyr Gln Gln Lys Pro Gly Gln Pro Pro Lys Leu Leu Ile
        35                  40                  45
Tyr Ser Ala Ser Ser Leu Thr Ser Gly Val Pro Ser Arg Phe Lys Gly
50                  55                  60
Ser Glu Ser Gly Thr Glu Tyr Thr Leu Thr Ile Ser Asp Leu Glu Cys
65                  70                  75                  80
Ala Asp Ala Ala Thr Tyr Tyr Cys Gln Tyr Ser Tyr Tyr Gly Phe Asn
                85                  90                  95
```

Tyr Val Gly Pro Phe Gly Gly Thr Glu Val Val Val Lys
            100                 105                 110

<210> SEQ ID NO 63
<211> LENGTH: 110
<212> TYPE: PRT
<213> ORGANISM: Oryctolagus cuniculus

<400> SEQUENCE: 63

Gly Pro Val Met Thr Gln Thr Pro Ala Ser Val Ser Glu Pro Val Gly
1               5                   10                  15

Gly Thr Val Thr Ile Lys Cys Gln Ala Ser Glu Asp Ile Gly Ser Asn
            20                  25                  30

Leu Ala Trp Tyr Gln Gln Lys Pro Gly Gln Pro Pro Asn Leu Leu Val
        35                  40                  45

Tyr Ser Ala Ser Thr Leu Thr Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asp Thr Tyr Tyr Gly Asn Thr
                85                  90                  95

Tyr Leu Gly Ala Phe Gly Gly Gly Thr Glu Val Val Val Lys
            100                 105                 110

<210> SEQ ID NO 64
<211> LENGTH: 110
<212> TYPE: PRT
<213> ORGANISM: Oryctolagus cuniculus

<400> SEQUENCE: 64

Gly Pro Val Met Thr Gln Thr Pro Ala Ser Val Ser Glu Pro Val Gly
1               5                   10                  15

Gly Thr Val Thr Met Lys Cys Gln Ala Ser Glu Asp Ile Gly Ser Asn
            20                  25                  30

Leu Ala Trp Tyr Gln Gln Lys Pro Gly Gln Pro Pro Asn Leu Leu Val
        35                  40                  45

Phe Ser Ala Ser Thr Leu Ala Ser Gly Val Pro Ser Arg Phe Ala Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asp Ser Tyr Tyr Gly Asn Ser
                85                  90                  95

Tyr Leu Gly Ala Phe Gly Gly Gly Thr Glu Val Val Val Lys
            100                 105                 110

<210> SEQ ID NO 65
<211> LENGTH: 110
<212> TYPE: PRT
<213> ORGANISM: Oryctolagus cuniculus

<400> SEQUENCE: 65

Asp Pro Val Met Thr Gln Thr Pro Ala Ser Val Ser Glu Pro Val Gly
1               5                   10                  15

Gly Thr Val Thr Ile Asn Cys Gln Ala Ser Glu Glu Leu Gly Ser Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

```
Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Phe Gly Ser Ser
                 85                  90                  95

Tyr Leu Gly Ala Phe Gly Gly Gly Thr Glu Val Val Val Lys
            100                 105                 110

<210> SEQ ID NO 66
<211> LENGTH: 110
<212> TYPE: PRT
<213> ORGANISM: Oryctolagus cuniculus

<400> SEQUENCE: 66

Asp Pro Val Leu Thr Gln Thr Pro Ala Ser Val Ser Ala Val Val Gly
  1               5                  10                  15

Gly Thr Val Thr Ile Asn Cys Gln Thr Ser Glu Asp Ile Ala Ser Asn
                 20                  25                  30

Leu Ala Trp Tyr Gln Gln Lys Ser Gly Gln Arg Pro Lys Leu Leu Ile
             35                  40                  45

Tyr Glu Ala Ser Lys Leu Ala Ser Gly Val Pro Ser Arg Phe Lys Gly
         50                  55                  60

Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Tyr Thr Tyr Tyr Gly Ser Ser
                 85                  90                  95

Tyr Leu Gly Ala Phe Gly Gly Gly Thr Glu Val Val Val Lys
            100                 105                 110

<210> SEQ ID NO 67
<211> LENGTH: 111
<212> TYPE: PRT
<213> ORGANISM: Oryctolagus cuniculus

<400> SEQUENCE: 67

Ala Val Val Leu Thr Gln Thr Ala Ser Pro Val Ser Gly Ala Val Gly
  1               5                  10                  15

Gly Thr Val Thr Ile Lys Cys Gln Ala Ser Gln Asn Ile Tyr Asn Asn
                 20                  25                  30

Leu Ala Trp Tyr Arg Gln Lys Pro Gly Gln Pro Pro Lys Leu Leu Ile
             35                  40                  45

Tyr Ala Ala Ser Lys Leu Ala Ser Gly Val Pro Ser Arg Phe Ser Gly
         50                  55                  60

Ser Arg Ser Gly Thr Gln Phe Thr Leu Ser Ile Ser Asp Leu Glu Cys
 65                  70                  75                  80

Ala Asp Ala Ala Thr Tyr Tyr Cys Gln Ser Tyr Tyr Phe Asp Ser Ser
                 85                  90                  95

Ser Thr Asp Ala Ala Phe Gly Gly Gly Thr Glu Val Val Val Lys
            100                 105                 110

<210> SEQ ID NO 68
<211> LENGTH: 111
<212> TYPE: PRT
<213> ORGANISM: Oryctolagus cuniculus

<400> SEQUENCE: 68

Ala Val Val Leu Thr Gln Thr Ala Ser Pro Val Ser Gly Ala Val Gly
  1               5                  10                  15

Gly Thr Val Thr Ile Lys Cys Gln Ala Ser Gln Asn Ile Tyr Asn Asn
```

```
                    20                  25                  30
Leu Ala Trp Tyr Arg Gln Lys Pro Gly Gln Pro Pro Lys Leu Leu Ile
        35                  40                  45

Tyr Ala Ala Ser Lys Leu Ala Ser Gly Val Pro Ser Arg Phe Ser Gly
    50                  55                  60

Ser Arg Ser Gly Thr Gln Phe Thr Leu Ser Ile Ser Asp Leu Glu Cys
65                  70                  75                  80

Ala Asp Ala Ala Thr Tyr Tyr Cys Gln Ser Tyr Tyr Phe Asp Ser Ser
                85                  90                  95

Ser Thr Asp Ala Ala Phe Gly Gly Gly Thr Glu Val Val Val Lys
                100                 105                 110

<210> SEQ ID NO 69
<211> LENGTH: 111
<212> TYPE: PRT
<213> ORGANISM: Oryctolagus cuniculus

<400> SEQUENCE: 69

Ala Val Val Leu Thr Gln Thr Ala Ser Pro Val Ser Gly Ala Val Gly
1               5                   10                  15

Gly Thr Val Thr Ile Lys Cys Gln Ala Ser Gln Asn Ile Tyr Asn Asn
                20                  25                  30

Leu Ala Trp Tyr Arg Gln Lys Pro Gly Gln Pro Pro Lys Leu Leu Ile
        35                  40                  45

Tyr Ala Ala Ser Lys Leu Ala Ser Gly Val Pro Ser Arg Phe Ser Gly
    50                  55                  60

Ser Arg Ser Gly Thr Gln Phe Thr Leu Ser Ile Ser Asp Leu Glu Cys
65                  70                  75                  80

Ala Asp Ala Ala Thr Tyr Tyr Cys Gln Ser Tyr Tyr Phe Asp Ser Ser
                85                  90                  95

Ser Thr Asp Ala Ala Phe Gly Gly Gly Thr Glu Val Val Val Lys
                100                 105                 110

<210> SEQ ID NO 70
<211> LENGTH: 111
<212> TYPE: PRT
<213> ORGANISM: Oryctolagus cuniculus

<400> SEQUENCE: 70

Ala Val Val Leu Thr Gln Thr Ala Ser Pro Val Ser Gly Ala Val Gly
1               5                   10                  15

Gly Thr Val Thr Ile Lys Cys Gln Ala Ser Gln Asn Ile Tyr Asn Asn
                20                  25                  30

Leu Ala Trp Tyr Arg Gln Lys Pro Gly Gln Pro Pro Lys Leu Leu Ile
        35                  40                  45

Tyr Ala Ala Ser Lys Leu Ala Ser Gly Val Pro Ser Arg Phe Ser Gly
    50                  55                  60

Ser Arg Ser Gly Thr Gln Phe Thr Leu Ser Ile Ser Asp Leu Glu Cys
65                  70                  75                  80

Ala Asp Ala Ala Thr Tyr Tyr Cys Gln Ser Tyr Tyr Phe Asp Ser Ser
                85                  90                  95

Ser Thr Asp Ala Ala Phe Gly Gly Gly Thr Glu Val Val Val Lys
                100                 105                 110

<210> SEQ ID NO 71
<211> LENGTH: 111
<212> TYPE: PRT
<213> ORGANISM: Oryctolagus cuniculus
```

<400> SEQUENCE: 71

Ala Val Val Leu Thr Gln Thr Ala Ser Pro Val Ser Gly Ala Val Gly
1               5                   10                  15

Gly Thr Val Thr Ile Lys Cys Gln Ala Ser Gln Asn Ile Tyr Asn Asn
            20                  25                  30

Leu Ala Trp Tyr Arg Gln Lys Pro Gly Gln Pro Pro Lys Leu Leu Ile
        35                  40                  45

Tyr Ala Ala Ser Lys Leu Ala Ser Gly Val Pro Ser Arg Phe Ser Gly
50                  55                  60

Ser Arg Ser Gly Thr Gln Phe Thr Leu Ser Ile Ser Asp Leu Glu Cys
65                  70                  75                  80

Ala Asp Ala Ala Thr Tyr Tyr Cys Gln Ser Tyr Tyr Phe Asp Ser Ser
                85                  90                  95

Ser Thr Asp Ala Ala Phe Gly Gly Gly Thr Glu Val Val Val Lys
            100                 105                 110

<210> SEQ ID NO 72
<211> LENGTH: 111
<212> TYPE: PRT
<213> ORGANISM: Oryctolagus cuniculus

<400> SEQUENCE: 72

Ala Val Val Leu Thr Gln Thr Ala Ser Pro Val Ser Gly Ala Val Gly
1               5                   10                  15

Gly Thr Val Thr Ile Lys Cys Gln Ala Ser Gln His Ile Tyr Ser Asn
            20                  25                  30

Leu Ala Trp Tyr Gln Gln Lys Pro Gly Gln Arg Pro Lys Leu Leu Ile
        35                  40                  45

Tyr Ala Ala Ser Lys Leu Ala Ser Gly Val Pro Ser Arg Phe Ser Gly
50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Tyr Ser Ser Asp
                85                  90                  95

Ser Thr Asp Asn Thr Phe Gly Gly Gly Thr Glu Val Val Val Lys
            100                 105                 110

<210> SEQ ID NO 73
<211> LENGTH: 111
<212> TYPE: PRT
<213> ORGANISM: Oryctolagus cuniculus

<400> SEQUENCE: 73

Ala Val Val Leu Thr Gln Thr Pro Ser Ser Val Ser Ala Ala Val Gly
1               5                   10                  15

Gly Thr Val Thr Ile Asn Cys Gln Ala Ser Glu Asn Ile Tyr Ser Asn
            20                  25                  30

Leu Ala Trp Tyr Gln Gln Lys Pro Gly Gln Pro Pro Lys Leu Leu Ile
        35                  40                  45

Tyr Gly Ala Ser Ala Leu Pro Ser Gly Val Pro Ser Arg Phe Ser Gly
50                  55                  60

Ser Arg Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Phe Tyr Ser Ser Ser
                85                  90                  95

Asn Asp Asp Asn Pro Phe Gly Gly Gly Thr Glu Val Ala Val Lys

<210> SEQ ID NO 74
<211> LENGTH: 112
<212> TYPE: PRT
<213> ORGANISM: Oryctolagus cuniculus

<400> SEQUENCE: 74

Ala Val Val Leu Thr Gln Thr Thr Ser Val Ser Ala Asp Val Gly
1               5                   10                  15

Gly Thr Val Thr Ile Lys Cys Gln Ala Ser Glu Asn Ile Tyr Ser Leu
            20                  25                  30

Leu Ala Trp Tyr Gln Gln Lys Pro Gly Gln Pro Pro Lys Leu Leu Ile
        35                  40                  45

Tyr Ser Ala Ser Asp Leu Ala Ser Gly Val Pro Ser Arg Phe Ser Gly
    50                  55                  60

Ser Gly Phe Gly Thr Glu Phe Thr Leu Thr Ile Ser Asp Leu Glu Cys
65                  70                  75                  80

Ala Asp Ala Ala Thr Tyr His Cys Gln Ser Tyr Tyr Ser Gly Ser
                85                  90                  95

Ser Ala Asp Thr Gly Ala Phe Gly Gly Gly Thr Glu Val Val Val Lys
            100                 105                 110

<210> SEQ ID NO 75
<211> LENGTH: 111
<212> TYPE: PRT
<213> ORGANISM: Oryctolagus cuniculus

<400> SEQUENCE: 75

Ala Val Val Leu Thr Gln Thr Ala Ser Pro Val Ser Gly Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln His Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Glu Tyr Ile Leu Thr Ile Ser Asp Leu Glu Cys
65                  70                  75                  80

Ala Asp Ala Ala Thr Tyr Tyr Cys Gln Thr Asn Tyr Tyr Ser Ile Asn
                85                  90                  95

Gly Gly Glu Val Thr Phe Gly Gly Gly Thr Glu Val Val Val Lys
            100                 105                 110

<210> SEQ ID NO 76
<211> LENGTH: 110
<212> TYPE: PRT
<213> ORGANISM: Oryctolagus cuniculus

<400> SEQUENCE: 76

Asp Val Val Met Thr Gln Thr Pro Ala Ser Val Ser Glu Pro Val Gly
1               5                   10                  15

Gly Thr Val Thr Ile Asn Cys Gln Ala Ser Gln Ser Ile Arg Leu Ser
            20                  25                  30

Asp Leu Ala Trp Tyr Gln Gln Lys Pro Gly His Pro Pro Lys Leu Leu
        35                  40                  45

Ile Tyr Lys Ala Ser Lys Leu Ala Ser Gly Val Pro Ser Arg Phe Lys
    50                  55                  60

```
Gly Ser Gly Ser Gly Thr Glu Tyr Thr Leu Thr Ile Ser Gly Val Gln
 65                  70                  75                  80

Cys Asp Asp Ala Ala Thr Tyr Tyr Cys Gln Ser Ile Asp Tyr Asp Asn
                 85                  90                  95

Tyr Val Phe Phe Phe Gly Gly Gly Thr Glu Val Val Val Lys
                100                 105                 110

<210> SEQ ID NO 77
<211> LENGTH: 110
<212> TYPE: PRT
<213> ORGANISM: Oryctolagus cuniculus

<400> SEQUENCE: 77

Ala Leu Val Met Thr Gln Thr Pro Ala Ser Val Ser Ala Ala Val Gly
  1               5                  10                  15

Gly Thr Val Thr Ile Ser Cys Gln Ala Ser Gln Ser Ile His Ser Trp
                 20                  25                  30

Val Ser Trp Tyr Gln Gln Lys Pro Gly Gln Pro Pro Lys Leu Leu Ile
                 35                  40                  45

Tyr Tyr Ala Ala Thr Leu Ala Ser Gly Val Pro Ser Arg Phe Lys Gly
         50                  55                  60

Ser Gly Ser Gly Lys Gln Phe Thr Leu Thr Ile Ser Asp Leu Glu Cys
 65                  70                  75                  80

Asp Asp Ala Ala Thr Tyr Tyr Cys Gln Gln Asp Phe Gly Gly Ser Asp
                 85                  90                  95

Val Asp Asn Thr Phe Gly Gly Gly Thr Glu Val Val Val Ala
                100                 105                 110

<210> SEQ ID NO 78
<211> LENGTH: 112
<212> TYPE: PRT
<213> ORGANISM: Oryctolagus cuniculus

<400> SEQUENCE: 78

Gln Val Leu Thr Gln Ser Pro Ser Pro Val Ser Ala Ala Val Gly Gly
  1               5                  10                  15

Thr Val Thr Ile Asn Cys Gln Ala Ser Gln Ser Val Tyr Asn Gly Asp
                 20                  25                  30

Trp Leu Gly Trp Tyr Gln Gln Lys Pro Gly Gln Pro Pro Lys Leu Leu
                 35                  40                  45

Ile Tyr Asp Ala Ser Thr Leu Ala Ser Gly Val Ser Ser Leu Ile Asn
         50                  55                  60

Cys Asn Gly Ser Gly Thr Gln Trp Thr Leu Thr Ile Ser Gly Val Gln
 65                  70                  75                  80

Cys Asp Asp Ala Ala Thr Tyr Tyr Cys Gln Gly Glu Phe Ser Cys Ser
                 85                  90                  95

Ser Ala Asp Cys Val Ala Phe Gly Gly Gly Thr Glu Val Val Val Lys
                100                 105                 110

<210> SEQ ID NO 79
<211> LENGTH: 113
<212> TYPE: PRT
<213> ORGANISM: Oryctolagus cuniculus

<400> SEQUENCE: 79

Ala Asp Ile Val Leu Thr Gln Thr Pro Ala Ser Val Ser Ala Thr Val
  1               5                  10                  15

Gly Gly Thr Val Thr Ile Lys Cys Gln Ala Ser Gln Asn Ile Tyr Ser
                 20                  25                  30
```

Asn Leu Ala Trp Tyr Gln Gln Arg Pro Gly Gln Pro Pro Lys Leu Leu
              35                  40                  45

Ile Tyr Ala Ala Ser Asn Leu Ala Ser Gly Val Ser Ser Arg Phe Ser
 50                  55                  60

Gly Ser Arg Ser Gly Thr Glu Phe Thr Leu Thr Ile Ser Asp Leu Glu
 65                  70                  75                  80

Cys Ala Asp Ala Ala Thr Tyr Tyr Cys Gln Ser Tyr Tyr Tyr Ser Ser
                 85                  90                  95

Asp Asp Asn Tyr Leu Asn Thr Phe Gly Gly Gly Thr Glu Val Val Val
                100                 105                 110

Lys

<210> SEQ ID NO 80
<211> LENGTH: 113
<212> TYPE: PRT
<213> ORGANISM: Oryctolagus cuniculus

<400> SEQUENCE: 80

Ala Asp Ile Val Leu Thr Gln Thr Pro Ala Ser Val Ser Ala Thr Val
 1               5                   10                  15

Gly Gly Thr Val Thr Ile Lys Cys Gln Ala Ser Gln Asn Ile Tyr Ser
                20                  25                  30

Asn Leu Ala Trp Tyr Gln Gln Arg Pro Gly Gln Pro Pro Lys Leu Leu
              35                  40                  45

Ile Tyr Ala Ala Ser Asn Leu Ala Ser Gly Val Ser Ser Arg Phe Ser
 50                  55                  60

Gly Ser Arg Ser Gly Thr Glu Phe Thr Leu Thr Ile Ser Asp Leu Glu
 65                  70                  75                  80

Cys Ala Asp Ala Ala Thr Tyr Tyr Cys Gln Ser Tyr Tyr Tyr Ser Ser
                 85                  90                  95

Asp Asp Asn Tyr Leu Asn Thr Phe Gly Gly Gly Thr Glu Val Val Val
                100                 105                 110

Lys

<210> SEQ ID NO 81
<211> LENGTH: 107
<212> TYPE: PRT
<213> ORGANISM: Oryctolagus cuniculus

<400> SEQUENCE: 81

Gln Val Leu Thr Gln Thr Pro Ala Ser Val Ser Ala Thr Val Gly Gly
 1               5                   10                  15

Thr Val Thr Ile Lys Cys Gln Ala Ser Gln Asn Ile Tyr Ser Asn Leu
                20                  25                  30

Ala Trp Tyr Gln Gln Thr Pro Gly Gln Pro Pro Lys Leu Leu Ile Tyr
              35                  40                  45

Gly Ala Ser Asn Leu Ala Ser Gly Val Pro Ser Arg Phe Lys Gly Ser
 50                  55                  60

Gly Ser Gly Thr Gln Phe Thr Leu Thr Ile Ser Asp Leu Glu Cys Ala
 65                  70                  75                  80

Asp Ala Gly Thr Tyr Tyr Cys Gln Asp Tyr Tyr Gly Thr Ser Arg Tyr
                 85                  90                  95

Ile Phe Gly Gly Gly Thr Glu Val Val Val Gly
                100                 105

<210> SEQ ID NO 82

<211> LENGTH: 111
<212> TYPE: PRT
<213> ORGANISM: Oryctolagus cuniculus

<400> SEQUENCE: 82

```
Ala Asp Ile Val Met Thr Gln Thr Pro Ala Ser Val Ser Glu Pro Val
1               5                   10                  15
Gly Gly Thr Val Thr Ile Lys Cys Gln Ala Ser Gln Ser Ile Tyr Asn
            20                  25                  30
Tyr Leu Ser Trp Tyr Gln Gln Lys Pro Gly Gln Pro Pro Lys Leu Leu
        35                  40                  45
Ile Tyr Ala Ala Ser Asn Leu Ala Ser Gly Val Pro Ser Arg Phe Lys
    50                  55                  60
Gly Ser Gly Ser Gly Thr Gln Phe Thr Leu Thr Ile Ser Asp Leu Glu
65                  70                  75                  80
Cys Ala Asp Ala Ala Thr Tyr Tyr Cys Gln Ser Asn Tyr Gly Thr Ser
                85                  90                  95
Ser Ala Ser Tyr Ala Phe Gly Gly Gly Thr Glu Val Val Val Lys
            100                 105                 110
```

<210> SEQ ID NO 83
<211> LENGTH: 107
<212> TYPE: PRT
<213> ORGANISM: Oryctolagus cuniculus

<400> SEQUENCE: 83

```
Asp Val Val Met Thr Gln Thr Pro Phe Ser Val Ser Ala Ala Val Gly
1               5                   10                  15
Gly Thr Val Thr Ile Asn Cys Gln Ala Ser Glu Ser Ile Tyr Ile Asn
            20                  25                  30
Leu Ala Trp Tyr Gln Gln Lys Pro Gly Gln Pro Pro Lys Leu Leu Ile
        35                  40                  45
Tyr Asp Ala Ser Asn Leu Ala Ser Gly Val Pro Ser Arg Phe Lys Gly
    50                  55                  60
Ser Gly Ser Gly Thr Glu Tyr Thr Leu Thr Ile Ser Asp Leu Glu Cys
65                  70                  75                  80
Ala Asp Ala Thr Thr Tyr Tyr Cys Gln Asn Tyr Tyr Gly Ser Ser Tyr
                85                  90                  95
Asp Phe Gly Gly Gly Thr Glu Val Val Val Lys
            100                 105
```

<210> SEQ ID NO 84
<211> LENGTH: 111
<212> TYPE: PRT
<213> ORGANISM: Oryctolagus cuniculus

<400> SEQUENCE: 84

```
Asp Val Val Met Thr Gln Thr Pro Ala Ser Val Glu Ala Ala Val Gly
1               5                   10                  15
Gly Thr Val Thr Ile Asn Cys Gln Ala Ser Glu Asn Ile Tyr Ser Gly
            20                  25                  30
Leu Ala Trp Tyr Gln Gln Lys Pro Gly Gln Pro Pro Lys Leu Leu Ile
        35                  40                  45
Tyr Asp Ala Ser Asn Leu Glu Thr Gly Val Pro Ser Arg Phe Lys Gly
    50                  55                  60
Ser Gly Ser Gly Ala Gln Phe Thr Leu Thr Ile Ser Gly Val Gln Cys
65                  70                  75                  80
Asp Asp Ala Ala Thr Tyr Tyr Cys Gln Cys Ser Glu Tyr Asp Ser Ser
```

```
                 85                  90                  95
Tyr Val Pro Asn Val Phe Gly Gly Gly Thr Glu Val Val Val Lys
            100                 105                 110

<210> SEQ ID NO 85
<211> LENGTH: 107
<212> TYPE: PRT
<213> ORGANISM: Oryctolagus cuniculus

<400> SEQUENCE: 85

Gln Val Leu Thr Gln Thr Pro Ala Ser Val Ser Ala Ala Val Gly Gly
 1               5                  10                  15

Thr Val Thr Ile Lys Cys Gln Ala Ser Glu Ser Val Ser Ser Arg Leu
            20                  25                  30

Ala Trp Tyr Gln Gln Lys Ala Gly Gln Pro Pro Lys Leu Leu Ile Tyr
        35                  40                  45

Ser Ala Ser Thr Leu Ala Ser Gly Val Ser Ser Arg Phe Lys Gly Ser
    50                  55                  60

Gly Ser Gly Thr Glu Phe Ser Leu Thr Ile Ser Asp Leu Glu Cys Ala
65                  70                  75                  80

Asp Ala Ala Thr Tyr Tyr Cys Gln Ser Tyr Tyr Arg Ile Asp Arg Asn
                85                  90                  95

Leu Phe Gly Glu Gly Thr Glu Val Val Val Lys
            100                 105

<210> SEQ ID NO 86
<211> LENGTH: 110
<212> TYPE: PRT
<213> ORGANISM: Oryctolagus cuniculus

<400> SEQUENCE: 86

Ala Val Val Leu Thr Gln Thr Pro Ala Ser Val Ser Ala Ala Val Gly
 1               5                  10                  15

Gly Thr Val Thr Ile Asn Cys Gln Ala Ser Gln Ser Ile Asn Ser Gly
            20                  25                  30

Leu Ala Trp Tyr Gln Gln Lys Pro Gly Gln Pro Pro Lys Leu Leu Ile
        35                  40                  45

Tyr Gln Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Gln Thr Tyr Asp Thr Ser Asp
                85                  90                  95

Leu Asp Asn Ala Phe Gly Gly Gly Thr Glu Val Val Val Lys
            100                 105                 110

<210> SEQ ID NO 87
<211> LENGTH: 110
<212> TYPE: PRT
<213> ORGANISM: Oryctolagus cuniculus

<400> SEQUENCE: 87

Ala Tyr Asp Met Thr Gln Thr Pro Ala Ser Val Glu Val Ala Val Gly
 1               5                  10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Arg Pro Leu Leu Leu Ile
        35                  40                  45
```

```
Tyr Ala Ala Ser Thr Leu Ala Ser Gly Ala Ser Ser Arg Phe Lys Gly
        50                  55                  60

Ser Gly Ser Gly Thr Glu Phe Thr Leu Thr Ile Ser Gly Val Glu Cys
 65                  70                  75                  80

Ala Asp Ala Ala Thr Tyr Tyr Cys His Gln Ala Tyr Thr Thr Thr Gly
                85                  90                  95

Leu Asp Ala Gly Phe Gly Gly Gly Thr Glu Val Val Val Lys
                100                 105                 110
```

<210> SEQ ID NO 88
<211> LENGTH: 111
<212> TYPE: PRT
<213> ORGANISM: Oryctolagus cuniculus

<400> SEQUENCE: 88

```
Ile Val Met Thr Gln Thr Pro Ser Ser Lys Ser Val Pro Val Gly Asp
 1                   5                  10                  15

Thr Val Thr Ile Asn Cys Gln Ala Ser Glu Ser Val Tyr Asn Gly Asp
                20                  25                  30

Arg Leu Ala Trp Phe Gln Gln Lys Pro Gly Gln Pro Pro Lys Arg Leu
            35                  40                  45

Ile Tyr Leu Ala Ser Thr Leu Ala Ser Gly Val Pro Ser Arg Phe Lys
        50                  55                  60

Gly Ser Gly Ser Gly Thr Gln Phe Thr Leu Thr Ile Ser Asp Val Val
 65                  70                  75                  80

Cys Ala Asp Ala Ala Thr Tyr Tyr Cys Ala Gly Tyr Arg Ser Ala Ser
                85                  90                  95

Thr Asp Gly Asn Ala Phe Gly Gly Gly Thr Glu Val Val Val Lys
                100                 105                 110
```

<210> SEQ ID NO 89
<211> LENGTH: 110
<212> TYPE: PRT
<213> ORGANISM: Oryctolagus cuniculus

<400> SEQUENCE: 89

```
Ala Val Leu Thr Gln Thr Pro Ser Pro Val Ser Ala Ala Val Gly Gly
 1                   5                  10                  15

Thr Val Thr Ile Ser Cys Gln Ser Ser Lys Ser Val Tyr Ala Asp Asn
                20                  25                  30

Cys Leu Ala Trp Tyr Gln Gln Lys Pro Gly Gln Arg Pro Arg Leu Leu
            35                  40                  45

Ile Tyr Glu Ala Ser Lys Leu Pro Ser Gly Val Pro Ser Arg Phe Lys
        50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Ala Gly Asp Tyr Ser Pro Thr
                85                  90                  95

Ser Asp Asn Ser Phe Ser Gly Gly Thr Glu Val Val Val Lys
                100                 105                 110
```

<210> SEQ ID NO 90
<211> LENGTH: 110
<212> TYPE: PRT
<213> ORGANISM: Oryctolagus cuniculus

<400> SEQUENCE: 90

```
Ala Val Leu Thr Gln Thr Pro Ser Pro Val Ser Ala Ala Val Gly Gly
 1                   5                  10                  15
```

```
Thr Val Thr Ile Lys Cys Gln Ser Ser Gln Ser Val Tyr Asn His Asn
             20                  25                  30

Leu Leu Ser Trp Tyr Gln His Lys Pro Gly Gln Pro Pro Lys Leu Leu
         35                  40                  45

Ile Tyr Asp Ala Ser Thr Leu Ala Ser Gly Val Pro Ser Arg Phe Lys
 50                  55                  60

Gly Asn Gly Ser Gly Thr Gln Phe Thr Leu Thr Ile Ser Gly Val Gln
 65                  70                  75                  80

Cys Ala Asp Ala Ala Thr Tyr Tyr Cys Leu Gly Gly Tyr Asp Asp Asp
                 85                  90                  95

Ala Asp Thr Ala Phe Gly Gly Gly Thr Glu Val Val Val Arg
                100                 105                 110

<210> SEQ ID NO 91
<211> LENGTH: 110
<212> TYPE: PRT
<213> ORGANISM: Oryctolagus cuniculus

<400> SEQUENCE: 91

Ala Val Leu Thr Gln Thr Pro Ser Pro Val Ser Ala Ala Val Gly Gly
 1               5                  10                  15

Thr Val Thr Ile Lys Cys Gln Ser Ser Gln Ser Val Tyr Asn Asn Asn
             20                  25                  30

Leu Leu Ser Trp Tyr Gln His Lys Pro Gly Gln Pro Pro Lys Leu Leu
         35                  40                  45

Ile Tyr Asp Ala Ser Thr Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Ala Asp Ala Ala Thr Tyr Tyr Cys Leu Gly Gly Tyr Asp Asp Asp
                 85                  90                  95

Ala Asp Thr Ala Phe Gly Gly Gly Thr Glu Val Val Val Arg
                100                 105                 110

<210> SEQ ID NO 92
<211> LENGTH: 110
<212> TYPE: PRT
<213> ORGANISM: Oryctolagus cuniculus

<400> SEQUENCE: 92

Ala Val Leu Thr Gln Thr Pro Ser Pro Val Ser Ala Ala Val Gly Gly
 1               5                  10                  15

Thr Val Thr Ile Lys Cys Gln Ser Ser Gln Ser Val Tyr Asn Asn Ala
             20                  25                  30

Leu Leu Ser Trp Tyr Gln Gln Lys Ser Gly Gln Pro Pro Lys Leu Leu
         35                  40                  45

Ile Tyr Asp Ala Ser Lys Leu Ala Ser Gly Val Pro Asp Arg Phe Ser
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Gly Tyr Asp Asp Asp
                 85                  90                  95

Ala Asp Thr Thr Phe Gly Gly Gly Thr Glu Val Val Val Glu
                100                 105                 110

<210> SEQ ID NO 93
<211> LENGTH: 110
```

```
<212> TYPE: PRT
<213> ORGANISM: Oryctolagus cuniculus

<400> SEQUENCE: 93

Ala Val Leu Thr Gln Thr Pro Ser Pro Val Ser Ala Ala Val Gly Gly
 1               5                   10                  15

Thr Val Thr Ile Lys Cys Gln Ser Ser Gln Ser Val Tyr Asn Asn Asn
            20                  25                  30

Ala Leu Ser Trp Tyr Gln Gln Lys Pro Gly Gln Pro Lys Leu Leu
        35                  40                  45

Ile Tyr Asp Ala Ser Thr Leu Ala Ser Gly Val Pro Asp Arg Phe Ser
 50                      55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Gly Tyr Asp Asp Asp
                    85                  90                  95

Ala Asp Thr Ala Phe Gly Gly Gly Thr Glu Val Val Val Lys
                100                 105                 110

<210> SEQ ID NO 94
<211> LENGTH: 110
<212> TYPE: PRT
<213> ORGANISM: Oryctolagus cuniculus

<400> SEQUENCE: 94

Ala Val Val Thr Gln Thr Pro Ser Pro Val Ser Ala Thr Val Gly Gly
 1               5                   10                  15

Thr Val Thr Ile Ser Cys Gln Ser Ser Glu Ser Val Tyr Asn Asp Val
            20                  25                  30

Cys Leu Ser Trp Tyr Gln Gln Lys Pro Gly Gln Arg Pro Lys Leu Leu
        35                  40                  45

Ile Tyr Asp Ala Phe Thr Leu Ala Ser Gly Val Ser Ser Arg Phe Lys
 50                      55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Gly Tyr Asp Asp Asp
                    85                  90                  95

Ala Asp Thr Ala Phe Gly Gly Gly Thr Glu Val Val Val Lys
                100                 105                 110

<210> SEQ ID NO 95
<211> LENGTH: 17
<212> TYPE: PRT
<213> ORGANISM: Artificial Sequence
<220> FEATURE:
<223> OTHER INFORMATION: VH3 region

<400> SEQUENCE: 95

Cys Ala Arg Asp Ile Asn Ser Tyr Gly Tyr Ala Tyr Ala Thr Asp Ile
 1               5                   10                  15

Trp

<210> SEQ ID NO 96
<211> LENGTH: 15
<212> TYPE: PRT
<213> ORGANISM: Artificial Sequence
<220> FEATURE:
<223> OTHER INFORMATION: VH3 region

<400> SEQUENCE: 96
```

```
Cys Ala Arg Ser Gly Tyr Ala Gly Ser Ser Tyr Tyr Asn Leu Trp
1               5                   10                  15
```

<210> SEQ ID NO 97
<211> LENGTH: 15
<212> TYPE: PRT
<213> ORGANISM: Artificial Sequence
<220> FEATURE:
<223> OTHER INFORMATION: VH3 region

<400> SEQUENCE: 97

```
Cys Ala Arg Ser Asp Tyr Ser Tyr Gly Gly Ala Tyr Asp Ile Trp
1               5                   10                  15
```

<210> SEQ ID NO 98
<211> LENGTH: 13
<212> TYPE: PRT
<213> ORGANISM: Artificial Sequence
<220> FEATURE:
<223> OTHER INFORMATION: VH3 region

<400> SEQUENCE: 98

```
Cys Ala Arg Arg Val Asp Ser Thr Gly Thr Asp Ile Trp
1               5                   10
```

<210> SEQ ID NO 99
<211> LENGTH: 10
<212> TYPE: PRT
<213> ORGANISM: Artificial Sequence
<220> FEATURE:
<223> OTHER INFORMATION: VH3 region

<400> SEQUENCE: 99

```
Cys Gly Ser Gly Tyr Tyr Ile Asn Ile Trp
1               5                   10
```

<210> SEQ ID NO 100
<211> LENGTH: 17
<212> TYPE: PRT
<213> ORGANISM: Artificial Sequence
<220> FEATURE:
<223> OTHER INFORMATION: VH3 region

<400> SEQUENCE: 100

```
Cys Ala Arg Gly Gly Ala Gly Ile Ser Gly Tyr Thr Tyr Phe Asn Ile
1               5                   10                  15

Trp
```

<210> SEQ ID NO 101
<211> LENGTH: 14
<212> TYPE: PRT
<213> ORGANISM: Artificial Sequence
<220> FEATURE:
<223> OTHER INFORMATION: VH3 region

<400> SEQUENCE: 101

```
Cys Ala Arg Gly Cys Pro Gly Tyr Gly Asp Asn Asp Ile Trp
1               5                   10
```

<210> SEQ ID NO 102
<211> LENGTH: 11
<212> TYPE: PRT
<213> ORGANISM: Artificial Sequence
<220> FEATURE:
<223> OTHER INFORMATION: VH3 region

<400> SEQUENCE: 102

```
Cys Ala Arg Gly Tyr Trp Ser Leu Asp Ile Trp
1               5                   10
```

<210> SEQ ID NO 103
<211> LENGTH: 15
<212> TYPE: PRT
<213> ORGANISM: Artificial Sequence
<220> FEATURE:
<223> OTHER INFORMATION: VH3 region

<400> SEQUENCE: 103

```
Cys Val Arg Asp Ser Thr Gly Ile Ser Ala Leu Phe Asn Val Trp
1               5                   10                  15
```

<210> SEQ ID NO 104
<211> LENGTH: 16
<212> TYPE: PRT
<213> ORGANISM: Artificial Sequence
<220> FEATURE:
<223> OTHER INFORMATION: VH3 region

<400> SEQUENCE: 104

```
Cys Ala Arg Arg Gly Ala Thr Ala Ser His Arg Trp Phe Thr Ile Trp
1               5                   10                  15
```

<210> SEQ ID NO 105
<211> LENGTH: 16
<212> TYPE: PRT
<213> ORGANISM: Artificial Sequence
<220> FEATURE:
<223> OTHER INFORMATION: VH3 region

<400> SEQUENCE: 105

```
Cys Gly Ser Gly Ala Asn Ile Glu Asn Glu Phe Phe Asn Ala Ile Trp
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: VH3 region

<400> SEQUENCE: 106

```
Cys Ala Arg Gly Asp Arg Ser His Asp Tyr Asp Tyr Phe Lys Ile Trp
1               5                   10                  15
```

<210> SEQ ID NO 107
<211> LENGTH: 18
<212> TYPE: PRT
<213> ORGANISM: Artificial Sequence
<220> FEATURE:
<223> OTHER INFORMATION: VH3 region

<400> SEQUENCE: 107

```
Cys Ala Arg Ser Gln Asp Ser Gly Ser His Asp Asp Phe Pro Phe Asn
1               5                   10                  15

Ile Trp
```

<210> SEQ ID NO 108
<211> LENGTH: 15
<212> TYPE: PRT
<213> ORGANISM: Artificial Sequence
<220> FEATURE:
<223> OTHER INFORMATION: VH3 region

<400> SEQUENCE: 108

Cys Ala Arg Ser Pro Gly Gly Ile Gly Asp Ala Phe Asp Pro Trp
1               5                   10                  15

<210> SEQ ID NO 109
<211> LENGTH: 11
<212> TYPE: PRT
<213> ORGANISM: Artificial Sequence
<220> FEATURE:
<223> OTHER INFORMATION: VH3 region

<400> SEQUENCE: 109

Cys Ala Arg Gly Trp Val Gly Leu Asn Ile Trp
1               5                   10

<210> SEQ ID NO 110
<211> LENGTH: 15
<212> TYPE: PRT
<213> ORGANISM: Artificial Sequence
<220> FEATURE:
<223> OTHER INFORMATION: VH3 region

<400> SEQUENCE: 110

Cys Ala Arg Arg Ala Asp Ser Tyr Gly Tyr Ala Tyr Asp Ile Trp
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: VH3 region

<400> SEQUENCE: 111

Cys Ala Arg Tyr Gly Ala Ser Val Thr Tyr Phe Asn Ile Trp
1               5                   10

<210> SEQ ID NO 112
<211> LENGTH: 17
<212> TYPE: PRT
<213> ORGANISM: Artificial Sequence
<220> FEATURE:
<223> OTHER INFORMATION: VH3 region

<400> SEQUENCE: 112

Cys Ala Arg Phe Arg Ile Leu Val Ile Val Leu Val Pro Leu Asp Leu
1               5                   10                  15

Trp

<210> SEQ ID NO 113
<211> LENGTH: 17
<212> TYPE: PRT
<213> ORGANISM: Artificial Sequence
<220> FEATURE:
<223> OTHER INFORMATION: VH3 region

<400> SEQUENCE: 113

Cys Ala Arg Gly Ala Thr Met Thr Met Val Arg Gly Trp Leu Asp Leu
1               5                   10                  15

Trp

<210> SEQ ID NO 114
<211> LENGTH: 13
<212> TYPE: PRT
<213> ORGANISM: Artificial Sequence
<220> FEATURE:
<223> OTHER INFORMATION: VH3 region -continued

<400> SEQUENCE: 114

Cys Ala Arg Leu Gly Leu Val Val Ile Asn Ile Trp
1               5                   10

<210> SEQ ID NO 115
<211> LENGTH: 405
<212> TYPE: DNA
<213> ORGANISM: Oryctolagus cuniculus

<400> SEQUENCE: 115
atggacacga gggcccccac tcagctgctg gggctcctgc tgctctggct cccaggtgcc      60
acatttgctc aactgctgac ccagactgca tcgcccgtgt ctacagctgt gggaggcaca     120
gtcaccatca gtgccagtc cagtcagagt gttttaaga ggaagtcctt atcctggtat       180
cagcagaaac cagggcaggc tcccaaactc ctgatctacg atgcatccac tctggcatct    240
ggggtcccat cacggttcag tggcagtgga tctgggacac agttcactct caccatcagc    300
ggcgtgcagt gtgacgatgc tgccacttac tactgtctag cagttttga ttgtactagt     360
gctgattgtc atgttttcgg cggagggacc gaggtggtgg tcaaa                    405

<210> SEQ ID NO 116
<211> LENGTH: 135
<212> TYPE: PRT
<213> ORGANISM: Oryctolagus cuniculus

<400> SEQUENCE: 116

Met Asp Thr Arg Ala Pro Thr Gln Leu Leu Gly Leu Leu Leu Trp
1               5                   10                  15

Leu Pro Gly Ala Thr Phe Ala Gln Leu Leu Thr Gln Thr Ala Ser Pro
                20                  25                  30

Val Ser Thr Ala Val Gly Gly Thr Val Thr Ile Lys Cys Gln Ser Ser
        35                  40                  45

Gln Ser Val Phe Lys Arg Lys Ser Leu Ser Trp Tyr Gln Gln Lys Pro
    50                  55                  60

Gly Gln Ala Pro Lys Leu Leu Ile Tyr Asp Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Ser Phe Asp Cys Thr Ser Ala Asp Cys His Val Phe Gly Gly
        115                 120                 125

Gly Thr Glu Val Val Val Lys
    130                 135

<210> SEQ ID NO 117
<211> LENGTH: 39
<212> TYPE: DNA
<213> ORGANISM: Artificial Sequence
<220> FEATURE:
<223> OTHER INFORMATION: Synthetic Primer

<400> SEQUENCE: 117
aacatgacaa tcagcactag tacaatcaaa actgcctag                            39

<210> SEQ ID NO 118
<211> LENGTH: 20
<212> TYPE: DNA
<213> ORGANISM: Artificial Sequence
<220> FEATURE:

-continued

<223> OTHER INFORMATION: Synthetic Primer

<400> SEQUENCE: 118
gctgctctgg ctcccaggtg                                        20

<210> SEQ ID NO 119
<211> LENGTH: 112
<212> TYPE: PRT
<213> ORGANISM: Oryctolagus cuniculus

<400> SEQUENCE: 119

Gln Leu Leu Thr Gln Thr Ala Ser Pro Val Ser Thr Ala Val Gly Gly
1               5                   10                  15

Thr Val Thr Ile Lys Cys Gln Ser Ser Gln Ser Val Phe Lys Arg Lys
            20                  25                  30

Ser Leu Ser Trp Tyr Gln Gln Lys Pro Gly Gln Ala Pro Lys Leu Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Ser Phe Asp Cys Thr
                85                  90                  95

Ser Ala Asp Cys His Val Phe Gly Gly Gly Thr Glu Val Val Val Lys
            100                 105                 110

<210> SEQ ID NO 120
<211> LENGTH: 112
<212> TYPE: PRT
<213> ORGANISM: Oryctolagus cuniculus

<400> SEQUENCE: 120

Gln Val Leu Thr Gln Thr Ala Ser Pro Val Ser Ala Ala Val Gly Gly
1               5                   10                  15

Thr Val Thr Ile Lys Cys Gln Ser Ser Gln Ser Val Tyr Lys Arg Lys
            20                  25                  30

Ser Leu Ser Trp Tyr Gln Gln Lys Pro Gly Gln Ala Pro Lys Leu Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Ser Phe Asp Cys Thr
                85                  90                  95

Ser Ala Asp Cys His Val Phe Gly Gly Gly Thr Glu Val Val Val Lys
            100                 105                 110

<210> SEQ ID NO 121
<211> LENGTH: 112
<212> TYPE: PRT
<213> ORGANISM: Oryctolagus cuniculus

<400> SEQUENCE: 121

Gln Val Leu Thr Gln Thr Ala Ser Pro Val Ser Ala Ala Val Gly Gly
1               5                   10                  15

Thr Val Thr Ile Asn Cys Gln Ser Ser Gln Ser Val Tyr Lys Arg Lys
            20                  25                  30

Ser Leu Ser Trp Tyr Gln Gln Lys Pro Gly Gln Ala Pro Lys Leu Leu
        35                  40                  45

Ile Tyr Asp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Ser Phe Asp Cys Thr
                 85                  90                  95

Arg Ala Asp Cys His Val Phe Gly Gly Gly Thr Glu Val Val Val Lys
            100                 105                 110

<210> SEQ ID NO 122
<211> LENGTH: 112
<212> TYPE: PRT
<213> ORGANISM: Oryctolagus cuniculus

<400> SEQUENCE: 122

Gln Val Leu Thr Gln Thr Ala Ser Pro Val Ser Ala Ala Val Gly Gly
 1               5                  10                  15

Thr Val Thr Ile Lys Cys Gln Ser Ser Gln Ser Val Tyr Lys Arg Lys
                20                  25                  30

Ser Leu Ser Trp Tyr Gln Gln Lys Pro Gly Gln Ala Pro Lys Leu Leu
            35                  40                  45

Ile Tyr Asp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Ser Phe Asp Cys Thr
                 85                  90                  95

Arg Ala Asp Cys His Val Phe Gly Gly Gly Thr Glu Val Val Val Lys
            100                 105                 110

<210> SEQ ID NO 123
<211> LENGTH: 112
<212> TYPE: PRT
<213> ORGANISM: Oryctolagus cuniculus

<400> SEQUENCE: 123

Gln Val Leu Thr Gln Thr Ala Ser Pro Val Ser Ala Ala Val Gly Gly
 1               5                  10                  15

Thr Val Thr Ile Lys Cys Gln Ser Ser Gln Ser Val Tyr Lys Arg Lys
                20                  25                  30

Ser Leu Ser Trp Tyr Gln Gln Lys Pro Gly Gln Pro Pro Lys Leu Leu
            35                  40                  45

Ile Tyr Asp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Ser Phe Asp Cys Thr
                 85                  90                  95

Ser Ala Asp Cys His Val Phe Gly Gly Gly Thr Glu Val Val Val Lys
            100                 105                 110

<210> SEQ ID NO 124
<211> LENGTH: 112
<212> TYPE: PRT
<213> ORGANISM: Oryctolagus cuniculus

<400> SEQUENCE: 124

Gln Val Leu Thr Gln Thr Ala Ser Pro Val Ser Ala Ala Val Gly Gly
 1               5                  10                  15

-continued

```
                1               5                  10                 15
Thr Val Thr Ile Lys Cys Gln Ser Ser Gln Ser Val Tyr Lys Ser Lys
                    20                  25                 30

His Cys Ser Trp Tyr Gln Gln Lys Pro Gly Gln Pro Pro Lys Leu Leu
                    35                  40                 45

Ile Tyr Asp Ala Ser Thr Leu Ala Ser Gly Val Pro Ser Arg Phe Lys
                    50                  55                 60

Gly Ser Gly Ser Gly Thr Glu Phe Thr Leu Thr Ile Ser Gly Val Gln
65                      70                  75                 80

Cys Asp Asp Ala Ala Thr Tyr Tyr Cys Leu Gly Ser Tyr Asp Cys Ser
                    85                  90                 95

Thr Ala Asp Cys His Val Phe Gly Gly Gly Thr Gly Val Val Val Lys
                    100                 105                110
```

<210> SEQ ID NO 125
<211> LENGTH: 112
<212> TYPE: PRT
<213> ORGANISM: Oryctolagus cuniculus

<400> SEQUENCE: 125

```
Gln Val Leu Thr Gln Thr Pro Ser Ser Val Ser Ala Ala Val Gly Gly
1               5                  10                 15

Thr Val Thr Ile Lys Cys Gln Ser Ser Gln Ser Val Tyr Lys Ser Lys
                    20                  25                 30

His Leu Ser Trp Phe Gln Gln Lys Pro Gly Gln Ala Pro Lys Leu Leu
                    35                  40                 45

Ile Tyr Asp Thr Ser Thr Leu Ala Ser Gly Val Pro Ser Arg Phe Ser
                    50                  55                 60

Gly Ser Gly Ser Gly Thr Gln Phe Thr Leu Thr Ile Ser Gly Val Gln
65                      70                  75                 80

Cys Asp Asp Ala Ala Ala Tyr Tyr Cys Leu Gly Ser Tyr Asp Cys Leu
                    85                  90                 95

Ser Ala Asp Cys His Val Phe Gly Gly Gly Thr Glu Val Val Val Lys
                    100                 105                110
```

<210> SEQ ID NO 126
<211> LENGTH: 112
<212> TYPE: PRT
<213> ORGANISM: Oryctolagus cuniculus

<400> SEQUENCE: 126

```
Gln Val Leu Thr Gln Thr Pro Ser Ser Val Ser Ala Ala Val Gly Gly
1               5                  10                 15

Thr Val Thr Ile Lys Cys Gln Ser Ser Gln Ser Val Tyr Lys Ser Lys
                    20                  25                 30

His Leu Ser Trp Phe Gln Gln Lys Pro Gly Gln Ala Pro Lys Leu Leu
                    35                  40                 45

Ile Tyr Asp Thr Ser Thr Leu Ala Ser Gly Val Pro Ser Arg Phe Lys
                    50                  55                 60

Gly Ser Gly Ser Gly Thr Gln Phe Thr Leu Thr Ile Ser Gly Val Gln
65                      70                  75                 80

Cys Asp Asp Ala Ala Ala Tyr Tyr Cys Leu Gly Ser Tyr Asp Cys Leu
                    85                  90                 95

Ser Ala Asp Cys His Val Phe Gly Gly Gly Thr Glu Val Val Val Lys
                    100                 105                110
```

<210> SEQ ID NO 127

```
<211> LENGTH: 112
<212> TYPE: PRT
<213> ORGANISM: Oryctolagus cuniculus

<400> SEQUENCE: 127

Gln Val Leu Thr Gln Thr Pro Ser Pro Val Ser Ala Ala Val Gly Gly
 1               5                  10                  15

Thr Val Thr Ile Asn Cys Gln Ala Ser Gln Ser Val Tyr Lys Ser Lys
             20                  25                  30

His Leu Ser Trp Tyr Gln Gln Lys Pro Gly Gln Pro Pro Lys Leu Leu
         35                  40                  45

Ile Tyr Asp Ala Ser Lys Leu Ala Ser Gly Val Pro Ser Arg Phe Lys
     50                  55                  60

Gly Ser Gly Ser Gly Thr His Phe Thr Leu Thr Ile Ser Gly Val Gln
 65                  70                  75                  80

Cys Asp Asp Ala Ala Thr Tyr Tyr Cys Leu Gly Ser Tyr Asp Cys Ser
                 85                  90                  95

Arg Ala Asp Cys His Val Phe Gly Gly Gly Thr Glu Val Val Val Lys
            100                 105                 110

<210> SEQ ID NO 128
<211> LENGTH: 112
<212> TYPE: PRT
<213> ORGANISM: Oryctolagus cuniculus

<400> SEQUENCE: 128

Gln Val Leu Thr Gln Thr Pro Ser Pro Val Ser Ala Ala Val Gly Gly
 1               5                  10                  15

Thr Val Thr Ile Asn Cys Arg Ala Ser Gln Thr Val Tyr Lys Ser Lys
             20                  25                  30

His Leu Ser Trp Tyr Gln Gln Lys Pro Gly Gln Pro Pro Lys Leu Leu
         35                  40                  45

Ile Tyr Asp Ala Ser Lys Leu Ala Ser Gly Val Pro Ser Arg Phe Lys
     50                  55                  60

Gly Ser Gly Ser Gly Thr Gln Phe Thr Leu Thr Ile Ser Gly Val Glu
 65                  70                  75                  80

Cys Asp Asp Ala Ala Thr Tyr Tyr Cys Leu Gly Ser Tyr Asp Cys Ser
                 85                  90                  95

Ser Thr Asp Cys His Val Phe Gly Gly Gly Thr Glu Val Val Val Lys
            100                 105                 110

<210> SEQ ID NO 129
<211> LENGTH: 112
<212> TYPE: PRT
<213> ORGANISM: Oryctolagus cuniculus

<400> SEQUENCE: 129

Gln Val Leu Thr Gln Thr Pro Ser Pro Val Ser Ala Ala Val Gly Gly
 1               5                  10                  15

Thr Val Thr Ile Asn Cys Gln Ala Ser Gln Arg Val Tyr Lys Asn Lys
             20                  25                  30

His Leu Ser Trp Tyr Gln Gln Lys Pro Gly Gln Arg Pro Lys Leu Leu
         35                  40                  45

Ile Tyr Asp Ala Ser Thr Leu Ala Ser Gly Val Pro Ser Arg Phe Lys
     50                  55                  60

Gly Ser Gly Ser Gly Thr Gln Phe Thr Leu Thr Leu Ser Gly Val Gln
 65                  70                  75                  80

Cys Asp Asp Ala Ala Thr Tyr Tyr Cys Leu Gly Ser Tyr Asp Cys Thr
```

```
                    85                  90                  95

Ile Thr Asp Cys His Val Phe Gly Gly Gly Thr Glu Val Val Lys
                   100                 105                 110

<210> SEQ ID NO 130
<211> LENGTH: 112
<212> TYPE: PRT
<213> ORGANISM: Oryctolagus cuniculus

<400> SEQUENCE: 130

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Lys Arg Lys
                20                  25                  30

Tyr Leu Ser Trp Tyr Gln Lys Lys Pro Gly Gln Ala Pro Lys Leu Leu
            35                  40                  45

Ile Tyr Asp Ala Ser Thr Leu Ala Ser Gly Val Pro Ser Arg Phe Ser
        50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Ser Tyr Asp Cys Ser
                85                  90                  95

Arg Thr Asp Cys His Val Phe Ala Gly Gly Thr Glu Leu Val Val Lys
                100                 105                 110

<210> SEQ ID NO 131
<211> LENGTH: 396
<212> TYPE: DNA
<213> ORGANISM: Oryctolagus cuniculus

<400> SEQUENCE: 131
atggacacga gggcccccac tcagctgctg gggctcctgc tgctctggct cccaggtgcc      60
atatgtgacc ctgtgctgac ccagactcca tcctccgtgt ctgcagctgt gggaggcaca     120
gtcaccatca attgccagtc cagtcagagg gtttggaaga acagctactt atcctggttt     180
cagcagaaac cagggcagcc tcccaagcgc ctgatctatt atacatccac tctgccatct     240
ggggtcccat cgcggttcaa aggcagtgga tctgggacac agttcactct caccatcagc     300
gacctggagt gtgacgatgc tgccacttac tactgtctag ggagttatag tgatgatata     360
tattctttcg gcggagggac cgaggtggtg gtcaaa                               396

<210> SEQ ID NO 132
<211> LENGTH: 132
<212> TYPE: PRT
<213> ORGANISM: Oryctolagus cuniculus

<400> SEQUENCE: 132

Met Asp Thr Arg Ala Pro Thr Gln Leu Leu Gly Leu Leu Leu Leu Trp
1               5                   10                  15

Leu Pro Gly Ala Ile Cys Asp Pro Val Leu Thr Gln Thr Pro Ser Ser
                20                  25                  30

Val Ser Ala Ala Val Gly Gly Thr Val Thr Ile Asn Cys Gln Ser Ser
            35                  40                  45

Gln Arg Val Trp Lys Asn Ser Tyr Leu Ser Trp Phe Gln Gln Lys Pro
        50                  55                  60

Gly Gln Pro Pro Lys Arg Leu Ile Tyr Tyr Thr Ser Thr Leu Pro Ser
65                  70                  75                  80

Gly Val Pro Ser Arg Phe Lys Gly Ser Gly Ser Gly Thr Gln Phe Thr
```

-continued

```
                    85                  90                  95
Leu Thr Ile Ser Asp Leu Glu Cys Asp Asp Ala Ala Thr Tyr Tyr Cys
            100                 105                 110

Leu Gly Ser Tyr Ser Asp Asp Ile Tyr Ser Phe Gly Gly Gly Thr Glu
        115                 120                 125

Val Val Val Lys
    130

<210> SEQ ID NO 133
<211> LENGTH: 30
<212> TYPE: DNA
<213> ORGANISM: Artificial Sequence
<220> FEATURE:
<223> OTHER INFORMATION: Synthetic Primer

<400> SEQUENCE: 133
agaatatata tcatcactat aactccctag                                      30

<210> SEQ ID NO 134
<211> LENGTH: 20
<212> TYPE: DNA
<213> ORGANISM: Artificial Sequence
<220> FEATURE:
<223> OTHER INFORMATION: Synthetic Primer

<400> SEQUENCE: 134
gctgctctgg ctcccaggtg                                                 20

<210> SEQ ID NO 135
<211> LENGTH: 110
<212> TYPE: PRT
<213> ORGANISM: Oryctolagus cuniculus

<400> SEQUENCE: 135

Asp Pro Val Leu Thr Gln Thr Pro Ser Ser Val Ser Ala Ala Val Gly
1               5                   10                  15

Gly Thr Val Thr Ile Asn Cys Gln Ser Ser Gln Arg Val Trp Lys Asn
            20                  25                  30

Ser Tyr Leu Ser Trp Phe Gln Gln Lys Pro Gly Gln Pro Pro Lys Arg
        35                  40                  45

Leu Ile Tyr Tyr Thr Ser Thr Leu Pro Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Leu Gly Ser Tyr Ser Asp
                85                  90                  95

Asp Ile Tyr Ser Phe Gly Gly Gly Thr Glu Val Val Val Lys
            100                 105                 110

<210> SEQ ID NO 136
<211> LENGTH: 110
<212> TYPE: PRT
<213> ORGANISM: Oryctolagus cuniculus

<400> SEQUENCE: 136

Asp Pro Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Lys Asn
            20                  25                  30

Lys Tyr Leu Ser Trp Phe Gln Gln Lys Pro Gly Gln Pro Pro Lys Arg
        35                  40                  45
```

```
Leu Ile Tyr Tyr Val Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Ser Tyr Ser Asn
                85                  90                  95

Asp Ile Tyr Ser Phe Gly Gly Gly Thr Glu Val Val Val Lys
            100                 105                 110
```

<210> SEQ ID NO 137
<211> LENGTH: 402
<212> TYPE: DNA
<213> ORGANISM: Oryctolagus cuniculus

<400> SEQUENCE: 137

```
atggacacga gggcccccac tcagctgctg gggctcctgc tgctctggct cccaggtgcc    60
acatttgcgc aagtgctgac ccagactgca tcgcccgtgt ctgcacctgt gggaggcaca   120
gtcaccatca attgccagtc cagtcagagt gtttataata acaacgaatt atcttggtat   180
cagcagaaac aggacagcc tcccaagctc ctgatctatg ctgcatccat tttggcatct   240
ggggtcccat tgcggttcaa aggcagtgga tctgggacac agttcactct caccatcagc   300
gacctggagt gtgacgatgc tgccacttac tactgtcaag gcagttatta tagtggtggt   360
tggtacaatg ctttcggcgg agggaccgag gtggtggtca aa                     402
```

<210> SEQ ID NO 138
<211> LENGTH: 134
<212> TYPE: PRT
<213> ORGANISM: Oryctolagus cuniculus

<400> SEQUENCE: 138

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Pro Val Gly Gly Thr Val Thr Ile Asn Cys Gln Ser Ser
        35                  40                  45

Gln Ser Val Tyr Asn Asn Asn Glu Leu Ser Trp Tyr Gln Gln Lys Pro
    50                  55                  60

Gly Gln Pro Pro Lys Leu Leu Ile Tyr Ala Ala Ser Ile Leu Ala Ser
65                  70                  75                  80

Gly Val Pro Leu Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Gln Gly Ser Tyr Tyr Ser Gly Gly Trp Tyr Asn Ala Phe Gly Gly Gly
        115                 120                 125

Thr Glu Val Val Val Lys
    130
```

<210> SEQ ID NO 139
<211> LENGTH: 36
<212> TYPE: DNA
<213> ORGANISM: Artificial Sequence
<220> FEATURE:
<223> OTHER INFORMATION: Synthetic Primer

<400> SEQUENCE: 139

```
agcattgtac caaccaccac tataataact gccttg                              36
```

<210> SEQ ID NO 140
<211> LENGTH: 111
<212> TYPE: PRT
<213> ORGANISM: Oryctolagus cuniculus

<400> SEQUENCE: 140

```
Gln Val Leu Thr Gln Thr Ala Ser Pro Val Ser Ala Pro Val Gly Gly
 1               5                  10                  15

Thr Val Thr Ile Asn Cys Gln Ser Ser Gln Ser Val Tyr Asn Asn Asn
             20                  25                  30

Glu Leu Ser Trp Tyr Gln Gln Lys Pro Gly Gln Pro Pro Lys Leu Leu
         35                  40                  45

Ile Tyr Ala Ala Ser Ile Leu Ala Ser Gly Val Pro Leu Arg Phe Lys
     50                  55                  60

Gly Ser Gly Ser Gly Thr Gln Phe Thr Leu Thr Ile Ser Asp Leu Glu
 65                  70                  75                  80

Cys Asp Asp Ala Ala Thr Tyr Tyr Cys Gln Gly Ser Tyr Tyr Ser Gly
                 85                  90                  95

Gly Trp Tyr Asn Ala Phe Gly Gly Gly Thr Glu Val Val Val Lys
                100                 105                 110
```

<210> SEQ ID NO 141
<211> LENGTH: 396
<212> TYPE: DNA
<213> ORGANISM: Oryctolagus cuniculus

<400> SEQUENCE: 141

```
atggacacga gggcccccac tcagctgctg gggctcctgc tgctctggct cccaggtgcc    60
acatttgctc aagtgctgac ccagactcca ccctccgtgt ctgcagctgt gggaggcaca   120
gtcaccatca gttgccagtc cagtcagagc gtttataata taactggtt aggctggtat   180
cagcagaaat cagggcagcc tcccaagctc ctgatctatt atgcatccac tctggcatct   240
ggggtctcat cgcggttcaa aggcagtgga tctgggacac agttcactct caccatcagc   300
gacctggagt gtgacgatgc tgccacttat tattgtgcag gcggttatag tgatatgatg   360
aatgctttcg gcggagggac tgaggtggtg gttaaa                             396
```

<210> SEQ ID NO 142
<211> LENGTH: 132
<212> TYPE: PRT
<213> ORGANISM: Oryctolagus cuniculus

<400> SEQUENCE: 142

```
Met Asp Thr Arg Ala Pro Thr Gln Leu Leu Gly Leu Leu Leu Leu Trp
 1               5                  10                  15

Leu Pro Gly Ala Thr Phe Ala Gln Val Leu Thr Gln Thr Pro Pro Ser
             20                  25                  30

Val Ser Ala Ala Val Gly Gly Thr Val Thr Ile Ser Cys Gln Ser Ser
         35                  40                  45

Gln Ser Val Tyr Asn Asn Asn Trp Leu Gly Trp Tyr Gln Gln Lys Ser
     50                  55                  60

Gly Gln Pro Pro Lys Leu Leu Ile Tyr Tyr Ala Ser Thr Leu Ala Ser
 65                  70                  75                  80

Gly Val Ser Ser Arg Phe Lys Gly Ser Gly Ser Gly Thr Gln Phe Thr
                 85                  90                  95

Leu Thr Ile Ser Asp Leu Glu Cys Asp Asp Ala Ala Thr Tyr Tyr Cys
```

```
                100               105               110
Ala Gly Gly Tyr Ser Asp Met Met Asn Ala Phe Gly Gly Thr Glu
        115                 120                 125

Val Val Val Lys
    130

<210> SEQ ID NO 143
<211> LENGTH: 30
<212> TYPE: DNA
<213> ORGANISM: Artificial Sequence
<220> FEATURE:
<223> OTHER INFORMATION: Synthetic Primer

<400> SEQUENCE: 143
gcaggcggtt atagtgatat gatgaatgct                                    30

<210> SEQ ID NO 144
<211> LENGTH: 109
<212> TYPE: PRT
<213> ORGANISM: Oryctolagus cuniculus

<400> SEQUENCE: 144

Gln Val Leu Thr Gln Thr Pro Pro Ser Val Ser Ala Ala Val Gly Gly
  1               5                  10                  15

Thr Val Thr Ile Ser Cys Gln Ser Ser Gln Ser Val Tyr Asn Asn Asn
             20                  25                  30

Trp Leu Gly Trp Tyr Gln Gln Lys Ser Gly Gln Pro Pro Lys Leu Leu
         35                  40                  45

Ile Tyr Tyr Ala Ser Thr Leu Ala Ser Gly Val Ser Ser Arg Phe Lys
 50                  55                  60

Gly Ser Gly Ser Gly Thr Gln Phe Thr Leu Thr Ile Ser Asp Leu Glu
 65                  70                  75                  80

Cys Asp Asp Ala Ala Thr Tyr Tyr Cys Ala Gly Gly Tyr Ser Asp Met
                 85                  90                  95

Met Asn Ala Phe Gly Gly Gly Thr Glu Val Val Val Lys
            100                 105

<210> SEQ ID NO 145
<211> LENGTH: 384
<212> TYPE: DNA
<213> ORGANISM: Oryctolagus cuniculus

<400> SEQUENCE: 145
atggagactg ggctgcgctg gcttctcctg gtcgctgtgc tcaaaggtgt ccagtgtcag     60
tcggtggagg agtccggggg tcgcctggtc acgcctggga cacccctgac actcgcctgc    120
accgtctctg gattctccct gaggagctat gcaatgatct gggtccgcca ggctccaggg    180 aggggctgg aatggatcgc ggcctttggt actagtggca ctacaaacta cgcgagctgg    240
gcaaaaggcc gattcaccat ctccagaacc tcgaacacgg tgtatctcaa aatcaccagt    300
ccgacaaccg aggacacggc cacctatttc tgtgccagac aatggagttt gtggggccca    360
ggcaccctgg tcaccgtctc ctca                                           384

<210> SEQ ID NO 146
<211> LENGTH: 128
<212> TYPE: PRT
<213> ORGANISM: Oryctolagus cuniculus

<400> SEQUENCE: 146

Met Glu Thr Gly Leu Arg Trp Leu Leu Leu Val Ala Val Leu Lys Gly
```

-continued

```
                1               5                  10                 15
Val Gln Cys Gln Ser Val Glu Glu Ser Gly Gly Arg Leu Val Thr Pro
                    20                  25                  30

Gly Thr Pro Leu Thr Leu Ala Cys Thr Val Ser Gly Phe Ser Leu Arg
            35                  40                  45

Ser Tyr Ala Met Ile Trp Val Arg Gln Ala Pro Gly Glu Gly Leu Glu
        50                  55                  60

Trp Ile Ala Ala Phe Gly Thr Ser Gly Thr Thr Asn Tyr Ala Ser Trp
 65                 70                  75                  80

Ala Lys Gly Arg Phe Thr Ile Ser Arg Thr Ser Asn Thr Val Tyr Leu
                85                  90                  95

Lys Ile Thr Ser Pro Thr Thr Glu Asp Thr Ala Thr Tyr Phe Cys Ala
                    100                 105                 110

Arg Gln Trp Ser Leu Trp Gly Pro Gly Thr Leu Val Thr Val Ser Ser
            115                 120                 125
```

<210> SEQ ID NO 147
<211> LENGTH: 45
<212> TYPE: DNA
<213> ORGANISM: Artificial Sequence
<220> FEATURE:
<223> OTHER INFORMATION: Synthetic Primer

<400> SEQUENCE: 147
tgaggagacg gtgaccaggg tgcctgggcc ccacaaactc cattg                    45

<210> SEQ ID NO 148
<211> LENGTH: 21
<212> TYPE: DNA
<213> ORGANISM: Artificial Sequence
<220> FEATURE:
<223> OTHER INFORMATION: Synthetic Primer

<400> SEQUENCE: 148
ctgcgctggc ttctcctggt c                                              21

<210> SEQ ID NO 149
<211> LENGTH: 109
<212> TYPE: PRT
<213> ORGANISM: Oryctolagus cuniculus

<400> SEQUENCE: 149

```
Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Thr Tyr Ala
            20                  25                  30

Met Ile Trp Val Arg Gln Ala Pro Gly Glu Gly Leu Glu Trp Ile Ala
        35                  40                  45

Ala Phe Gly Thr Ser Gly Thr Thr Asn Tyr Ala Thr Trp Ala Lys Gly
    50                  55                  60

Arg Phe Thr Ile Ser Arg Thr Ser Asn Thr Met Asp Leu Arg Ile Thr
 65                 70                  75                  80

Ser Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
            100                 105
```

<210> SEQ ID NO 150
<211> LENGTH: 109
<212> TYPE: PRT

<213> ORGANISM: Oryctolagus cuniculus

<400> SEQUENCE: 150

Gln Ser Val Glu Glu Phe Gly Gly Arg Leu Val Thr Pro Gly Thr Pro
1               5                   10                  15

Leu Thr Leu Thr Cys Thr Val Ser Gly Phe Ser Leu Ser Thr Val Ala
                20                  25                  30

Met Ile Trp Val Arg Gln Ala Pro Gly Glu Gly Leu Glu Trp Ile Ala
            35                  40                  45

Ala Phe Gly Thr Ser Gly Thr Thr Asn Tyr Ala Thr Trp Ala Lys Gly
        50                  55                  60

Arg Phe Thr Ile Ser Arg Thr Ser Asn Thr Val Asp Leu Arg Ile Thr
65                  70                  75                  80

Arg Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
                100                 105

<210> SEQ ID NO 151
<211> LENGTH: 109
<212> TYPE: PRT
<213> ORGANISM: Oryctolagus cuniculus

<400> SEQUENCE: 151

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Val Ala
                20                  25                  30

Met Ile Trp Val Arg Gln Ala Pro Gly Glu Gly Leu Glu Trp Ile Ala
            35                  40                  45

Ala Phe Gly Thr Ser Gly Thr Thr Asn Tyr Ala Thr Trp Ala Lys Gly
        50                  55                  60

Arg Phe Thr Ile Ser Arg Thr Ser Asn Thr Val Asp Leu Arg Ile Thr
65                  70                  75                  80

Arg Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
                100                 105

<210> SEQ ID NO 152
<211> LENGTH: 109
<212> TYPE: PRT
<213> ORGANISM: Oryctolagus cuniculus

<400> SEQUENCE: 152

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Val Ala
                20                  25                  30

Met Ile Trp Val Arg Gln Ala Pro Gly Glu Gly Leu Gln Trp Ile Ala
            35                  40                  45

Ala Phe Gly Thr Arg Gly Thr Thr Asn Tyr Ala Thr Trp Ala Lys Gly
        50                  55                  60

Arg Phe Thr Ile Ser Arg Thr Ser Asn Thr Val Asp Leu Arg Ile Thr
65                  70                  75                  80

Ser Pro Thr Thr Glu Asp Thr Ala Thr Tyr Phe Cys Ala Arg Gln Trp
                85                  90                  95

```
Ser Leu Trp Gly Pro Gly Thr Leu Val Thr Val Ser Ser
            100                 105
```

<210> SEQ ID NO 153
<211> LENGTH: 109
<212> TYPE: PRT
<213> ORGANISM: Oryctolagus cuniculus

<400> SEQUENCE: 153

```
Gln Ser Val Glu Glu Ser Gly Gly Arg Leu Val Thr Pro Gly Thr Pro
 1               5                  10                  15

Leu Thr Leu Thr Cys Thr Val Ser Gly Val Ser Leu Arg Gly Tyr Ala
            20                  25                  30

Met Ile Trp Val Arg Gln Ala Pro Gly Glu Gly Leu Lys Trp Ile Ala
        35                  40                  45

Ala Phe Gly Thr Ser Gly Thr Thr Asn Tyr Ala Ser Trp Ala Lys Gly
    50                  55                  60

Arg Phe Thr Ile Ser Arg Thr Ser Asn Thr Val Asp Leu Lys Ile Thr
65                  70                  75                  80

Ser Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
            100                 105
```

<210> SEQ ID NO 154
<211> LENGTH: 109
<212> TYPE: PRT
<213> ORGANISM: Oryctolagus cuniculus

<400> SEQUENCE: 154

```
Gln Ser Val Glu Glu Ser Gly Gly Arg Leu Val Thr Pro Gly Thr Pro
 1               5                  10                  15

Leu Thr Leu Thr Cys Thr Ile Ser Gly Val Ser Leu Arg Gly Tyr Ala
            20                  25                  30

Met Ile Trp Val Arg Gln Ala Pro Gly Glu Gly Leu Lys Trp Ile Ala
        35                  40                  45

Ala Phe Gly Thr Ser Gly Thr Thr Asn Tyr Ala Ser Trp Ala Lys Gly
    50                  55                  60

Arg Phe Thr Ile Ser Arg Thr Ser Asn Thr Val Asp Leu Lys Ile Thr
65                  70                  75                  80

Ser Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
            100                 105
```

<210> SEQ ID NO 155
<211> LENGTH: 109
<212> TYPE: PRT
<213> ORGANISM: Oryctolagus cuniculus

<400> SEQUENCE: 155

```
Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Arg Ser Tyr Ala
            20                  25                  30

Met Ile Trp Val Arg Gln Ala Pro Gly Glu Gly Leu Glu Trp Ile Ala
        35                  40                  45

Ala Phe Gly Thr Ser Gly Thr Thr Asn Tyr Ala Ser Trp Ala Lys Gly
    50                  55                  60
```

```
Arg Phe Thr Ile Ser Arg Thr Ser Asn Thr Val Tyr Leu Lys Ile Thr
 65                  70                  75                  80

Ser Pro Thr Thr Glu Asp Thr Ala Thr Tyr Phe Cys Ala Arg Gln Trp
                 85                  90                  95

Ser Leu Trp Gly Pro Gly Thr Leu Val Thr Val Ser Ser
            100                 105

<210> SEQ ID NO 156
<211> LENGTH: 109
<212> TYPE: PRT
<213> ORGANISM: Oryctolagus cuniculus

<400> SEQUENCE: 156

Gln Ser Val Glu Glu Ser Gly Gly Arg Leu Val Thr Pro Gly Thr Pro
  1               5                  10                  15

Leu Thr Leu Thr Cys Thr Val Ser Gly Phe Ser Leu Arg Ser Tyr Ala
                 20                  25                  30

Met Ile Trp Val Arg Gln Ala Pro Gly Glu Gly Leu Glu Trp Ile Ala
             35                  40                  45

Ala Phe Gly Thr Gly Thr Thr Asn Tyr Ala Ser Trp Ala Lys Gly
         50                  55                  60

Arg Phe Thr Ile Ser Arg Thr Ser Asn Thr Val Tyr Leu Arg Ile Thr
 65                  70                  75                  80

Ser Pro Thr Thr Glu Asp Thr Ala Thr Tyr Phe Cys Ala Arg Gln Trp
                 85                  90                  95

Ser Leu Trp Gly Pro Gly Thr Leu Val Thr Val Ser Ser
            100                 105

<210> SEQ ID NO 157
<211> LENGTH: 109
<212> TYPE: PRT
<213> ORGANISM: Oryctolagus cuniculus

<400> SEQUENCE: 157

Gln Ser Val Glu Glu Ser Gly Gly Arg Leu Val Thr Pro Gly Thr Pro
  1               5                  10                  15

Leu Thr Leu Thr Cys Thr Val Ser Gly Phe Ser Leu Ser Ser Tyr Ala
                 20                  25                  30

Met Ile Trp Val Arg Gln Ala Pro Gly Glu Gly Leu Glu Trp Ile Ala
             35                  40                  45

Ala Phe Gly Thr Gly Ser Thr Asn Tyr Ala Ser Trp Ala Lys Gly
         50                  55                  60

Arg Phe Thr Ile Ser Arg Thr Ser Asn Thr Met His Leu Lys Ile Thr
 65                  70                  75                  80

Ser Pro Thr Thr Glu Asp Thr Ala Thr Tyr Phe Cys Ala Arg Gln Trp
                 85                  90                  95

Ser Leu Trp Gly Pro Gly Thr Leu Val Thr Val Ser Ser
            100                 105

<210> SEQ ID NO 158
<211> LENGTH: 109
<212> TYPE: PRT
<213> ORGANISM: Oryctolagus cuniculus

<400> SEQUENCE: 158

Gln Ser Val Glu Glu Ser Gly Gly Arg Leu Val Thr Pro Gly Thr Pro
  1               5                  10                  15

Leu Thr Leu Thr Cys Thr Val Ser Gly Ile Asp Leu Ser Asn Tyr Ala
```

```
                    20                  25                  30
Met Ile Trp Val Arg Gln Ala Pro Gly Glu Gly Leu Glu Trp Ile Ala
            35                  40                  45

Ala Phe Gly Thr Ser Gly Ser Ala Ser Tyr Ala Ser Trp Ala Lys Gly
        50                  55                  60

Arg Phe Thr Ile Ser Lys Thr Ser Asn Thr Val Asp Leu Lys Ile Thr
 65                  70                  75                  80

Ser Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
                100                 105

<210> SEQ ID NO 159
<211> LENGTH: 109
<212> TYPE: PRT
<213> ORGANISM: Oryctolagus cuniculus

<400> SEQUENCE: 159

Gln Ser Val Glu Glu Ser Gly Gly Arg Leu Val Thr Pro Gly Thr Pro
 1               5                   10                  15

Leu Thr Leu Thr Cys Thr Val Ser Gly Ile Asp Leu Ser Lys Tyr Ala
                20                  25                  30

Met Ile Trp Val Arg Gln Ala Pro Gly Glu Gly Leu Lys Trp Ile Ala
            35                  40                  45

Ala Leu Gly Ala Ser Gly Thr Thr Asn Tyr Ala Ser Trp Ala Lys Gly
        50                  55                  60

Arg Phe Thr Ile Ser Arg Thr Ser Asn Thr Val Asp Leu Lys Ile Thr
 65                  70                  75                  80

Ser Pro Thr Thr Glu Asp Thr Ala Thr Tyr Phe Cys Ala Arg Gln Trp
                85                  90                  95

Ser Leu Trp Gly Pro Gly Thr Leu Val Thr Val Ser Ser
                100                 105

<210> SEQ ID NO 160
<211> LENGTH: 109
<212> TYPE: PRT
<213> ORGANISM: Oryctolagus cuniculus

<400> SEQUENCE: 160

Gln Ser Val Glu Glu Ser Gly Gly Arg Leu Val Thr Pro Gly Thr Pro
 1               5                   10                  15

Leu Thr Leu Thr Cys Thr Val Ser Gly Phe Ser Leu Ser Ser Tyr Ala
                20                  25                  30

Met Ile Trp Val Arg Gln Ala Pro Gly Lys Gly Leu Glu Trp Ile Ala
            35                  40                  45

Ala Phe Gly Thr Ser Gly Thr Thr Asn Tyr Ala Ser Trp Ala Lys Gly
        50                  55                  60

Arg Phe Thr Ile Ser Lys Thr Ser Asn Thr Val Asp Leu Lys Ile Thr
 65                  70                  75                  80

Ser Pro Thr Pro Gly Asp Thr Ala Thr Tyr Phe Cys Ala Arg Gln Trp
                85                  90                  95

Ser Leu Trp Gly Pro Gly Thr Leu Val Thr Ile Ser Ser
                100                 105

<210> SEQ ID NO 161
<211> LENGTH: 109
<212> TYPE: PRT
<213> ORGANISM: Oryctolagus cuniculus
```

<400> SEQUENCE: 161

Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Ala
            20                  25                  30
Met Ile Trp Val Arg Gln Ala Pro Gly Lys Gly Leu Glu Trp Ile Ala
        35                  40                  45
Ala Phe Gly Thr Ser Gly Thr Arg Asn Tyr Ala Ser Trp Ala Lys Gly
    50                  55                  60
Arg Phe Thr Ile Ser Arg Thr Ser Thr Thr Val Asp Leu Lys Met Thr
65                  70                  75                  80
Ser Leu Thr Thr Glu Asp Thr Ala Thr Tyr Phe Cys Ala Arg Gln Trp
                85                  90                  95
Ser Leu Trp Gly Pro Gly Thr Leu Val Thr Val Ser Ser
            100                 105

<210> SEQ ID NO 162
<211> LENGTH: 109
<212> TYPE: PRT
<213> ORGANISM: Oryctolagus cuniculus

<400> SEQUENCE: 162

Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Gly Ser Tyr Ala
            20                  25                  30
Met Ile Trp Val Arg Gln Ala Pro Gly Lys Gly Leu Glu Trp Ile Ala
        35                  40                  45
Ala Phe Gly Thr Ser Gly Thr Arg Asn Tyr Ala Ser Trp Ala Lys Gly
    50                  55                  60
Arg Phe Thr Ile Ser Arg Thr Ser Thr Thr Val Asp Leu Lys Met Thr
65                  70                  75                  80
Ser Leu Thr Thr Glu Asp Thr Ala Thr Tyr Phe Cys Ala Arg Gln Trp
                85                  90                  95
Ser Leu Trp Gly Pro Gly Thr Leu Val Thr Val Ser Ser
            100                 105

<210> SEQ ID NO 163
<211> LENGTH: 399
<212> TYPE: DNA
<213> ORGANISM: Oryctolagus cuniculus

<400> SEQUENCE: 163
atggagactg ggctgcgctg gcttctcctg gtcgctgtgc tcaaaggtgt ccagtgtcag    60
tcgctggagg agtccggggg tcgcctggta acgcctggag atccctgac actcacctgc   120
acagtctctg gaatcgacct cagtacctat ccaatgggct gggtccgcca ggctccaggg   180
aagggggctgg aatacatcgg aatcgttttt cctagtcttg gctcatatta cgcgagctgg   240
gcaaaaggcc gattcaccat ctccaaaacc tcgtcaacca cggtggatct cgcatgacc   300
agtctgacaa ccgaggacac ggccacctat ttctgtgcca gagggtaac taatagttgg   360
gatccctggg gcccaggcac cctggtcacc gtctcctca                          399

<210> SEQ ID NO 164
<211> LENGTH: 133
<212> TYPE: PRT
<213> ORGANISM: Oryctolagus cuniculus

<400> SEQUENCE: 164

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Ile Asp Leu Ser
        35                  40                  45

Thr Tyr Pro Met Gly Trp Val Arg Gln Ala Pro Gly Lys Gly Leu Glu
    50                  55                  60

Tyr Ile Gly Ile Val Phe Pro Ser Leu Gly Ser Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Arg Met Thr Ser Leu Thr Thr Glu Asp Thr Ala Thr Tyr Phe Cys
            100                 105                 110

Ala Arg Gly Val Thr Asn Ser Trp Asp Pro Trp Gly Pro Gly Thr Leu
        115                 120                 125

Val Thr Val Ser Ser
    130

<210> SEQ ID NO 165
<211> LENGTH: 26
<212> TYPE: DNA
<213> ORGANISM: Artificial Sequence
<220> FEATURE:
<223> OTHER INFORMATION: Synthetic Primer

<400> SEQUENCE: 165
cccagggatc ccaactatta gttacc                                        26

<210> SEQ ID NO 166
<211> LENGTH: 114
<212> TYPE: PRT
<213> ORGANISM: Oryctolagus cuniculus

<400> SEQUENCE: 166

Gln Ser Leu Glu Glu Ser Gly Gly Arg Leu Val Ser Pro Gly Gly Ser
1               5                   10                  15

Leu Thr Leu Thr Cys Thr Val Ser Gly Ile Asp Leu Ser Thr Tyr Pro
            20                  25                  30

Met Gly Trp Val Arg Gln Ala Pro Gly Lys Gly Leu Glu Tyr Ile Gly
        35                  40                  45

Ile Val Phe Pro Ser Leu Gly Ser Tyr Tyr Ala Ser Trp Ala Lys Gly
    50                  55                  60

Arg Phe Thr Ile Ser Lys Thr Ser Ser Thr Thr Val Asp Leu Arg Met
65                  70                  75                  80

Thr Ser Leu Thr Ala Glu Asp Thr Ala Thr Tyr Phe Cys Ala Arg Gly
                85                  90                  95

Val Thr Asn Ser Trp Asp Pro Trp Gly Pro Gly Thr Val Val Thr Val
            100                 105                 110

Ser Ser

<210> SEQ ID NO 167
<211> LENGTH: 114
<212> TYPE: PRT
<213> ORGANISM: Oryctolagus cuniculus

<400> SEQUENCE: 167

Gln Ser Leu Glu Glu Ser Gly Gly Arg Leu Val Thr Pro Gly Gly Ser
 1               5                   10                  15

Leu Thr Leu Thr Cys Thr Val Ser Gly Ile Asp Leu Ser Thr Tyr Pro
            20                  25                  30

Met Gly Trp Val Arg Gln Ala Pro Gly Lys Gly Leu Glu Tyr Ile Gly
        35                  40                  45

Ile Val Phe Pro Ser Leu Gly Ser Tyr Tyr Ala Ser Trp Ala Lys Gly
    50                  55                  60

Arg Phe Thr Ile Ser Lys Thr Ser Ser Thr Val Asp Leu Arg Met
65                  70                  75                  80

Thr Ser Leu Thr Thr Glu Asp Thr Ala Thr Tyr Phe Cys Ala Arg Gly
                85                  90                  95

Val Thr Asn Ser Trp Asp Pro Trp Gly Pro Gly Thr Leu Val Thr Val
                100                 105                 110

Ser Ser

<210> SEQ ID NO 168
<211> LENGTH: 114
<212> TYPE: PRT
<213> ORGANISM: Oryctolagus cuniculus

<400> SEQUENCE: 168

Gln Ser Leu Glu Glu Ser Gly Gly Arg Leu Val Thr Pro Gly Gly Ser
 1               5                   10                  15

Leu Thr Leu Thr Cys Thr Val Ser Gly Ile Asp Leu Ser Thr Tyr Pro
            20                  25                  30

Met Gly Trp Val Arg Gln Ala Pro Gly Lys Gly Leu Glu Tyr Ile Gly
        35                  40                  45

Ile Val Phe Pro Asn Ile Gly Ser Tyr Tyr Ala Ser Trp Ala Lys Gly
    50                  55                  60

Arg Phe Thr Ile Ser Ser Thr Ser Ser Thr Thr Val Asp Leu Arg Met
65                  70                  75                  80

Thr Ser Leu Thr Thr Glu Asp Thr Ala Thr Tyr Phe Cys Ala Arg Gly
                85                  90                  95

Val Thr Asn Ser Trp Asp Pro Trp Gly Pro Gly Thr Leu Val Thr Val
                100                 105                 110

Ser Ser

<210> SEQ ID NO 169
<211> LENGTH: 393
<212> TYPE: DNA
<213> ORGANISM: Oryctolagus cuniculus

<400> SEQUENCE: 169
atggagactg ggctgcgctg gcttctcctg gtcgctgtgc tcaaaggtgt ccagtgtcag      60
tcgctggagg agtccggggg tcgcctggta acgcctggag gatccctgac actcacctgc    120
acagtctctg gaatcgacct cagtagctat ggaatgggct gggtccgcca ggctccaggg    180
aagggtctgg aatacatcgc aatcattagt tatggtggta gagcatacta cgcgagctgg    240
gcgaaaggcc gattcaccat ctccagaact tcgaccacgg tggatctgaa atgaccagt    300 ctgacaaccg aggacacggc cacctatttc tgtgccagag gatttagcgc ctttaacttg    360
tggggcccag gcaccctggt caccgtctcc tca                                  393

<210> SEQ ID NO 170
<211> LENGTH: 131

```
<212> TYPE: PRT
<213> ORGANISM: Oryctolagus cuniculus

<400> SEQUENCE: 170

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Ile Asp Leu Ser
        35                  40                  45

Ser Tyr Gly Met Gly Trp Val Arg Gln Ala Pro Gly Lys Gly Leu Glu
    50                  55                  60

Tyr Ile Ala Ile Ile Ser Tyr Gly Gly Arg Ala Tyr Tyr Ala Ser Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Gly Phe Ser Ala Phe Asn Leu Trp Gly Pro Gly Thr Leu Val Thr
        115                 120                 125

Val Ser Ser
        130

<210> SEQ ID NO 171
<211> LENGTH: 26
<212> TYPE: DNA
<213> ORGANISM: Artificial Sequence
<220> FEATURE:
<223> OTHER INFORMATION: Synthetic Primer

<400> SEQUENCE: 171
gccccacaag ttaaaggcgc taaatc                                        26

<210> SEQ ID NO 172
<211> LENGTH: 112
<212> TYPE: PRT
<213> ORGANISM: Oryctolagus cuniculus

<400> SEQUENCE: 172

Gln Ser Leu Glu Glu Ser Gly Gly Arg Leu Val Thr Pro Gly Gly Ser
 1               5                  10                  15

Leu Thr Leu Thr Cys Thr Val Ser Gly Ile Asp Leu Ser Ser Tyr Gly
            20                  25                  30

Met Gly Trp Val Arg Gln Ala Pro Gly Lys Gly Leu Glu Tyr Ile Ala
        35                  40                  45

Ile Ile Ser Tyr Gly Gly Arg Ala Tyr Tyr Ala Ser Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Gly Phe
                85                  90                  95

Ser Ala Phe Asn Leu Trp Gly Pro Gly Thr Leu Val Thr Val Ser Ser
            100                 105                 110

<210> SEQ ID NO 173
<211> LENGTH: 399
<212> TYPE: DNA
<213> ORGANISM: Oryctolagus cuniculus

<400> SEQUENCE: 173
```

```
atggagactg ggctgcgctg gcttctcctg gtcgctgtgc tcaaaggtgt ccagtgtcag        60
tcggtggtgg aggagtccgg gggtcgcctg gtcacgcctg gacacccct gacactcacc       120 tgcacagcct ctggattctc cctcagtagg tttgcaatga ggtgggtccg ccaggctcca       180
gggaaggggc tggaatacat cggagccatc gagactgatg gtaggacata ctacgcgagg       240
tgggcgaaag gccgattcac catttccaag acctcgaccg cggtgcatct gaagttcacc       300
agtccgacaa ccgaggacac gggcacgtat ttctgtacca gagggctggt tacaatttct       360
actttgtggg gcccaggcac cctggtcacc gtctcctca                             399
```

<210> SEQ ID NO 174
<211> LENGTH: 133
<212> TYPE: PRT
<213> ORGANISM: Oryctolagus cuniculus

<400> SEQUENCE: 174

```
Met Glu Thr Gly Leu Arg Trp Leu Leu Leu Val Ala Val Leu Lys Gly
  1               5                  10                  15

Val Gln Cys Gln Ser Val Val Glu Glu Ser Gly Gly Arg Leu Val Thr
             20                  25                  30

Pro Gly Thr Pro Leu Thr Leu Thr Cys Thr Ala Ser Gly Phe Ser Leu
         35                  40                  45

Ser Arg Phe Ala Met Arg Trp Val Arg Gln Ala Pro Gly Lys Gly Leu
     50                  55                  60

Glu Tyr Ile Gly Ala Ile Glu Thr Asp Gly Arg Thr Tyr Tyr Ala Arg
 65                  70                  75                  80

Trp Ala Lys Gly Arg Phe Thr Ile Ser Lys Thr Ser Thr Ala Val His
                 85                  90                  95

Leu Lys Phe Thr Ser Pro Thr Thr Glu Asp Thr Gly Thr Tyr Phe Cys
            100                 105                 110

Thr Arg Gly Leu Val Thr Ile Ser Thr Leu Trp Gly Pro Gly Thr Leu
        115                 120                 125

Val Thr Val Ser Ser
    130
```

<210> SEQ ID NO 175
<211> LENGTH: 28
<212> TYPE: DNA
<213> ORGANISM: Artificial Sequence
<220> FEATURE:
<223> OTHER INFORMATION: Synthetic Primer

<400> SEQUENCE: 175

```
gccccacaaa gtagaaattg taaccagc                                          28
```

<210> SEQ ID NO 176
<211> LENGTH: 114
<212> TYPE: PRT
<213> ORGANISM: Oryctolagus cuniculus

<400> SEQUENCE: 176

```
Gln Ser Val Val Glu Glu Ser Gly Gly Arg Leu Val Thr Pro Gly Thr
  1               5                  10                  15

Pro Leu Thr Leu Thr Cys Thr Ala Ser Gly Phe Ser Leu Ser Arg Phe
             20                  25                  30

Ala Met Arg Trp Val Arg Gln Ala Pro Gly Lys Gly Leu Glu Tyr Ile
         35                  40                  45

Gly Ala Ile Glu Thr Asp Gly Arg Thr Tyr Tyr Ala Arg Trp Ala Lys
```

```
            50                  55                  60
Gly Arg Phe Thr Ile Ser Lys Thr Ser Thr Ala Val His Leu Lys Phe
 65                  70                  75                  80

Thr Ser Pro Thr Thr Glu Asp Thr Gly Thr Tyr Phe Cys Thr Arg Gly
                 85                  90                  95

Leu Val Thr Ile Ser Thr Leu Trp Gly Pro Gly Thr Leu Val Thr Val
            100                 105                 110

Ser Ser

<210> SEQ ID NO 177
<211> LENGTH: 43
<212> TYPE: DNA
<213> ORGANISM: Artificial Sequence
<220> FEATURE:
<223> OTHER INFORMATION: Synthetic Primer

<400> SEQUENCE: 177
caccatggag actgggctgc gctggcttct cctggtcgct gtg                     43

<210> SEQ ID NO 178
<211> LENGTH: 37
<212> TYPE: DNA
<213> ORGANISM: Artificial Sequence
<220> FEATURE:
<223> OTHER INFORMATION: Synthetic Primer

<400> SEQUENCE: 178
ctcccgctct ccgggtaaat gagcgctgtg ccggcga                            37

<210> SEQ ID NO 179
<211> LENGTH: 36
<212> TYPE: DNA
<213> ORGANISM: Artificial Sequence
<220> FEATURE:
<223> OTHER INFORMATION: Synthetic Primer

<400> SEQUENCE: 179
caggcaggac ccagcatgga cacgagggcc cccact                             36

<210> SEQ ID NO 180
<211> LENGTH: 34
<212> TYPE: DNA
<213> ORGANISM: Artificial Sequence
<220> FEATURE:
<223> OTHER INFORMATION: Synthetic Primer

<400> SEQUENCE: 180
tcaatagggg tgactgttag agcgagacgc tgc                                34

<210> SEQ ID NO 181
<211> LENGTH: 43
<212> TYPE: DNA
<213> ORGANISM: Artificial Sequence
<220> FEATURE:
<223> OTHER INFORMATION: Synthetic Primer

<400> SEQUENCE: 181
caccatggag actgggctgc gctggcttct cctggtcgct gtg                     43

<210> SEQ ID NO 182
<211> LENGTH: 37
<212> TYPE: DNA
<213> ORGANISM: Artificial Sequence
<220> FEATURE:
<223> OTHER INFORMATION: Synthetic Primer
```

```
<400> SEQUENCE: 182
ctcccgctct ccgggtaaat gagcgctgtg ccggcga                              37

<210> SEQ ID NO 183
<211> LENGTH: 36
<212> TYPE: DNA
<213> ORGANISM: Artificial Sequence
<220> FEATURE:
<223> OTHER INFORMATION: Synthetic Primer

<400> SEQUENCE: 183
caggcaggac ccagcatgga cacgagggcc cccact                               36

<210> SEQ ID NO 184
<211> LENGTH: 34
<212> TYPE: DNA
<213> ORGANISM: Artificial Sequence
<220> FEATURE:
<223> OTHER INFORMATION: Synthetic Primer

<400> SEQUENCE: 184 tcaataggggg tgactgttag agcgagacgc ctgc                                34

<210> SEQ ID NO 185
<211> LENGTH: 20
<212> TYPE: DNA
<213> ORGANISM: Artificial Sequence
<220> FEATURE:
<223> OTHER INFORMATION: Synthetic Primer

<400> SEQUENCE: 185
aattcacatt gattattgag                                                 20

<210> SEQ ID NO 186
<211> LENGTH: 40
<212> TYPE: DNA
<213> ORGANISM: Artificial Sequence
<220> FEATURE:
<223> OTHER INFORMATION: Synthetic Primer

<400> SEQUENCE: 186
cagcgcagcc cagtctccat cccgtaagca gtgggttctc                           40

<210> SEQ ID NO 187
<211> LENGTH: 40
<212> TYPE: DNA
<213> ORGANISM: Artificial Sequence
<220> FEATURE:
<223> OTHER INFORMATION: Synthetic Primer

<400> SEQUENCE: 187
ccgggtaaat gagcgctgtg gtttaaaccc gctgatcagc                           40

<210> SEQ ID NO 188
<211> LENGTH: 20
<212> TYPE: DNA
<213> ORGANISM: Artificial Sequence
<220> FEATURE:
<223> OTHER INFORMATION: Synthetic Primer

<400> SEQUENCE: 188
aagccataga gccgaccgca                                                 20

<210> SEQ ID NO 189
<211> LENGTH: 11
```

```
<212> TYPE: DNA
<213> ORGANISM: Artificial Sequence
<220> FEATURE:
<223> OTHER INFORMATION: Synthetic oligonucleotide

<400> SEQUENCE: 189
cggaacaagg g                                                           11

<210> SEQ ID NO 190
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 190
cggaacaagg g                                                           11
```

What is claimed is:

1. A method comprising:
   obtaining the amino acid sequences of at least the CDR3 regions of a plurality of immunoglobulin heavy chains and a plurality of immunoglobulin light chains from an individual that has been immunized with an antigen;
   grouping said immunoglobulin heavy chain sequences so that immunoglobulin heavy chain sequences within each group are related to one another by lineage, wherein said grouping the immunoglobulin heavy chain sequences comprises comparing the heavy chain CDR3 sequences to one another and wherein the immunoglobulin heavy chains within each group have the same heavy chain CDR3 amino acid sequence and the different groups contain heavy chains that have different heavy chain CDR3 amino acid sequences;
   grouping said immunoglobulin light chains sequences so that immunoglobulin light chain sequences within each group are related to one another by lineage, wherein said grouping the immunoglobulin light chain sequences comprises comparing the heavy chain CDR3 sequences to one another and wherein the immunoglobulin light chains within each group have the same light chain CDR3 amino acid sequence and the different groups contain light chains that have different light chain CDR3 amino acid sequences;
   selecting a single heavy chain from each of a plurality of the heavy chain groups and a single light chain from each of a plurality of the light chain groups to produce a plurality of candidate heavy chains and a plurality of candidate light chains; and
   testing said candidate heavy chains and said candidate light chains in a pairwise manner for binding to said antigen.

2. The method of claim 1, wherein said obtaining comprises obtaining at least 1,000 heavy chain CDR3 sequences and at least 1,000 light chain CDR3 sequences from a population of antibody-producing cells obtained from said individual.

3. The method of claim 1, further comprising identifying an antibody that binds to said antigen.

4. The method of claim 3, wherein the identified antibody has non-naturally paired heavy and light chains.

5. The method of claim 1, wherein the individual is a mouse.

6. The method of claim 1, wherein the individual is a rabbit.

7. The method of claim 1, wherein said obtaining is done by sequencing cDNA encoding said immunoglobulin heavy chains and said immunoglobulin light chains.

8. The method of claim 1, wherein said obtaining comprises amplifying polynucleotides encoding said immunoglobulin heavy chains and said immunoglobulin light chains from cDNA using universal primers, and then sequencing said polynucleotides.

9. The method of claim 1, wherein said immunoglobulin heavy and light chains are from antibodies that are enriched.

10. The method of claim 1, wherein said testing comprises systematically testing all of said candidate heavy chains and all of said candidate light chains in a pairwise manner to identify an antibody that binds to said antigen.

11. The method of claim 1, wherein said testing is done by ELISA.

12. The method of claim 1, wherein said testing is done using a blocking assay or a neutralization assay.

13. The method of claim 1, wherein said selecting comprises selecting a single heavy chain from each of at least 20% of the heavy chain groups selecting a single light chain from each of at least 20% of the light chain groups.

14. The method of claim 1, wherein said selecting comprises selecting a single heavy chain from each of at least 80% of the heavy chain groups selecting a single light chain from each of at least 80% of the light chain groups.

* * * * *

UNITED STATES PATENT AND TRADEMARK OFFICE
CERTIFICATE OF CORRECTION

PATENT NO. : 8,617,830 B2
APPLICATION NO. : 13/552517
DATED : December 31, 2013
INVENTOR(S) : Guo-Liang Yu It is certified that error appears in the above-identified patent and that said Letters Patent is hereby corrected as shown below:

In the claims

In column 143, line 42, please replace "heavy" with -- light --

Signed and Sealed this
Twelfth Day of July, 2016

Michelle K. Lee
*Director of the United States Patent and Trademark Office*